US008742070B2

(12) United States Patent
Timmerman et al.

(10) Patent No.: US 8,742,070 B2
(45) Date of Patent: *Jun. 3, 2014

(54) METHOD FOR SELECTING A CANDIDATE DRUG COMPOUND

(75) Inventors: Peter Timmerman, Lelystad (NL); Joris Beld, Zürich (CH); Robbert Hans Meloen, Lelystad (NL); Wouter Cornelis Puijk, Lelystad (NL)

(73) Assignee: Pepscan Systems B.V., Lelystad (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,706

(22) Filed: Apr. 10, 2012

(65) Prior Publication Data

US 2013/0158232 A1    Jun. 20, 2013

Related U.S. Application Data

(60) Division of application No. 11/213,443, filed on Aug. 26, 2005, which is a continuation of application No. PCT/NL2004/000146, filed on Feb. 26, 2004.

(30) Foreign Application Priority Data

Feb. 27, 2003   (EP) .................................... 03075597

(51) Int. Cl.
*C07K 17/02* (2006.01)
(52) U.S. Cl.
USPC ........................................................ 530/323
(58) Field of Classification Search
None
See application file for complete search history.

(56) References Cited

U.S. PATENT DOCUMENTS

| | | | |
|---|---|---|---|
| 3,929,758 A | 12/1975 | Hughes et al. | |
| 4,518,711 A | 5/1985 | Hruby et al. | |
| 5,169,833 A | 12/1992 | Hansen, Jr. et al. | |
| 5,216,124 A | 6/1993 | Hansen, Jr. et al. | |
| 5,368,712 A | 11/1994 | Tomich et al. | |
| 5,474,895 A | 12/1995 | Ishii et al. | |
| 5,595,915 A | 1/1997 | Geysen | |
| 5,770,772 A | 6/1998 | Aono et al. | |
| 5,824,483 A | 10/1998 | Houston, Jr. et al. | |
| 5,830,637 A | 11/1998 | Frank et al. | |
| 5,885,577 A | 3/1999 | Alvarez | |
| 6,015,561 A | 1/2000 | Alvarez | |
| 6,461,812 B2 | 10/2002 | Barth et al. | |
| 6,911,307 B1 * | 6/2005 | Dautel et al. | 435/6.16 |
| 2006/0073518 A1 | 4/2006 | Timmerman et al. | |
| 2008/0139407 A1 | 6/2008 | Slootstra et al. | |
| 2010/0322945 A1 | 12/2010 | Timmerman et al. | |

FOREIGN PATENT DOCUMENTS

| | | |
|---|---|---|
| CA | 2047042 | 7/1991 |
| EP | 0467699 A2 | 7/1991 |
| EP | 00203518.6 | 11/2000 |
| EP | 1 197 755 A1 | 4/2002 |
| EP | 1 452 868 A2 | 9/2004 |
| JP | 04-204379 | 7/1992 |
| JP | 2000-235036 | 8/2000 |
| WO | WO 84/03564 A1 | 9/1984 |
| WO | WO 91 08759 | 6/1991 |
| WO | WO 91 09051 | 6/1991 |
| WO | WO 93/09872 A1 | 5/1993 |
| WO | WO 96/09411 A1 | 3/1996 |
| WO | WO 97/00267 A1 | 1/1997 |
| WO | WO 99/20640 | 4/1999 |
| WO | WO 00/11223 A1 | 3/2000 |
| WO | WO 02/31510 A1 | 4/2002 |
| WO | WO 03/095486 A | 11/2003 |
| WO | WO 03/106487 A | 12/2003 |
| WO | WO 2004/077062 A3 | 9/2004 |

OTHER PUBLICATIONS

Jones et al., Immunospecific Reduction of Antiologonucleotide Antibody-Forming Cells with a Tetrakis-oligonucleotide Conjugate (LJP 394), A Therapeutic Candidate for the Treatment of Lupus Nephritis, J. Med. Chem., 1995, pp. 2138-2144, vol. 38.
Ege, Sayhan N. Organic Chemistry $2^{nd}$ edition, §26.3 "Synthesizing peptides and proteins in the laboratory", 1989, p. 1136.
March, Jerry, Advanced Organic Chemistry, 1977, Kinetic Requirements for Reactions, pp. 208-212.
Walker et al., General method for the synthesis of cyclic peptidomimetic compounds, Tetrahedron Letters, 2001, pp. 5801-5804, vol. 42.
Seebeck et al., Ribosomal Synthesis of Dehydroalanine-Containing Peptides, Jacs Communication, published on web, May 13, 2006, J. Am. Chem. Soc., 2006, pp. 7150-7151, vol. 128.
Brown et al., Chemistry, the Central Science, $7^{th}$ Edition, "Aqueous Reactions and Solution Stoichiometry", 1997, pp. 107-114.
Communication from European Patent Office, Result of Consultation, dated Nov. 2, 2010.
Communication from European Patent Office, Communication Pursuant to Article 94(3) EPC, dated Sep. 28, 2010.
Communication from European Patent Office, Communication Under Rule 71(3) EPC, dated Oct. 19, 2009.
Becerril et al., Efficient Macrocyclization of U-Turn Preorganized Peptidomimetics: The Role of Intramolecular H-Bond and Solvophobic Effects, J. Am Chem. Soc., 2003, pp. 6677-6686, vol. 125.

(Continued)

*Primary Examiner* — Thomas Heard
(74) *Attorney, Agent, or Firm* — TraskBritt, P.C.

(57) ABSTRACT

The disclosure relates to the field of candidate drug testing and drug development. Described are methods for providing a compound composed of at least one molecule attached via at least two linkages to a molecular scaffold, the method comprising providing a scaffold comprising at least a first and a second reactive group; providing at least one molecule able to react with the at least first and second reactive group; and contacting the scaffold with at least one molecule to form at least two linkages between the scaffold and the molecule in a coupling reaction, wherein the formation of a linkage accelerates the formation of a consecutive linkage. The coupling reaction may be performed in solution, such as an aqueous solution. Furthermore, described is a method for selecting a candidate drug compound comprising providing a library of the compounds and determining the binding of a target molecule to the compounds.

11 Claims, 21 Drawing Sheets

(56) References Cited

OTHER PUBLICATIONS

Darling et al., Intracellular folding pathway of the cystine knot-containing glycoprotein hormone alpha-subunit, Biochemistry, American Chemical Society, Easton, PA, US, Jan. 16, 2001, pp. 577-585, vol. 40, No. 2.

Englebretsen et al., High Yield, Directed Immobilization of a Peptide-Ligand onto a Beaded Cellulose Support, Peptide Research, 1994, pp. 322-326, vol. 7, No. 6.

International Search Report, International Application No. PCT/NL01/00744, dated Feb. 13, 2002 (4 pages).

Meloen et al., Design of synthetic peptides for diagnostics, Current Protein & Peptide Science, Aug. 2003, pp. 253-260, vol. 4. No. 4.

Murali et al., Structure-Based Design of Immunologically Active Therapeutic Peptides, Immunologic Research, Jan. 1998, pp. 163-169, vol. 17, No. 1/2.

PCT International Search Report, PCT/NL2006/000036, dated May 18, 2006.

Reineke et al., Identification of miniproteins using cellulose-bound duotope scans, Peptides for the New Millennium, The 16th Proceedings of the American Peptide Symposium, presented in Minneapolis, MN, United States, Jun. 26-Jul. 1, 1999 (2000), Meeting Date 1999, 167-169; Eds.: Fields et al., Kluwer Academic Publishers, Dordrecht, Netherlands.

Reineke, Ulrich, et al., "A synthetic mimic of a discontinuous binding site on interleukin-10," 17(3) Nature Biotechnology 271-275 (Mar. 1999).

Sila et al., Topological Templates as Tool in Molecular Recognition and Peptide Mimicry: Synthesis of a Task Library, Journal of Molecular Recognition, 1995, pp. 29-34, vol. 8.

Slootstra et al., Structural Aspects of Antibody-Antigen Interaction Revealed through Small Random Peptide Libraries, Molecular Diversity, Escom Science Publishers, Leiden, NL, 1996, pp. 87-96, vol. 1.

Sun et al., The Cysteine-knot Growth Factor Superfamily, Annual Review of Biophysics and Biomolecular Structure, Annual Reviews Inc., Palo Alto, CA, US, 1995, pp. 269-292, vol. 24.

Timmerman et al., Rapid and quantitative cyclization of multiple peptide loops onto synthetic scaffolds for structural mimicry of prot6ein surfaces, Chembiochem: A European Journal of Chemical Biology, May 2005, pp. 82-124, vol. 6, No. 5.

Timmerman, Mapping of a discontinuous and highly conformational binding site on follicle stimulating hormone subunit beta (FSH-beta) using domain Scan™ and Matris Scan™ technology, Molecular Diversity, 2004, pp. 61-77, vol. 8, No. 2.

Timmerman, P., Functional Reconstruction of Structurally Complex Epitopes using CLIPS™ technology, PowerPoint Presentation, Apr. 8, 2009.

Vitt et al., Evolution and classification of cystine knot-containing hormones and related extracellular signaling molecules, Molecular Endocrinology, Baltimore, MD, US, May 2001, pp. 681-694, vol. 15, No. 5.

Writer et al., Immunology, Meeting Info.: 6th Annual Congress of theBritish Society for Immunology, 1998, vol. 95, No. Suppl. 1, pp. 32.

PCT International Preliminary Examination Report, PCT/NL2004/000146, dated Jul. 27, 2005.

Office Action for U.S. Appl. No. 10/411,869 dated Feb. 23, 2006.
Office Action for U.S. Appl. No. 10/411,869 dated Oct. 19, 2006.
Office Action for U.S. Appl. No. 10/411,869 dated Jul. 16, 2007.
Office Action for U.S. Appl. No. 10/411,869 dated Sep. 18, 2008.
Office Action for U.S. Appl. No. 10/411,869 dated Jun. 30, 2009.
Office Action for U.S. Appl. No. 10/411,869 dated Mar. 18, 2010.
Office Action for U.S. Appl. No. 11/795,922 dated Mar. 24, 2019.
Office Action for U.S. Appl. No. 11/795,922 dated Dec. 14, 2009.
U.S. Appl. No. 13/138,372, filed Nov. 18, 2011, Timmerman et al., Truncated Cystine-Knot Proteins.
U.S. Appl. No. 13/101,894, filed May 5, 2011, Slootstra et al., Identification of Protein Binding Sites.
Jones et al., Multivalent Thioether-Peptide Conjugates: B Cell Tolerance of an Anti-Peptide Immune Response, dated Feb. 19, 1999, Bioconjugate Chem., pp. 480-488, vol. 10.

\* cited by examiner

Hamuro, Y.; Calama, M. C., Park, H. S., Hamilton, A. D., *Angew. Chem. Int. Ed. Engl.* 1997, 36, 2680-2683.

$X_{1,2,3}$ = N(H), O, S
also all other ortho, meta, and para derivatives of the compounds depicted $X_{1,2,3}$ = N(H), O, S
*also all other ortho, meta, and para derivatives of the compounds depicted*

$X_{1,2}$ = N(H), O, S
*also all other possible ortho, meta, and para derivatives of the compounds depicted*

11-mer

1. CVPGAAHHADSLC
2. CRVPGAAHHADSC
3. CVRVPGAAHHADC
4. CTVRVPGAAHHAC
5. CETVRVPGAAHHC
6. CYETVRVPGAAHC

12-mer

1. CVPGAAHHADSLYC
2. CRVPGAAHHADSLC
3. CVRVPGAAHHADSC
4. CTVRVPGAAHHADC
5. CETVRVPGAAHHAC
6. CYETVRVPGAAHHC

13-mer

1. CVPGAAHHADSLYTC
2. CRVPGAAHHADSLYC
3. CVRVPGAAHHADSLC
4. CTVRVPGAAHHADSC
5. CETVRVPGAAHHADC
6. CYETVRVPGAAHHAC

14-mer

1. CVPGAAHHADSLYTYC
2. CRVPGAAHHADSLYTC
3. CVRVPGAAHHADSLYC
4. CTVRVPGAAHHADSLC
5. CETVRVPGAAHHADSC
6. CYETVRVPGAAHHADC

15-mer

1. CVPGAAHHADSLYTYPC
2. CRVPGAAHHADSLYTYC
3. CVRVPGAAHHADSLYTC
4. CTVRVPGAAHHADSLYC
5. CETVRVPGAAHHADSLC
6. CYETVRVPGAAHHADSC

16-mer

1. CVPGAAHHADSLYTYPVC
2. CRVPGAAHHADSLYTYPC
3. CVRVPGAAHHADSLYTYC
4. CTVRVPGAAHHADSLYTC
5. CETVRVPGAAHHADSLYC
6. CYETVRVPGAAHHADSLC

Fig. 14A

METHOD FOR SELECTING A CANDIDATE DRUG COMPOUND

CROSS-REFERENCE TO RELATED APPLICATIONS

This application is a divisional of co-pending U.S. patent application Ser. No. 11/213,443, filed Aug. 26, 2005, which application is a continuation of PCT International Application No. PCT/NL2004/000146, filed on Feb. 26, 2004, designating the United States of America, and published, in English, as PCT International Publication No. WO 2004/077062 A2 on Sep. 10, 2004, which application claims priority to European Patent Application Serial No. 03075597.9, filed Feb. 27, 2003, the contents of the entirety of each of which are incorporated herein by this reference.

TECHNICAL FIELD

This disclosure relates generally to biotechnology. In one embodiment, it relates to the field of candidate drug testing and drug development. In another aspect, it relates to methods for attaching a molecule to a scaffold, such as preparing cyclic peptides and peptidomimetics and to cyclic peptides or peptidomimetics for use in, among other things, drug-screening programs and the diagnosis and/or treatment of disease. In other embodiments, it relates to the synthesis of discontinuous or conformational binding sites or epitopes corresponding to or interacting with a binding molecule, in particular, in relation to protein-protein or protein-ligand interactions.

BACKGROUND

Interactions between binding molecules, which in general are biomolecules, and their corresponding ligands, are central to life. Cells often bear or contain receptor molecules that interact or bind with a hormone, a peptide, a drug, an antigen, an effector molecule or with another receptor molecule. Enzymes bind with their substrate. Antibody molecules bind with an antigen, nucleic acid with protein, and so on. By "interact or bind" it is meant that the binding molecule and ligand approach each other within the range of molecular forces and may influence each others' properties. This approach takes the binding molecule and its ligand through various stages of molecular recognition comprising increasing degrees of intimacy and mutual effect: they bind, albeit not always irreversibly. Interactions between binding molecules are widely and extensively tested in the field of candidate drug testing, with the ultimate goal to find specific drugs that can interact or bind with specific target molecules in the body that mediate or modulate the development of disease.

Binding molecules have binding ability because they comprise distinct binding sites allowing for the recognition of the ligand in question. The ligand, in turn, has a corresponding binding site and only when the two binding sites can interact by essentially spatial complementarity, the two molecules can bind. Needless to say that, molecules having three dimensions, binding sites are of a three-dimensional nature, often one or more surface projections or protuberances of one binding site correspond to one or more pockets or depressions in the other, a three-dimensional lock-and-key arrangement, sometimes in an induced-fit variety. Sometimes, such a protuberance comprises a single loop of the molecule in question and it is only this protuberance that essentially forms the binding site. In that case, one often terms these binding sites as comprising a linear or continuous binding site, wherein a mere linear part of the molecule in question is in essence responsible for the binding interaction. This terminology is widely used to describe, for example, antibody-antigen reactions wherein the antigen comprises part of a protein sequence, a linear peptide. One then often speaks about a linear or continuous epitope, wherein the binding site (epitope) of the antigenic molecule is formed by a loop of consecutively bound amino acids. However, similar continuous binding sites (herein, "epitope" and "binding site" are used interchangeably) can be found with receptor-antigen interactions (such as with a T-cell receptor), with receptor-ligand interactions such as with hormone receptors and agonists or antagonists thereof, with receptor-cytokine interactions or with for example enzyme-substrate or receptor-drug interactions, wherein a linear part of the molecule is recognized as the binding site, and so on. More often, however, such a protuberance or protuberances and depressions comprise various, distinct parts of the molecule in question, and it is the combined parts that essentially form the binding site. Commonly, one names such a binding site comprising distinct parts of the molecule in question a discontinuous or conformational binding site or epitope. For example, binding sites laying on proteins having not only a primary structure (the amino acid sequence of the protein molecule), but also secondary and tertiary structure (the folding of the molecule into alpha-helices or beta-sheets and its overall shape), and sometimes even quaternary structure (the interaction with other protein molecules), may comprise in their essential protuberances or depressions amino acids or short peptide sequences that lay far apart in the primary structure but are folded closely together in the binding site. In linear (continuous) binding sites, the key amino acids mediating the contacts with the antibody are typically located within one part of the primary structure usually not greater than 15 amino acids in length. Peptides covering these sequences have affinities to the target proteins that are roughly within the range shown by the intact protein ligand.

In conformational (discontinuous) binding sites, the key residues are in general distributed over two or more binding regions, which are often separated in the primary structure. Upon folding, these binding regions can be brought together on the protein surface to form a composite binding site. Even if the complete binding site mediates a high affinity interaction, peptides covering only one binding region, as synthesized in a linear scan of overlapping peptides, generally have very low affinities that often cannot be measured, for example, in normal ELISA or Biacore experiments.

The discovery of the physiological role of a great number of peptides stimulated researchers all over the world towards design and synthesis of peptidomimetics (or peptide-like molecules) as candidate drugs or diagnostic tools. Since natural peptides seldom can be used therapeutically as drugs because of the problems associated with low absorption, rapid metabolism and low oral bioavailability, many efforts aimed to modify the natural sequence of the amino acids of bioactive peptides achieved a desired, very focused effect. Modern biochemical techniques have identified a large number of peptides having potent pharmacological activities. However, since peptides are not usually orally active and suffer from short half lives in vivo, their direct utilization as drugs is not generally feasible. In addition, the interactions of many peptides with their macromolecular targets (receptors, enzymes, antibodies) will depend on the adoption of a particular conformation. Accordingly, the design of conformationally restricted peptides and the partial replacement of peptides with bioisosteric units mimicking these peptide-binding sites have become contemporary goals of medicinal chemistry. Synthetic non-natural peptides (or pseudopeptides or peptidomimetics) have the advantage of providing new functionalities that can circumvent natural processes in the body. For example, they become able to perform functions that are not available with the natural materials, such as binding to and penetrating cell membranes and resisting degradation by enzymes.

Candidate drug testing is these days often performed on a high-throughput scale, wherein arrays of candidate compounds, such as libraries of peptides or nucleic acid molecules attached to solid supports are contacted with target molecules that are thought to be relevant to one or more aspects of a disease under study. Binding of such a target molecule to such a candidate compound is then seen as a possible hit or lead towards the identification of a binding site of the target molecule and, simultaneously, towards the identification of a candidate compound, from among the many different compounds present on the array, having a binding site that, more or less, bears relevance for interaction with the target molecule. However, having identified a lead compound in no way means that one has selected a definite drug compound suitable for interaction with the target molecule. For one, the binding site identified may only partly fit or be relevant for the molecule in question, and several rounds of modification may be required before a better fit, and thus a more appropriate binding site, has been identified. Also, considering that all the testing so far has been done in an array format, or at least with molecules attached to a solid support only, no attention has yet been given to the fact that a drug needs to be administered in solution, away from the solid support on which its lead was identified. As molecules often change or behave quite differently in solutions, having lost the specific constraints when attached to a solid phase, many promising lead compounds actually lose their attraction as a candidate drug when tested for the interaction with their target molecule in solution, again necessitating various rounds of modification before their candidacy as a drug may become further established.

Mimicking binding sites of complex proteins, e.g. TNF-alpha, the CD (cluster of differentiation antigen)-family, cytokines, or protein binding sites, like antibodies or cell surface receptors, by means of synthetic peptides or equivalent bioisosteric units is currently one of the most active areas in protein science and drug development. Many proteins exert their biological activity through interactions involving relatively small regions of their exposed surfaces. Molecules that mimic these surface epitopes are, therefore, of great interest, since they may provide a means of mimicking the biological activity of the entire protein in a relatively small synthetic molecule. Short linear peptides are not ideal for this purpose because of their inherent flexibility and susceptibility to proteolytic degradation. Instead, it is preferred to constrain linear peptide chains by cyclization into biologically relevant secondary structures. Thus, the challenge for the development of successful binders is primarily related to fixing the essential peptide sequence in the correct conformation and orientation on a platform or scaffold. The conformational rigidification of a single linear peptide, like backbone or side-chain cyclization strategies, has given rise to numerous cyclopeptides with subnanomolar activities. Various procedures to obtain such monocyclic peptides are fairly well worked out and procedures for their synthesis are also available. Various efficient synthetic routes to scaffolds for preparing monocyclic peptides have been developed, along with methods for their incorporation into peptidomimetics using solid-phase peptide synthesis. Among the various approaches utilized for preparing monocyclic peptides, several employed peptides containing pairs of cysteine residues allowing subsequent cyclization via disulfide bond formation (see, for example, U.S. Pat. No. 3,929,758; U.S. Pat. No. 4,518,711; U.S. Pat. No. 5,216,124; U.S. Pat. No. 5,169,833; WO9109051; and WO9108759).

In sharp contrast, the synthesis of scaffold-bound peptidomimetics with multiple peptides or peptide segments, for example, for mimicking discontinuous epitopes or binding sites, has been facing long-standing technical difficulties. Not only multiple peptides or peptide segments need to be fixed on a molecular scaffold or scaffolds but typically they have to be captured in a structurally coordinated fashion to be effective as a binding partner. Numerous efforts have been devoted to the synthesis of conformationally constrained peptide constructs consisting of multiple looped peptide segments. However, only a few examples exist in which the conformational fixation of multiple constraint peptide loops on a (synthetic) platform is achieved. A major problem is that suitable chemistry is far from straightforward. Current approaches essentially always require multiple protection/deprotection schemes in order to couple more than one different peptide or peptide segment onto a functionalized scaffold molecule in a controlled fashion. A functionalized scaffold molecule refers to a molecule serving as a scaffold or scaffold for another molecule wherein the scaffold is provided with multiple, usually different, functional groups via which the other molecules can be attached. For example, binding of a peptide via its N-terminal amino group to a functionalized scaffold or scaffold requires protection of all amino acid side chains also containing a reactive amino group, like lysine or arginine residues, in order to prevent unwanted coupling of such a side chain to a scaffold. Likewise, acidic amino acids need to be protected when using a coupling procedure via the C-terminal carboxyl group of a synthetic peptide. Following completion of a product, further deprotection or cleavage steps have to be performed because the side chain protection groups must be removed to recover the original amino acids. Frequently, depending on the nature of a protective group, the removal of each type of protective group requires a different protocol involving, for example, different buffers, solvents and chemicals. As a consequence, a long and tedious course of action is required to be able to isolate the desired product in measurable quantities when using procedures available thus far. Furthermore, an additional problem when working with purely synthetic scaffolds is the required selective functionalization, which ultimately leads to multistep procedures, often with disappointingly low yields.

SUMMARY OF THE INVENTION

In certain embodiments, provided are methods for selecting a candidate drug compound from among a library of compounds wherein binding of a target molecule, and optionally the effect of the binding, is determined with the candidate compound bound to a solid support and, optionally, also may be determined with the candidate compound not bound to a solid support, for example, in solution, in a bioassay, in an animal experiment, and such that may be of interest to determine effects of binding to the target molecule, such as a receptor or antibody molecule under study.

Such methods allow for testing candidate compounds under different conditions, bypassing the fact that most molecules essentially change or behave quite differently in solutions, having lost the specific constraints when attached to a solid phase. Now lead compounds may be detected that may not actually lose their attraction as a candidate drug when tested for the interaction with their target molecule in solution, thereby omitting or reducing the need for various rounds of modification before their candidacy as a drug may become further established. Such methods as provided herein comprise selecting the candidate compound from among compounds composed of an invariant scaffold molecule to which a variant potential binding site molecule is linked. By selecting an invariant scaffold molecule and allowing for testing variant binding sites or molecules attached to the scaffold, the method as provided herein remains the attractive flexibility of combinatorial chemistry. On the other hand, however, provided is such scaffold with binding sites attached that are of a relatively constrained nature, the binding sites behave similarly when tested on a solid support as tested, for example, in solution.

DETAILED DESCRIPTION OF THE PREFERRED EMBODIMENTS

Figure 1:
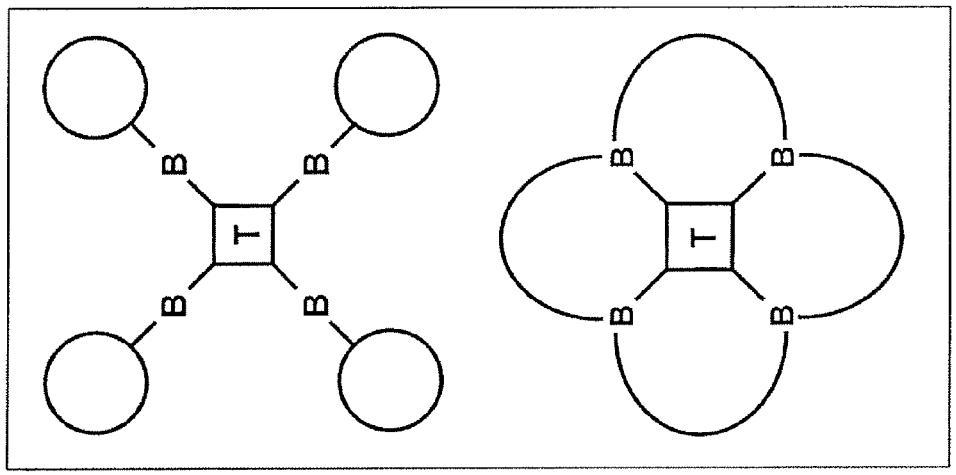
FIG. 1: Outline of classical and novel approach for the synthesis of multiple peptide loops on synthetic scaffolds. The classical approach requires multiple protection-deprotection steps in order to couple three different cyclopeptides onto a single scaffold molecule, which makes the procedure long and tedious. Our new strategy circumvents this problem by reacting a linear peptide with the correct number of functionalities B with a symmetrically functionalized scaffold with an equal number of functionalities A, giving in essence exclusively the 1:1 product in very high yields.
Figure 1:
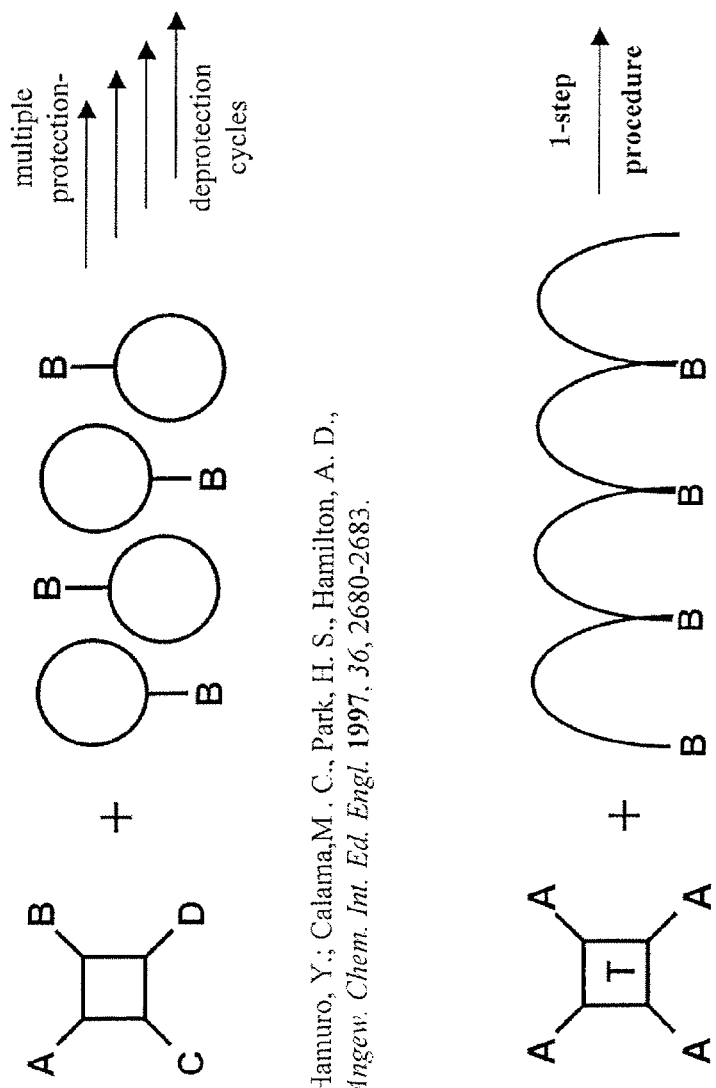
Figure 2:
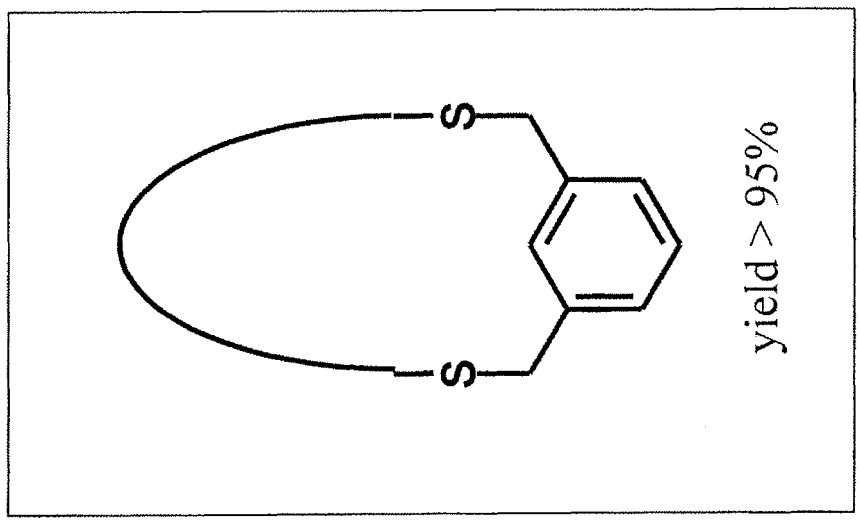
FIG. 2: Coupling reaction of SH—SH peptides with dibromobenzene scaffold.
Figure 2:
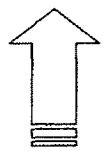
Figure 2:
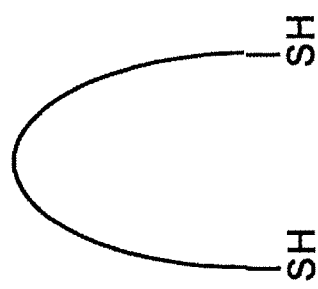
Figure 2:
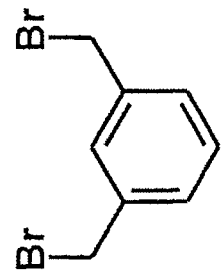

Preferably, binding of the target molecule with the candidate compound is determined on an array provided with a library of compounds composed of invariant scaffolds and variant binding sites, allowing rapid selection of promising leads from among many test compounds at once. It is preferred that the scaffold molecule is linked via at least two linkages to the potential binding site molecule, for more constraint and thus essential similarity of binding sites tested bound or free from a solid support, such as in the array and in solution.

In a certain embodiment, provided is a method comprising selecting an invariant scaffold molecule with at least a first and a second reactive group and providing at least one potential binding site molecule capable of reacting with at least a first and second reactive group, as further detailed below. The at least first and second reactive groups may be identical. The invention is applicable to potential binding site molecules of a varied nature, such as nucleic acid molecules or carbohydrates. However, it is preferred that the potential binding site molecule is mainly of peptidic nature. For ease of linkage, the potential binding site molecule may comprise a SH-functionalized peptide, and it is even preferred that at least one linkage between scaffold and binding site molecule comprises a thioether linkage.

In another embodiment, the invariant scaffold molecule comprises a (hetero)aromatic compound, in particular with at least two benzylic halogen substituents, such as a halomethylarene, in particular a bis(bromomethyl)benzene, a tris(bromomethyl)benzene, a tetra(bromomethyl)benzene or a derivative thereof. The invention also provides a pharmaceutical composition comprising a drug compound selected by a method hereof. Furthermore, provided is a composition comprising at least one scaffold molecule linked to at least one binding site molecule wherein the scaffold molecule comprises a (hetero)aromatic compound. It is preferred that the scaffold molecule is derivable from a halomethylarene, such as a bis(bromomethyl)benzene, a tris(bromomethyl)benzene, a tetra(bromomethyl)benzene or a derivative thereof. However, nonaromatic scaffolds provided with at least two reactive groups may also be used. As described herein, it is preferred that the potential binding site molecule is mainly of peptidic nature, such as an SH-functionalized peptide. Preferably, the composition comprises at least one scaffold molecule that is linked to at least one binding site molecule with at least one thioether linkage. Such a compound is useful in a method for selecting a candidate drug compound.

In certain embodiments, provided is a method for selecting a suitable candidate drug compound, for example, a compound capable of binding with a target molecule such as an antibody, a receptor, or other desired binding molecule, from among a library of compounds wherein binding of the target molecule with the candidate compound is, preferably first, determined on a solid support provided with the candidate compound or, preferably, on an array provided with the library of compounds and also is determined with the candidate compound not bound to a solid support, the method comprising selecting the candidate compound from among compounds composed of an invariant scaffold molecule to which a variant potential binding site molecule is linked, preferably via at least two linkages, the link allowing presentation of the potential binding site in a constrained fashion, allowing the interaction of the binding site with the target molecule in an essentially similar fashion, be it when the compound is present on a solid support or not, such as in solution, or at least free from the solid support such as in a bioassay.

While others in the field focused primarily on improving existing methods, be it essentially in vain, the inventors hereof walked off the beaten track and took a fresh view on the matter. For one, provided is a simple and straightforward method for attaching at least one potential binding site molecule via at least two linkages to a molecular scaffold, the method comprising providing a scaffold comprising at least a first and a second reactive group, providing at least one (potential binding site) molecule capable of reacting with at least the first and second reactive groups, contacting the scaffold with at least one molecule under conditions allowing molecule to react with at least the first and second reactive groups to form at least two linkages between the scaffold and at least one molecule in a coupling reaction, wherein the formation of a first linkage accelerates the formation of a consecutive linkage.

In one embodiment, a method is provided for the synthesis of conformationally constrained molecular loop constructs consisting of one or more looped molecular segments. Also provided is a method for the surface attachment of one or multiple loops on activated surfaces in a structurally controlled fashion.

In one embodiment, a method is provided for the synthesis of conformationally constrained peptide constructs consisting of one or more looped peptide segments. Surprisingly, the method provided can be used on essentially unprotected peptides and does not require any degree of selective functionalization of the scaffold used. This novel strategy, which is unparalleled by any existing method, satisfies a long-felt need of people in various areas, ranging from protein and peptide chemistry to medicinal chemistry and drug development.

As said, provided is a method for attaching at least one binding site molecule via at least two linkages to a scaffold or scaffold. According to a method provided, the formation of a first linkage between a scaffold and a molecule influences the reactivity of at least the second reactive group such that the formation of a consecutive linkage is accelerated. Thus, in a method provided the first linkage accelerates or enhances consecutive (second, third, etc.) linkage formation. In other words, the attachment of a molecule to a scaffold with a method as provided herein takes place in a rapid, concerted process comprising a cascade of reactions. For example, the formation of a first linkage, also referred to as a (chemical) bond or connection, via a first reactive group increases the reactivity of a second reactive group, and so on, such that the activating effect is being "handed over" from one reactive group to the next one. The chemical reactions involve changes at functional groups while the molecular skeleton of the scaffold remains essentially unchanged. For example, a "scaffold molecule," as used herein, provided with at least two reactive groups reacts with at least one molecule such that the reactive groups of a scaffold become involved in the new linkages with the molecule attached while the core structure or skeleton of the scaffold does not participate directly in the coupling. Depending on the type of chemical reaction, the reactivity of a reactive group can be enhanced by various means. Generally speaking, a chemical reaction is a sequence of bond-forming and bond-breaking steps, typically involving bonding and non-bonding electrons. At the molecular level, the essence of the chemical reaction is charge attraction and electron movement. The largest group of reactions can be regarded as ionic reactions because their reactants are electron-rich or electron-poor. In such a reaction, an electron-rich reactant, also called nucleophile, shares an electron pair with an electron-poor reactant, known as electrophile, in the process of bond formation. The reactivity of a reactant, such as a reactive group on a scaffold, is enhanced by increasing its electronic character. For example, if a reactive group participates in a coupling reaction as a nucleophile, its nucleophilicity is increased by an electron-rich or electron-donating group or atom present in the molecular scaffold entity. Likewise, the electrophilic character of a reactive group is increased by an electron-poor or electron-withdrawing group or atom within the scaffold. Such a group or molecule can be situated in direct vicinity of a reactive group as well as at some distance from a reactive group, for instance, in the molecular skeleton of the scaffold. A molecular entity is any constitutionally or isotropically distinct atom, molecule, ion, ion pair, radical, radical ion, complex, conformer etc., identifiable as a separately distinguishable entity. For instance, it comprises a scaffold without a molecule attached to it, or a scaffold with a molecule attached to it via a first linkage.

In one embodiment, the formation of a first linkage between an invariant scaffold and a potential binding site molecule accelerates the formation of consecutive linkages via the so-called neighboring group effect or intramolecular catalytic effect. Intramolecular catalysis refers to the acceleration of a chemical transformation at one site of a molecular entity through the involvement of another functional ("catalytic") group in the same molecular entity, without that group appearing to have undergone a change in the reaction product. Intramolecular catalysis can be detected and expressed in quantitative form by a comparison of the reaction rate with that of a comparable model compound in which the catalytic group is absent or by measurement of the effective molarity of the catalytic group. The term "effective molarity" (or "effective concentration") refers to the ratio of the first-order rate constant of an intramolecular reaction involving two functional groups within the same molecular entity to the second-order rate constant of an analogous intermolecular elementary reaction. This ratio has the dimension of concentration. The term can also apply to an equilibrium constant.

In one embodiment hereof, an essentially linear binding site molecule is attached to a scaffold via at least two linkages which typically results in the formation of a looped or cyclic structure attached to the scaffold. Binding site molecules of various nature can be used in a method provided. For example, biomolecules as well as synthetic molecules can be used including molecules of mainly peptidic nature, such as peptides or peptidomimetics or molecules that are based on fatty acids. A peptidomimetic is a compound containing non-peptidic structural elements that is capable of mimicking or antagonizing the biological action(s) of a natural parent peptide. A peptidomimetic no longer has all the classical peptide characteristics, such as enzymatically scissille peptidic bonds.

Provided is a method for attaching synthetic non-natural peptides, or pseudopeptides to a molecular scaffold or scaffold in a rapid and efficient manner. Also provided is a method to attach or constrain natural peptide sequences, the method comprising a modification, for example, a peptide comprising a bioisosteric replacement, to an invariant scaffold. A bioisostere comprises a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. But, as said, a binding site molecule for use in a method provided herein also comprises a peptide per se.

In one embodiment, a method is provided for providing a scaffold with at least one looped peptide structure, the method comprising providing a scaffold comprising at least a first and a second reactive group, providing at least one peptide capable of reacting with at least the first and second reactive groups, contacting the scaffold with at least one peptide under conditions that allow the formation of at least two linkages between the scaffold and at least one peptide in a coupling reaction, wherein the formation of a first linkage accelerates, or promotes, the formation of a consecutive linkage to form a scaffold provided with at least one looped peptide structure.

In a method provided for obtaining a compound composed of a scaffold with at least one looped peptide structure in a simple and rapid fashion, a peptide can be a linear peptide or a peptidomimetic, including peptides containing one or more cyclic stretches, or a peptide molecule with one or more non-peptidic bonds. Typically, a peptide molecule for use in a method provided is a synthetic peptide, for instance, obtained using standard peptide synthesis procedures. Synthetic peptides can be obtained using various procedures known in the art. These include solid phase peptide synthesis (SPPS) and solution phase organic synthesis (SPOS) technologies. SPPS is a quick and easy approach to synthesize peptides and small proteins. The C-terminal amino acid is, for instance, attached to a cross-linked polystyrene resin via an acid labile bond with a linker molecule. This resin is insoluble in the solvents used for synthesis, making it relatively simple and fast to wash away excess reagents and by-products. Suitable peptides comprise peptides of various lengths. As is exemplified herein, oligopeptides ranging from as small as 3 amino acids in length to polypeptides of 27 residues have been successfully used in a method provided. The maximal length or size of a suitable peptide or peptidomimetic essentially depends on the length or size that can be achieved using peptide synthesis. In general, peptides of up to 30 amino acid residues can be synthesized without major problems.

A preferred example of the invention relates to a variety of (linear) peptides with two free cysteine thiols that react rapidly with a variety of bis(bromomethyl)benzenes as scaffolds or scaffold molecules.

In one embodiment, a synthetic scaffold comprising at least two identical reactive groups is used to couple one or more potential binding site molecules, for example, peptides or peptide fragments, to the scaffold. Suitable molecules for use in a method provided comprise all possible molecules capable of reacting with at least two reactive groups on a scaffold to form at least two linkages or bonds between the molecule and the scaffold, which typically results in a looped or cyclic molecular segment or structure on a scaffold. Speaking in terms of organic chemistry, the essence of such a bond formation is charge attraction and electron movement.

In one embodiment, the coupling reaction between a variant binding site molecule and an invariant scaffold molecule involves a nucleophilic substitution reaction wherein a molecule with a free nucleophilic functionality reacts with a scaffold. A nucleophile typically shares an electron pair with an electrophile in the process of bond formation. In other words, a nucleophile is seeking a center of electron deficiency (an atom) with which to react. Nucleophiles ("nucleus-loving") can be charged or uncharged and include, for example, heteroatoms other than carbon bearing a lone pair, or pi electrons in any alkene or alkyne. Electrophiles ("electron-loving") are electrically neutral or positively charged and have some place for the electrons to go, be it an empty orbital (as in $BH_3$) or a potentially empty orbital.

In one embodiment, as is exemplified in the detailed description, the nucleophilic functionality comprises a thiol or sulfhydryl group. Thiols are effective nucleophiles for substitution at saturated carbon atoms. It is, in general, not difficult to provide a molecule with a nucleophilic functionality. For example, a peptide or peptidomimetic is easily functionalized with a thiol moiety by incorporating a cysteine residue in the peptide amino acid sequence. For example, the linear peptide Ac-CVYETVRVPGSAGGADSLYTYP-VATQC-NH$_2$ (SEQ ID NO:1) reacts with the dibromo-scaffold 1,3-bis(bromomethyl)benzene in an aqueous buffer.

In one embodiment, a method is provided for attaching at least one molecule to a scaffold via the formation of at least two linkages in a coupling reaction, wherein the coupling reaction is performed in solution. In another example, the peptide Ac-AHHPDTIVTCPEATQCHCGK-NH$_2$ (SEQ ID NO:2) reacts with three reactive groups of the molecular scaffold 1,3,5-tris(bromomethyl)mesitylene to form three linkages with the scaffold. In yet another example, the synthetic peptides Ac-CVYETVRVPGSAGGADSLYTYP-VATQC-NH$_2$ (SEQ ID NO:1) and Ac-CRGDLQC-NH$_2$ (SEQ ID NO:3) each react with two reactive halomethyl groups of the tetrahalo molecular scaffold 1,2,4,5-tetra(bromomethyl)benzene. Of course, various other nucleophilic functionalities, like amino acids with an alcohol (—OH) or an amine (—NH) moiety, can be similarly incorporated into a binding site molecule. However, it should be emphasized that the chemistry required for the coupling reaction of an alcohol or amine in general does not allow the use of unprotected molecules, in contrast to a method provided using SH-functionalized molecules. A coupling reaction according to the invention runs without problems for virtually all possible peptides having at least two free cysteine sulfhydryl groups. The reaction is fully compatible with unprotected amine (K), amido (QN), arginine (B), carboxylic acid (DE), alcohol (ST), thioether (M), imidazol (H), phenyl (F), phenol (Y), indole (W), and aliphatic (AVILP) functionalities. Thus, a method provided allows the use of an unprotected peptide wherein none of the amino acid side chains are protected or treated otherwise to prevent unwanted participation in the coupling reaction. Thus, a method is provided for attaching at least one variant binding site molecule to a scaffold via at least two linkages, wherein the molecule is essentially unprotected. Importantly, a method provided herein using an unprotected peptide saves costly time, effort and money because it does not require multistep protection/deprotection steps.

The only functionality that cannot be present in unprotected form is the cysteine SH, as it is an integral part of the coupling reaction. In one embodiment hereof, a peptide is used which, besides an N- and C-terminal free cysteine, comprises one or more additional cysteine (Cys) residues. To prevent the unwanted participation of these additional Cys thiol groups in the coupling reaction, a simple approach is to use Boc-Cys(StBu)-OH (Boc-S-tert-butylmercapto-L-cysteine) for introduction of the protected Cys residue during the course of peptide synthesis. The StBu group is not removed during the course of the normal TFA deprotection-cleavage reaction, but requires reductive treatment with BME (excess) or 1,4-DTT (excess) to give the reduced sulfhydryl form of the peptide, which can either be used directly or subsequently oxidized to the corresponding cystinyl peptide.

Figure 11A:
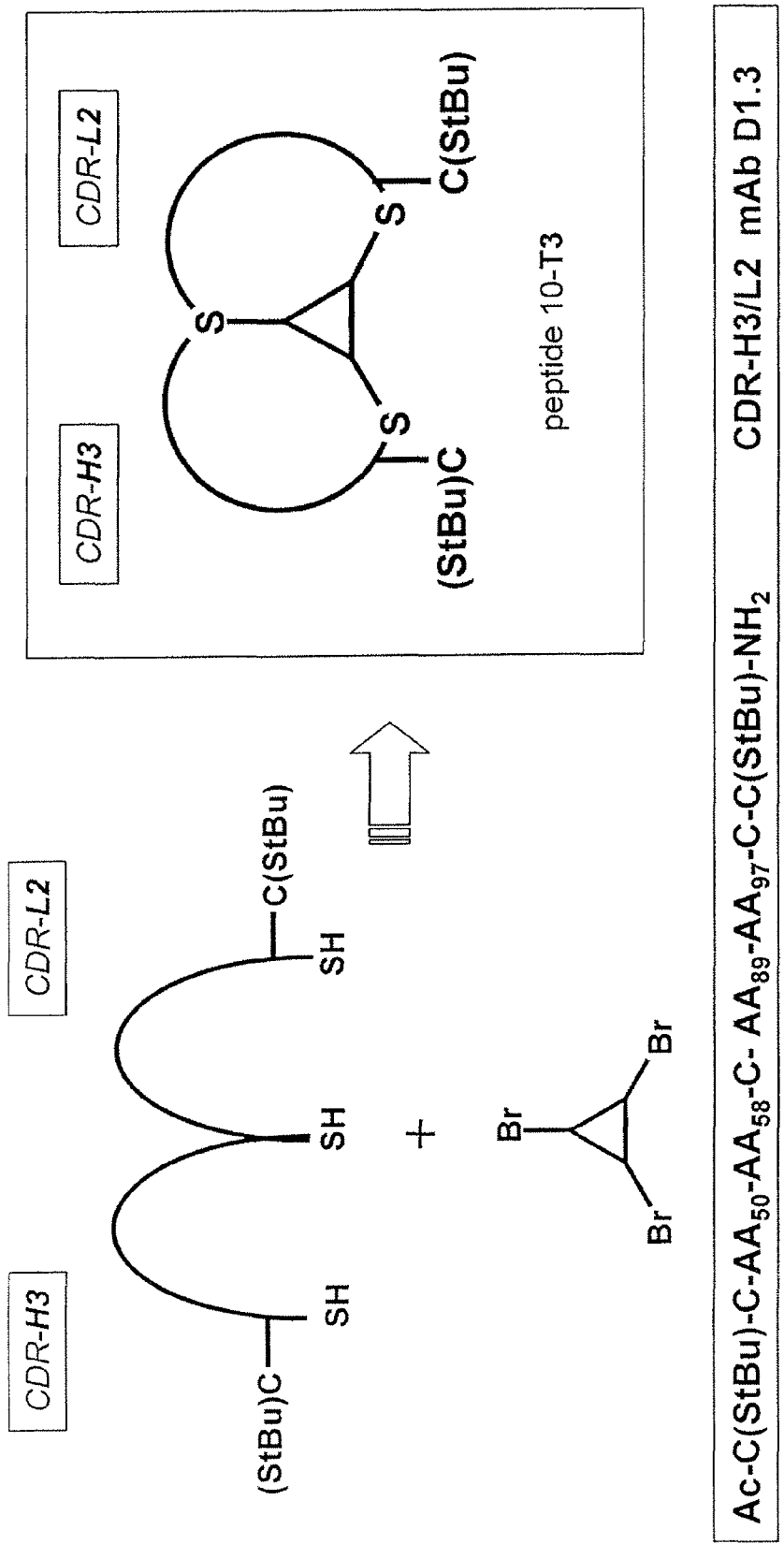
FIG. 11: Schematic representation of the synthesis of multiple CDR-loops on a synthetic scaffold for the mimicry of antibodies ($3^{rd}$ generation binding bodies).
Figure 11B:
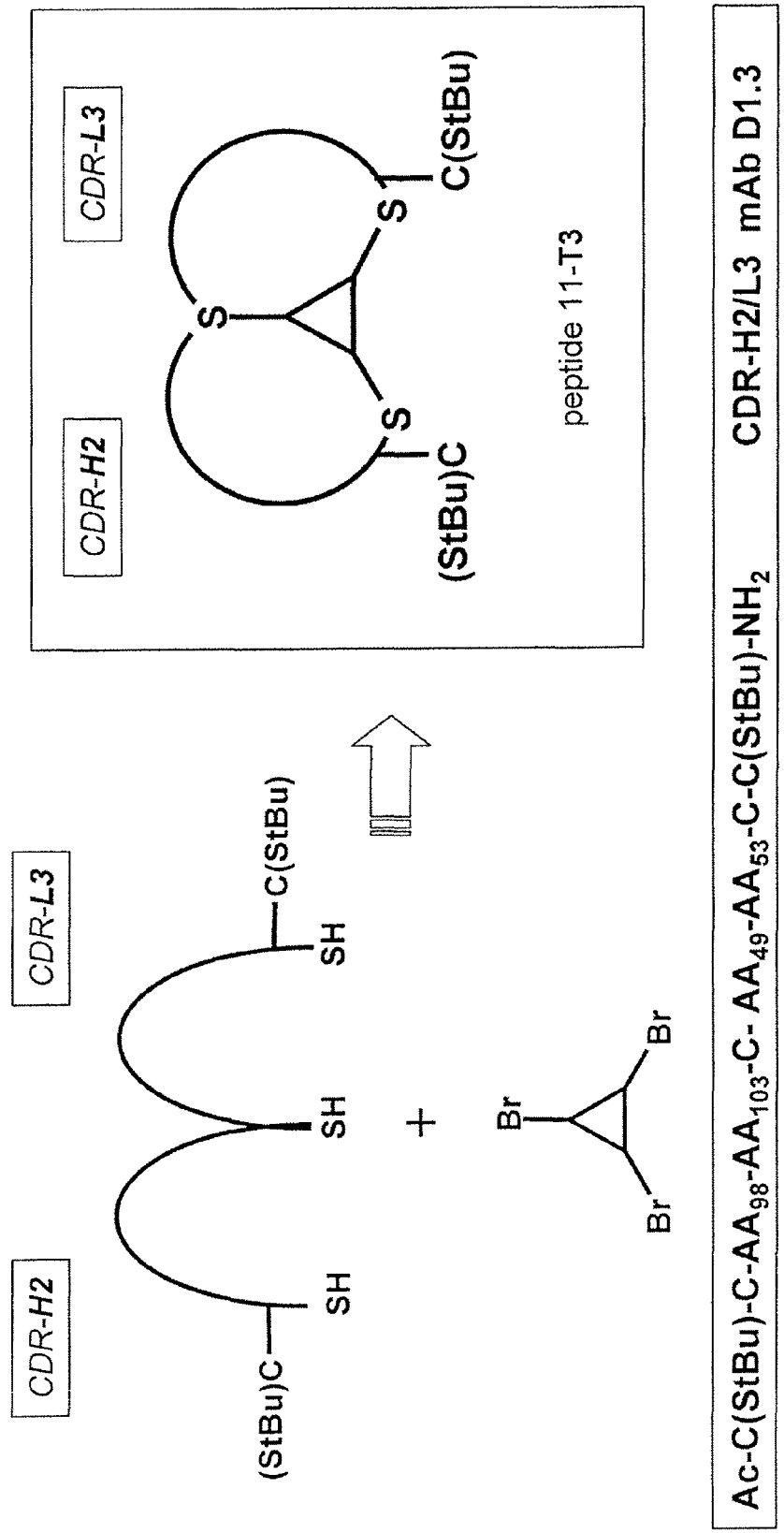
Figure 11C:
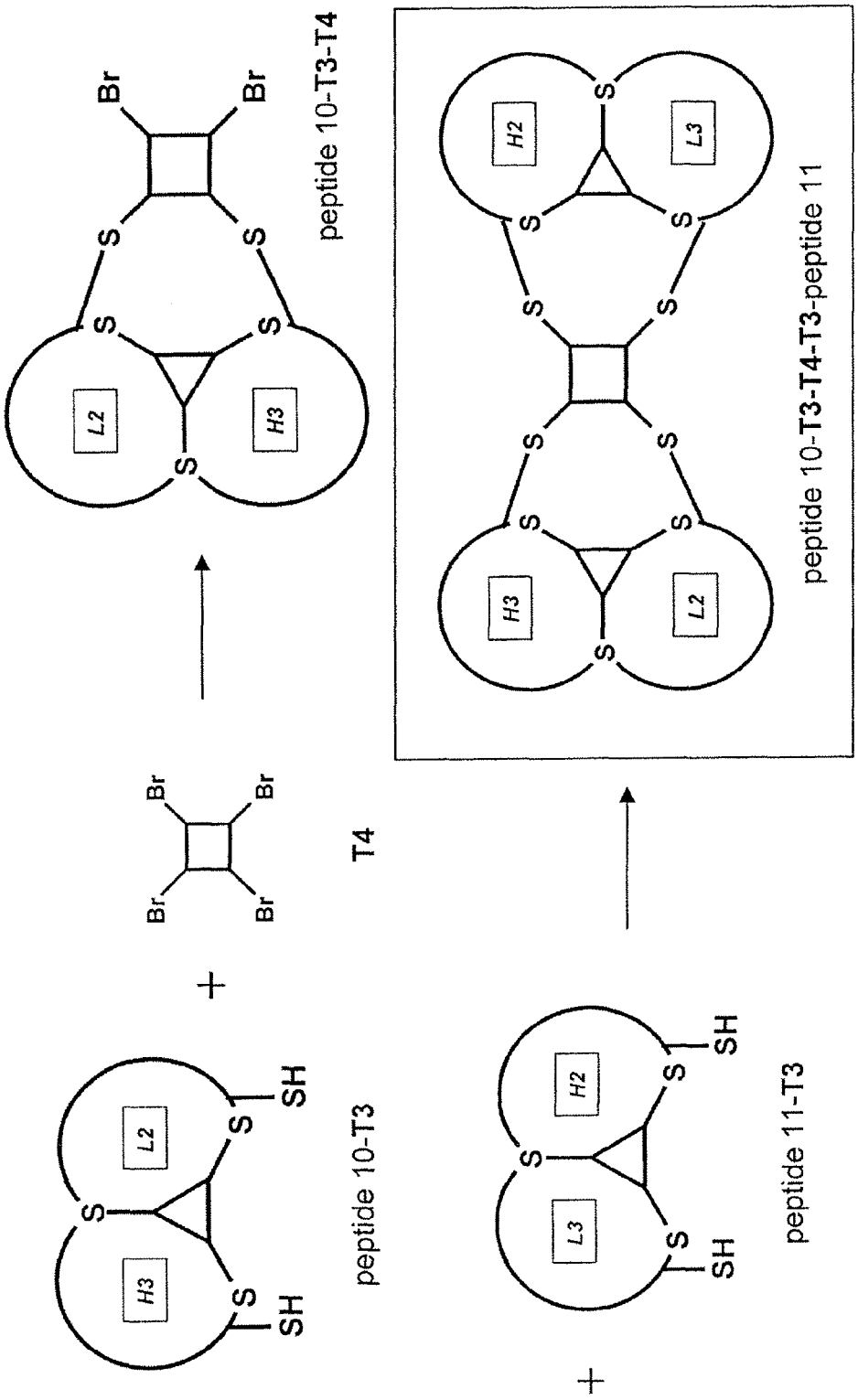

In one embodiment, a peptide is used that contains at least one Cys derivative, such as Cys(StBu), to allow selective unmasking of a Cys-thiol group. Selective unmasking of a Cys-thiol group according to the invention allows the making of the Cys-thiol group available for reacting at a desired moment, such as following completion of the synthesis of a scaffold with at least one looped peptide structure. This is very attractive for at least two reasons. For example, two linear peptides, peptide A and peptide B, are synthesized, each comprising an unprotected Cys in the first and the last position and a Cys derivative at another position. Thereafter, the two di-SH functionalized peptides are coupled to a scaffold comprising four reactive groups, resulting in the structural fixation of two looped peptide segments on a scaffold. Subsequently, the Cys-derivatives can be unmasked by the simple addition to form an intramolecular disulfide bridge between peptides 1 and 2. In addition to the covalent bonds that connect the atoms of a single amino acid and the covalent peptide bond that links amino acids in a protein chain, covalent bonds between cysteine side chains can be important determinants of protein structure. When synthesizing a peptidomimetic compound, e.g. of a discontinuous binding site, it is especially advantageous to be able to use peptides which allow intra- or inter-peptidic disulfide bond formation. Furthermore, the use of Cys derivatives, such as Cys (StBu), permits the coupling of a looped or cyclized molecule to a multiplicity of different scaffolds, like two or three, in a structurally coordinated fashion (see also FIG. 11).

In one embodiment, a method hereof involves at least two nucleophilic substitution reactions wherein at least one potential binding site molecule, such as a peptide, having at least two free nucleophilic functionalities forms two bonds or linkages with a scaffold molecule. For instance, the peptide reacts with two or more saturated carbon atoms of a scaffold, the carbon atom being part of a reactive group. A nucleophilic substitution can also be an intermolecular process when the nucleophile and leaving group are part of a single molecule or molecular entity.

In one embodiment, a scaffold is provided with at least one molecule via at least one intramolecular nucleophilic substitution reaction. Intramolecular processes have a far more favorable entropy than the analogous intermolecular reactions because it is not necessary for two separate molecules to come together.

A common characteristic of a nucleophilic reaction that takes place on saturated carbon is that the carbon atom is almost always bonded to a heteroatom, an atom other than carbon or hydrogen. Furthermore, the heteroatom is usually more electronegative than carbon and is also the so-called leaving group (L) in the substitution reaction. The leaving group departs with the electron pair by which it was originally bonded to the carbon atom.

In one embodiment, a scaffold is used that contains at least two leaving groups in order to facilitate the formation of at least two bonds with at least one peptide. The ease with which a leaving group departs can be related to the basicity of that group; weak bases are in general good leaving groups because they are able to accommodate the electron pair effectively. The reactivity of a reactive group is largely determined by the tendency of a leaving group to depart. Another factor which has some bearing on reactivity of a reactive group is the strength of the bond between the leaving group and the carbon atom, since this bond must break if substitution is to occur.

Thus, in one embodiment, a scaffold comprising at least two reactive groups each comprising a good leaving group is used in a method hereof. Good leaving groups are in general the conjugate bases of strong acids. The most important leaving groups are the conjugate bases of acids with pKa values below 5. Particularly interesting leaving groups include halide ions such as I—, Br—, and Cl—. A carbon-halogen (C—X) bond in an alkyl halide is polarized, with a partial positive charge on the carbon and a partial negative charge on the halogen. Thus, the carbon atom is susceptible to attack by a nucleophile (a reagent that brings a pair of electrons) and the halogen leaves as the halide ion (X—), taking on the two electrons from the C—X bond.

In one embodiment, a reactive group comprises a carbon atom susceptible to attack by a nucleophile wherein the reactive group comprises a carbon-halogen bond. In one embodiment, a scaffold comprising at least two of such reactive groups is used to react with a di-SH functionalized peptide as nucleophile. Provided is a method for obtaining a scaffold with at least one looped peptide structure, the method comprising contacting the scaffold with at least one peptide wherein the scaffold comprises a halogenoalkane. Halogenoalkanes (also known as haloalkanes or alkyl halides) are compounds containing a halogen atom (fluorine, chlorine, bromine or iodine) joined to one or more carbon atoms in a chain. Provided herein are dihalo scaffolds, comprising two halogen atoms, and tri- and tetrahalo scaffolds for the synthesis of conformationally constrained compounds like, for example, peptide constructs consisting of one or more looped peptide segments. In general, a good leaving group is electronegative to polarize the carbon atom, it is stable with an extra pair of electrons once it has left, and is polarizable, to stabilize the transition state. With the exception of iodine, all of the halogens are more electronegative than carbon. Chlorine and bromine have fairly similar electronegativities and polarize the bond with the carbon fairly equally. When ionized, both are very weak bases with Br- being the weaker one of the two. Bromide ion is also more polarizable due to its larger size. Therefore, a method provided is advantageously practiced using a scaffold comprising at least two Cl atoms, more preferred, using a scaffold comprising at least one Cl atom and at least one Br atom and, even more preferred, using a scaffold comprising at least two Br atoms.

In one embodiment, a scaffold comprises an allylic system. In an allylic system, there are three carbon atoms, two of which are connected through a carbon-carbon double bond.

In one embodiment, the formation of a bond or linkage between a scaffold and a peptide occurs via an allylic substitution reaction. An allylic substitution reaction refers to a substitution reaction occurring at position 1 of an allylic system, the double bond being between positions 2 and 3. The incoming group may be attached to the same atom 1 as the leaving group, or the incoming group becomes attached at the relative position 3, with movement of the double bond from ⅔ to ½. The reaction rate of allylic substitutions is very high because the allyl cation reaction intermediate, a carbon atom bearing a positive charge attached to a doubly bonded carbon, is unusually stable. This is because an allylic cation is a resonance hybrid of two exactly equivalent structures. In either of the contributing structures, there is an empty p orbital with the pi cloud of the electron-deficient carbon. Overlap of this empty p orbital with the pi cloud of the double bond results in delocalization of the pi electrons, hereby providing electrons to the electron-deficient carbon and stabilizing the cation. Even more preferred is a scaffold comprising at least two allylic halogen atoms. Due to electron delocalization, allyl halides tend to undergo ionization very readily to produce a carbocation and a halide ion, such that breaking the carbon halide bond is rapid.

In a further embodiment hereof, a carbon-oxygen double bond (i.e., a carbonyl group) is present in a scaffold. Similarly to the allylic system, resonance structures can be formed which contribute to stabilization of a carbocation. For example, a scaffold comprises two or more reactive groups comprising the structure $C(O)—CH_2$-halogen.

Furthermore, in a nucleophilic substitution reaction, the structure of the substrate plays just as important a role as the nature of the leaving group. For example, if a nucleophile attacks the back side of the carbon, the reaction proceeds unhindered if the leaving group is bonded to a methyl, where the hydrogens leave enough surface to attack the carbon. As that carbon becomes more substituted, larger groups hinder the path the nucleophile must take to displace the leaving group. For these reasons, it is also advantageous that a scaffold comprise at least two halomethyl groups.

In one embodiment, a scaffold comprises a conjugated polyene, also known as an aromatic compound, or arene, which is provided with at least two reactive groups. An aromatic compound is flat, with cyclic clouds of delocalized pi electrons above and below the plane of the molecule. Preferably, a molecular scaffold according to the invention comprises at least two benzylic halogen substituents like, for instance, halomethyl groups. Suitable examples include, but are not limited, to di(halomethyl)benzene, tri(halomethyl) benzene or tetra(halomethyl)benzene and derivatives thereof. The advantage of a benzylic halogen substituent is mainly to be sought in the special stability associated with the resonance of conjugated polyenes known as aromatic compounds; a benzylic halogen atom has an even stronger tendency to leave a carbon on which a nucleophilic substitution reaction takes place.

Figure 4:
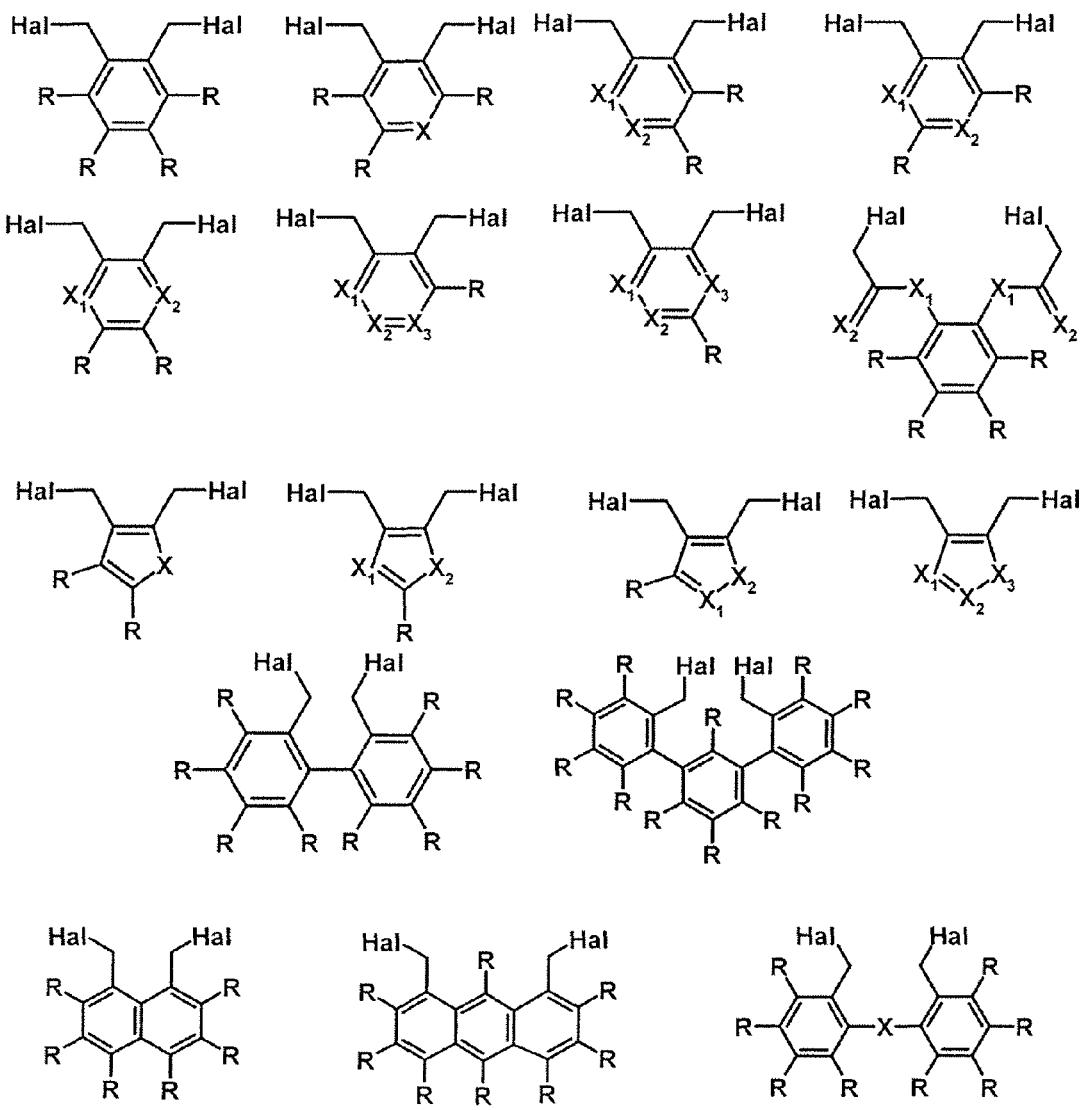
FIG. 4: Aromatic scaffolds with ortho-, meta-, or para-positioning of two halomethyl groups. "Hal" refers to chlorine, bromo, or iodine atoms. 1,2-bis(halomethyl) benzene and other regioisomers; 3,4-bis(halomethyl)pyridine (X=N) and other regioisomers; 3,4-bis(halomethyl)pyridazine (X=N) and other regioisomers; 4,5-bis(halomethyl)pyrimidine (X=N) and other regioisomers; 4,5-bis(halomethyl) pyrazine (X=N) and other regioisomers; 4,5-bis(halomethyl)-1,2,3-triazine (X=N) and other regioisomers; 5,6-bis(halomethyl)-1,2,4-triazine (X=N) and other regioisomers; 3,4-bis(halomethyl)pyrrole (X=N), -furan (X=O), -thiophene (X=S) and other regioisomers; 4,5-bis(halomethyl)imidazole (X=N,N), -oxazole (X=N,O), -thiazol (X=S) and other regioisomers; 4,5-bis(halomethyl)-3H-pyrazole (X=N,N), -isooxazole (X=N,O), -isothiazol (X=S) and other regioisomers; 1,2-bis (bromomethylcarbonylamino)benzene ($X_1$=NH, $X_2$=O); 2,2'-bis(halomethyl) biphenylene; 2,2"-bis(halomethyl)terphenylene; 1,8-bis(halomethyl)naphthalene; 1,10-bis(halomethyl)anthracene; and Bis(2-halomethylphenyl)methane.
Figure 5:
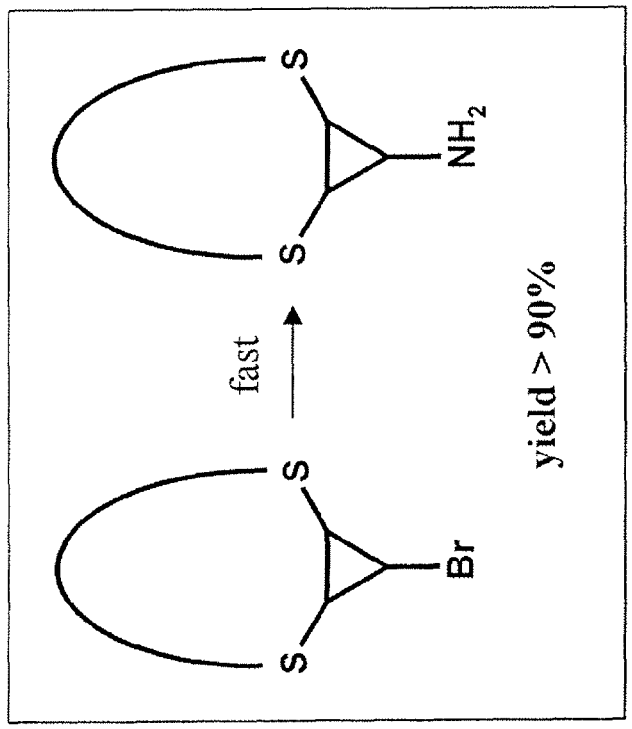
FIG. 5: Formation of looped peptide structure on a tribromo scaffold.
Figure 5:
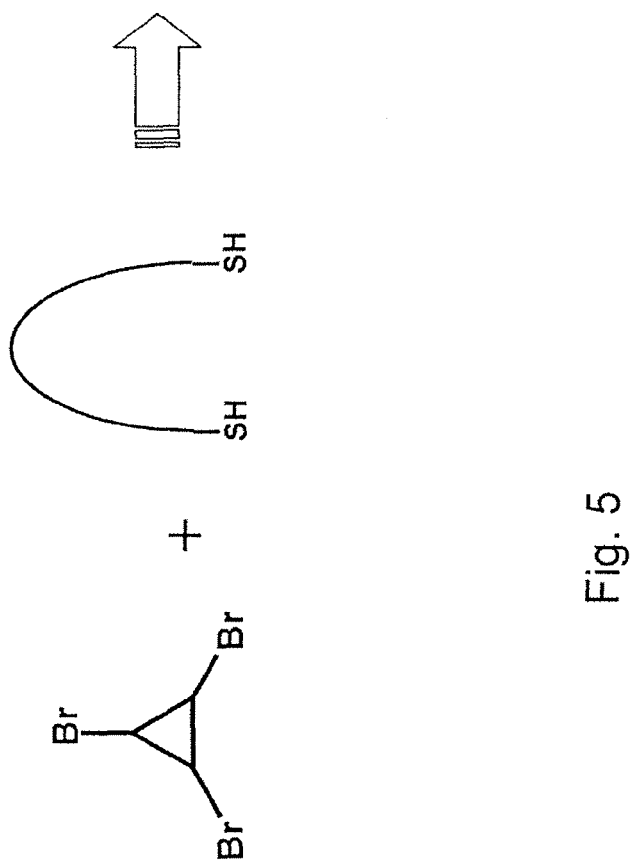

The reaction of a suitable peptide, such as SH—SH peptides, with halomethylbenzene derivatives is of very wide scope. The reaction runs successfully with a variety of aromatic compounds carrying at least two halomethyl groups. These groups can be positioned in either ortho, meta, or para position (see molecular scaffolds depicted in FIG. 4). The intramolecular catalytic effect as described above is different for each mode of coupling because para and meta-cyclophanes are generally more strained than ortho-cyclophanes. Also provided are all other (hetero)aromatic compounds with at least two halomethyl groups in ortho-, meta-, or para- position for the synthesis of a scaffold with at least one looped peptide structure. The reaction of thiols with haloalkanes and halomethylarenes is applied in different areas of chemistry and biology. However, the reaction of peptides containing two or more free cysteine sulfhydryl groups with dihaloalkanes and/or bis(halomethyl)benzene derivatives is less common. The first report in literature concerns the modification of wool (containing multiple free SH-groups) by means of reaction with $CH_2X_2$. In 1985, Mosberg was the first to use this procedure for the synthesis of a cyclic enkephalin derivative. In contrast to a method hereof, which involves a one-step coupling procedure using fully deprotected peptides in an aqueous buffer solution, the reactions reported in existing literature are performed in organic solvents via multiple protection-deprotection cycles. Later, the same procedure, generally referred to as Mosberg's procedure, was used by others for the synthesis of other enkephalin and vasopressin analogues. Recently, other scaffolds, like o-dibromo xylene, 1,4-but-2-endiyl, 1,3-pyridyl, and several naphthyl spacers, have been used for the synthesis of cyclic peptide derivatives. Also here, the reactions were performed using fully protected peptides via multiple protection-deprotection cycles and/or resulted in low yields of the cyclized peptides.

Suitable molecular scaffolds according to the invention also include polycyclic aromatic compounds with smaller or larger ring structures. However, a scaffold according to the invention is not limited to hydrocarbons. In contrast, a method provided is also suitably practiced using a heterocyclic aromatic scaffold, a cyclic molecule with at least one atom other than carbon in the ring structure, most commonly nitrogen, oxygen or sulfur. Examples include pyrrole, furan, thiophene, imidazole, oxazole, thiazole, pyrazole, -3-pyrroline, pyridine, pyrimidine and derivatives thereof. Preferred heterocyclic aromatic scaffolds include, but are not limited to, those comprising at least two halomethyl groups. A preferred scaffold is meta-dibromo-pyridine.

In another embodiment, a method provided comprises the use of a scaffold that is based on, or which consists of, multiple ring aromatic structures, such as fused-ring aromatic compounds. Two aromatic rings that share a carbon-carbon bond are said to be fused. Suitable fused-ring aromatic scaffolds include, for example, naphthalene, anthracene or phenanthrene and derivatives thereof, provided that they contain at least two reactive groups. In one embodiment, a fused-ring aromatic scaffold comprises at least two reactive groups wherein each group contains a highly reactive benzylic halogen atom, for example, a halomethyl group.

Figure 6:
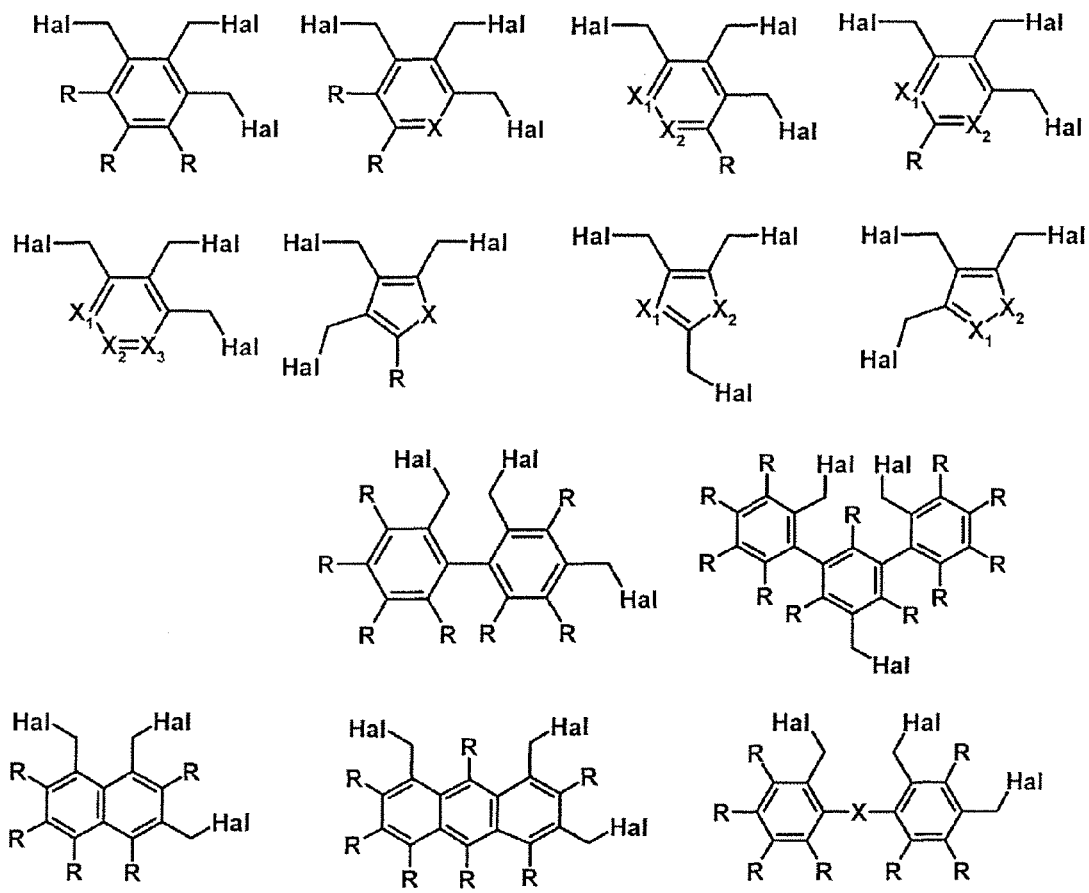
FIG. 6: Aromatic scaffolds with ortho-, meta-, or para-positioning of three halomethyl groups: 1,2,3-tris(halomethyl)benzene and other regioisomers; 2,3,4-tris (halomethyl)pyridine (X=N) and other regioisomers; 2,3,4-tris (halomethyl)pyridazine (X=N) and other regioisomers; 3,4,5-tris(halomethyl)pyrimidine (X=N) and other regioisomers; 4,5,6-tris(halomethyl)-1,2,3-triazine (X=N) and other regioisomers; 2,3,4-tris(halomethyl)pyrrole (X=N), -furan (X=O), -thiophene (X=S) and other regioisomers; 2,4,5-bis(halomethyl)imidazole (X=N,N), -oxazole (X=N,O), -thiazol (X=S) and other regioisomers; 3,4,5-bis(halomethyl)-1H-pyrazole (X=N,N), -isooxazole (X=N, O), -isothiazol (X=S) and other regioisomers; 2,4,2'-tris(halomethyl)biphenylene; 2,3',2"-tris(halomethyl)terphenylene; 1,3,8-tris(halomethyl)naphthalene; 1,3,10-tris(halomethyl) anthracene; and Bis(2-halomethylphenyl)methane.

Molecules comprising multiple aromatic or conjugated systems wherein the systems do not share a pair of carbon atoms may also be useful as a scaffold molecule. For example, a scaffold comprising a multi-ring or fused-ring structure, for instance, a scaffold wherein aromatic, e.g. benzene, rings are connected directly via a carbon-carbon bond, can be tested. Alternatively, the rings are connected via a linker comprising at least one atom. Examples of suitable scaffolds in a method of the invention are given in FIGS. 4, 6 and 8. A person skilled in the art will be able to select which versions of these molecules to test. From a commercial point of view, a scaffold according to the invention is preferably commercially available at a relatively low cost and can be obtained in large quantities. For example, the dibromo scaffold 1,3-bis(bromomethyl)benzene is currently being sold for only around 5 euro per gram.

According to the disclosure, when the reactants are mixed in a 1:1 ratio at relatively low concentrations, typically ranging between 0.1-1.0 mM, the reaction proceeds surprisingly rapidly. In one embodiment, a coupling reaction linking a variant potential binding site molecule to an invariant scaffold molecule is essentially completed in less than 60 minutes. Preferably, a reaction runs to completion even faster, such as in less than 45 or even less than 30 minutes. More preferred, a reaction according to the invention is finished within 20 minutes. Most preferred, a scaffold with at least one looped binding site molecule, such as a peptide segment, is obtained in 10 to 15 minutes. In general, the reaction rate depends on multiple parameters, such as reaction temperature and concentration of the reactants. Advantageously, a coupling reaction according to the disclosure is performed at relatively low temperatures, such as around 30° C. to 40° C. Compared to existing methods, a method provided can be performed at an economically advantageous temperature. Furthermore, a relatively low reaction temperature is also favorable for the stability of a binding site molecule. When the reactants are mixed in approximately a 1:1, or in essentially an equimolar ratio, the reaction proceeds rapidly at room temperature.

In one embodiment, a reaction is even performed at room temperature which is in general between 20° C. to 25° C. In a method provided, the desired compound can be obtained in very high yield. In one embodiment, a desired product is obtained with a yield of at least 30%. Preferably, a higher yield is obtained, such as at least 40 to 50% or even 50 to 60%. More preferred is a reaction which yields at least 70% of the candidate drug compound, such as ~75% or ~80%. Most preferred is a method provided yielding more than 85% of the desired compound, like 90% or possibly even higher. Even when a reaction is performed in the presence of a large excess (up to 20-, 50- or even a 100-fold) of molecular scaffold, only the monocyclic product is formed, together with small amounts of by-product as a result of hydrolysis and/or aminolysis of the scaffold. In one embodiment, excess of scaffold and/or possible by-products can be easily removed by means of a double washing step with an organic solvent, such as ether.

The very high efficiency of a cyclization reaction provided is exceptional when taken into account that in case of peptide 1, it involves the formation of an 88-membered ring! In general, macrocyclization reactions are known to give very poor yields (3-5% under high-dilution conditions), in particular when very large rings are formed. Among the few exceptions that are known, the Ru-catalysts ring-closing metathesis reactions (RCM) developed by Grubbs is famous as it is reversible under certain conditions.

In the present case, the high efficiency of the reaction is related to at least three factors. First of all, the high-dilution (preferably ≤0.2 mM) conditions chosen favor intramolecular reaction over intermolecular reaction, thus promoting the formation of cycles instead of polymers. Secondly, the peptide sequence that was chosen (peptide 1) is part of a β-loop structure of follicle-stimulating hormone (FSH), which means that the sequence is likely to be strongly predisposed for efficient cyclization as a result of noncovalent secondary interactions. However, also for SH—SH peptides without a noticeable predisposition of the reacting SH groups, the corresponding cyclizations also run in very high yield.

Figure 3:
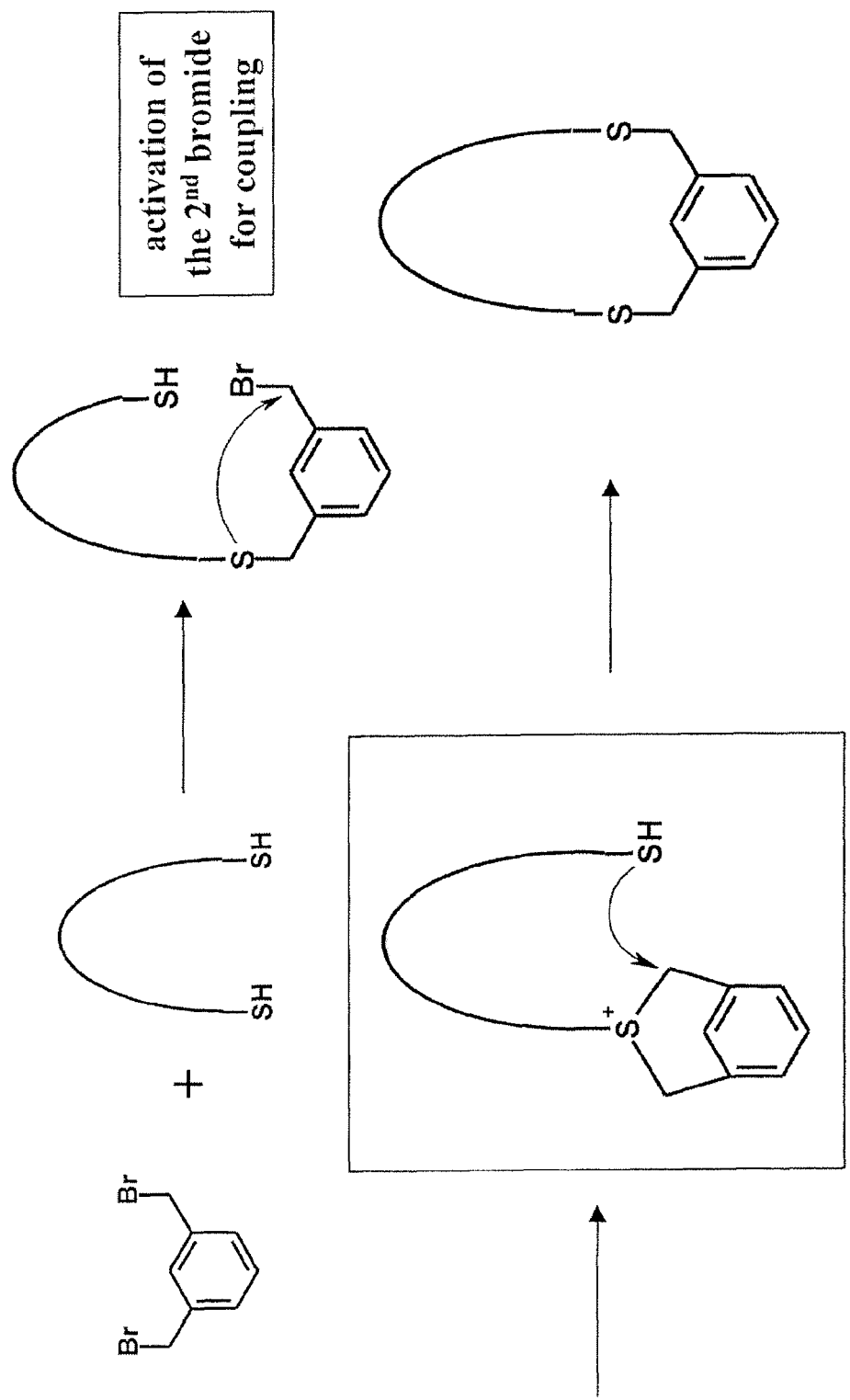
FIG. 3: Mechanism for the thioether bond formation-mediated activation of the second bromomethyl function leading to very efficient formation of the looped peptide structure.

In addition to this, the intramolecular cyclization of an SH-functionalized molecule on a scaffold is significantly accelerated by a so-called neighboring group effect, or intramolecular nucleophilic catalytic effect. The first thio-ether bond that is formed strongly activates the second reactive group for nucleophilic attack, thereby promoting intramolecular cyclization over an intermolecular reaction of the second SH-group with a second molecule of bis(halomethyl)benzene. Following formation of the first thio-ether bond, the sulfur atom is considered to function as an internal nucleophile to perform a nucleophilic attack on a second reactive halomethyl group and displace the halogen atom. A cyclic sulfonium ion intermediate is very likely to be formed. The resulting intermediate sulfonium salt is quite receptive to reaction with a nucleophile, in this particular case, a second SH-group of a molecule to be attached to a scaffold. The sulfur cation is a good leaving group and relief of strain of the ring structure can also enhance reactivity. In the example given in FIG. 3, a second SH-group reacts with the sulfonium salt intermediate in a ring-opening nucleophilic substitution to produce the final product. The overall reaction rate is essentially the rate of formation of the ring structure, an energetically favorable intramolecular process. Such involvement by an atom within the same molecule is known as neighboring group participation or anchimeric assistance.

In a method hereof, the formation of a first linkage between a variant potential binding site molecule and an invariant scaffold accelerates or promotes the formation of second linkage between a binding site molecule and a scaffold and so on. In other words, the formation of each bond or linkage creates a favorable condition for the formation of each consecutive bond. In fact, it is believed that in a method provided, the formation of a first linkage between a molecule and scaffold is the initial, rate-determining step of the coupling reaction, the subsequent fast reactions of the remaining reactive groups being energetically less demanding reactions. Thus, the observed activation further promotes cyclization over polymerization, in this way favoring high yields of the corresponding macrocycle (see FIG. 3).

From all of the above, it is evident that suitable scaffolds for practicing a method hereof are numerous and include both aromatic and non-aromatic compounds as long as intramolecular cyclization is significantly enhanced by the neighboring group effect, or intramolecular nucleophilic catalytic effect.

This type of nucleophilic catalysis has, for example, been studied for a variety of 1-halo-2-thioalkyl-substituted cyclohexanes, which react about 70,000 times faster when the substituents are oriented trans iso. cis. (Bruice, 2001). A similar type of activation in the reaction of hexakis(bromomethyl)benzene with 1.0 equivalent of 1-adamantyl carboxylic acid was recently described by Hennrich et. al., who found that only the hexasubstituted product was formed together with recovered starting material. Likewise, in a method provided, there is a cumulative activation effect wherein one reaction precipitates a series of like reactions.

A published method for the synthesis of cyclic peptides by means of sequential nucleophile substitutions on polyhalogenated aromatics includes the following steps: (i) a linear peptide or peptidomimetic with a free nucleophile functionality is reacted with the aromatic in the sense of a simple nucleophile aromatic substitution, wherein the nucleophile functionality is an alcohol, thiol or amine; (ii) the protective group of an additional nucleophile functionality is selectively split at the same peptide or peptidomimetic, wherein the released nucleophile functionality is an alcohol, thiol or amine; and (iii) cyclization is carried out by adding a tertiary amine or another base, wherein cyclization is carried out by means of nucleophilic aromatic substitution of an additional halogen atom of the halogen aromatic by the released nucleophilic functionality, the halogen aromatic being bound to the peptide.

A method according to the disclosure has several important advantages over a published method. First, where the published method relates to the use of aryl or heteroaryl halides, the present method provides, among others, alkylhalide scaffolds. Aryl halides refer to compounds in which a halogen atom is attached directly to an aromatic ring. In contrast to alkyl halides, most aryl halides are extremely unreactive. This is easily explained as follows. In the rate-determining step of nucleophilic aromatic substitution, a nucleophile attaches itself to the carbon bearing a halogen; this carbon becomes tetrahedral and the ring acquires a negative charge. Such a reaction is made more difficult by the fact that it destroys the aromaticity of the ring and disrupts the resonance between ring and halogen. In fact, the published coupling reaction only runs with di-, tri-, and tetraazines because without the nitrogen atoms in the ring, the halogen atoms would be even worse leaving groups. Thus, a method provided herein for attaching a binding site molecule to a scaffold, for example, for providing a scaffold with at least one looped or cyclic peptide, is conceptually different from the published method using aromatic substitution reactions on aryl halides. Second, intramolecular cyclization is not significantly enhanced in a published method because the scaffolds used do not allow the neighboring group effect, or intramolecular nucleophilic catalytic effect. Even more, the reactivity of an aryl halide scaffold will decrease with every substitution step. In contrast, as discussed above in detail, in a method provided the formation of a first linkage between a scaffold and a peptide accelerates or promotes the formation of a second or each consecutive linkage in the coupling or cyclization reaction. Third, where the present method permits direct coupling of unprotected peptides, the published method requires protection/deprotection of the peptide used.

In a further embodiment hereof, a method is provided for the synthesis of a candidate drug compound wherein the compound is composed of an invariant scaffold with multiple variant binding site molecules, for example, a scaffold with two or more peptides or peptide fragments. Hereto, a scaffold comprising at least three reactive groups is reacted with a binding site molecule capable of reacting with at least three reactive groups in such a manner that at least three linkages are formed between the scaffold and the molecule to form a scaffold provided with at least two looped structures.

In another embodiment, multiple looped structures are obtained using a method provided wherein a molecular scaffold or scaffold is contacted with multiple molecules, each molecule being capable of forming at least two linkages or connections with the scaffold.

In one embodiment, a method is provided for attaching multiple variant peptides, peptide-like compounds or peptidomimetics to a scaffold. This is particularly useful when, for example, synthesizing a peptidomimetic of a discontinuous epitope comprising multiple peptide segments. Scans of overlapping peptides (PepScans) are routinely used to map linear binding sites by taking the primary sequence and synthesizing appropriate 13-mers that overlap in sequence by 11 amino acids. These peptides can be synthesized on cellulose membranes that can be incubated with a solution of the target protein or ligand. Bound targets are then detected directly on the cellulose membrane, for example, using standard ELISA reactions. Two or more linear peptide fragments identified to specifically bind to a binding partner of interest in a screening procedure (for example, using Pep scan technology) can be readily immobilized on a scaffold molecule using a method provided.

It is important to emphasize a method hereof not only provides a rapid and straightforward procedure for the synthesis of candidate drug compounds comprising one invariant scaffold molecule provided with multiple potential binding site molecules, such as looped peptides, but also for the synthesis of even more complex synthetic platforms comprising, for example, multiple scaffolds and multiple attached molecules.

In one embodiment hereof, a series of coupling reactions is perfoiined, each involving the attachment of at least one binding site molecule to a scaffold. One should realize that in this embodiment of a method provided, a scaffold provided with at least one molecule in a first coupling reaction can serve as a molecule in a second coupling reaction and so on. Thus, the term molecule also comprises a molecular entity comprising at least one scaffold, provided that this molecule is capable of reacting with at least two reactive groups of another scaffold. Scaffolds used can be different from each other, but they can also be identical. As is exemplified herein (see FIG. 11), a method provided herein involving multiple coupling reactions is advantageously used for the simple and straightforward synthesis of CDR-based peptide constructs for the mimicry of antibodies.

Further provided is a method for attaching at least two binding site molecules to a scaffold wherein each molecule is attached to the scaffold via at least two linkages, the method comprising providing a scaffold comprising at least four reactive groups, providing at least two molecules each being capable of reacting with at least two reactive groups, contacting the scaffold with at least two molecules under conditions that allow the formation of at least two linkages between the scaffold and each of the binding site molecules to yield a candidate drug compound.

In one embodiment, a method is provided for attaching at least two peptide molecules to a scaffold, for instance, at least two peptides being different from each other. Such a scaffold provided with at least two looped or cyclic peptide segments is particularly useful for mimicking biological binding molecules, for instance, in diagnostic application, drug development programs, or in treatment of disease by mimicking or competing with natural compounds involved in disease.

Functional protein and polypeptide microarrays are critical for the next phase of proteomics research. Like DNA chips, protein chips or biological biochips will be able to analyze thousands of samples simultaneously, leading the way towards a complete map of the entire complement of human proteins. But, unlike DNA, proteins and peptides are not so easy to attach to chips. Where DNA is robust and able to withstand harsh experimental conditions, peptides are fragile and will denature if they aren't treated gently. Proteins and peptide fragments, such as looped peptide segments on a scaffold, cannot be dried; they must remain in a liquid environment to retain their activity. Proteins are so sensitive to their environment that they will denature at solid-liquid and liquid-air interfaces (which become considerable as assays are made ever smaller, because at the same time, surface-to-volume ratios increase). Proteins and peptides, however, have one-, two- and three-dimensional configurations as they transform from a straight chain of amino acids into a functional unit. Since measuring function is what it is all about, this aspect is critical to creating a bona fide protein or peptide microarray. To top it off, these microarrays must also be able to stand up to high-speed processing and analysis.

In a further embodiment, provided is a method for attaching a binding site molecule via at least two linkages to a scaffold, further comprising attaching at least one molecule via at least one bond to a surface, comprising contacting the molecule with a surface to allow the formation of at least one bond. A surface comprises any solid support surface, for example, a microarray surface but also a resin or carrier material used in chromatographic applications, ELISA-type assays or Biacore technology.

In one embodiment, at least one bond comprises a bond between a scaffold and a surface, more preferably between a reactive group of the scaffold and the surface. For example, a method is provided wherein a scaffold, provided with at least one molecule, reacts via its reactive group with a surface. A surface comprises a chemically activated surface, for example, a surface provided with one or more nucleophilic functionalities. For example, a nucleophilic functionality of a surface comprises a thiol or amine group. It will be understood that, for a scaffold to be capable of forming at least two linkages with at least one molecule and at least one linkage with a surface, it is preferred that the scaffold comprises at least three reactive groups.

In one embodiment, a method is provided comprising at least the following steps: providing a scaffold comprising at least three reactive groups, providing at least one binding site molecule capable of reacting with at least two reactive groups, providing a surface capable of reacting with at least one reactive group, contacting the scaffold with at least one molecule and the solid surface under conditions that allow the formation of at least two linkages between the scaffold and at least one molecule and at least one linkage between the scaffold and the surface in a coupling reaction, wherein the formation of a linkage accelerates/promotes the formation of a consecutive linkage.

Provided is a method for producing a library of compounds for identification or detection of a binding site comprising providing the library with a plurality of potential binding site molecules, further comprising constraining at least one variant binding site molecule via at least two linkages, such as a thioether bond, to an invariant molecular scaffold, the method comprising providing a scaffold comprising at least a first and a second reactive group; providing at least one binding site molecule capable of reacting with at least the first and second reactive groups; contacting the scaffold with at least one molecule to form at least two linkages between the scaffold and at least one molecule in a coupling reaction, wherein the formation of a linkage accelerates the formation of a consecutive linkage. Provided is a method for producing a molecular library comprising providing the library with a plurality of (preferably varied) conformationally constrained or looped binding site molecules, wherein the molecules are connected via at least two linkages to a molecular scaffold or scaffold.

In one embodiment, at least one binding site molecule comprises a peptide or a molecule mainly of peptidic nature. Further, a method is provided for producing a library comprising at least one peptidomimetic compound. Also provided is a library obtainable by a method hereof.

In one embodiment, provided is a library comprising variant binding site molecules each constrained via at least two linkages to an invariant molecular scaffold, wherein the binding site molecule is positionally or spatially addressable, for example, in an array fashion, if desired aided by computer directed localization and/or recognition of a specific molecule or set of molecules within the dimensions (e.g., plane or surface) of the support of the library used. In an array, the binding site molecules are, for example, addressable by their positions in a grid or matrix.

In one embodiment, provided is a support of polymeric material (a polymeric support) provided with a library of compounds in a density of at least 25 molecules per square centimeter or preferably at least 50, but more advantageously preferably at least 100, or more, such as 200 to 500 or even 1000 cyclic or looped molecules per square centimeter.

The invention thus provides a method for producing a molecular library for identification or detection of a binding site capable of interacting with a binding molecule, and thus for the identification of a candidate drug compound, the method comprising providing the library with a plurality of compounds, wherein at least part of the compounds, preferably a greater part, most preferably essentially all of the compounds, are composed of at least one variant binding site molecule linked to an invariant scaffold. For example, a library is provided comprising a plurality of binding site molecules, for instance di-SH-functionalized unprotected peptides, linked in a structurally coordinated fashion to a di(bromomethyl)benzene scaffold. Provided herein is a library of constrained potential binding site molecules at least comprising a scaffold according to the invention. For example, a library is provided comprising an array of cyclized peptide segments. Segments or stretches of amino acids can be derived from the sequence of a naturally occurring protein. They may, however, also be randomly synthesized, for example, using a combinatorial chemistry approach.

When providing such a library of compounds bound to a solid support according to the invention, there is no specific order or sequence by which an invariant scaffold, a variant binding site molecule and a solid support need to be contacted with each other. For example, following a coupling reaction in solution to attach a potential binding site molecule to a scaffold to provide a candidate compound according to the invention, the compound, typically comprising a cyclic or constrained binding site molecule, can be attached to a solid surface, for example, by spotting techniques. For instance, a cysteine-functionalized peptide is synthesized using standard Fmoc peptide chemistry and spotted onto a solid phase provided with an invariant scaffold molecule.

In another embodiment, variant binding site molecules capable of forming at least two linkages with a scaffold as provided are first synthesized or spotted on a solid surface, followed by contacting the potential binding site molecule with a scaffold as provided to induce cyclization.

A scaffold can be applied to every single spot, preferably in an automated fashion, each spot containing at least one molecule capable of reacting with the scaffold. In one embodiment, however, a scaffold is contacted with at least one molecule, such as a peptide, wherein the molecule is synthesized at the solid phase. In theory, the molecule can be sequentially synthesized wherein in a repetitive fashion, one monomer (e.g., an amino acid or a nucleotide) to another, until a (in essence polymeric) molecule of the desired length has been obtained. Not only are naturally occurring monomers used, synthetic molecules, such as peptide nucleic acid (PNA) molecules, or non-naturally occurring amino acids, or even D-amino acids, are routinely used as monomers.

In one embodiment, a library of compounds is provided wherein each compound is composed of an invariant scaffold molecule and one or more variant binding site molecules. In that case, contacting a molecule and a scaffold can be performed by the simple immersion or "dipping" of a solid support, for instance, a library minicard or another type of biochip, in a solution containing an invariant scaffold. Of course, following cyclization of a first binding site molecule on a scaffold, it is possible to link a second binding site molecule to the scaffold, and even a third or fourth molecule. A candidate drug compound according to the invention, be it in solution or on a solid support, also comprises more than one molecular scaffold or scaffold molecule. For example, as is exemplified in the detailed description, provided is a method for producing so-called "binding bodies" which mimic the binding properties of natural antibodies, as evidenced using ELISA-type assays. The invention herewith provides a molecular library that, albeit also suited for detecting or screening for continuous binding sites, is now particularly well suited for detecting or screening for discontinuous binding sites, in particular in relation to binding molecule-ligand interactions, such as, for example, protein-protein, protein-nucleic acid, and nucleic acid-nucleic acid interactions.

In yet another embodiment, a solid support is first provided with an invariant scaffold or scaffold comprising at least a first and a second reactive group onto which at least one binding site molecule is attached in one or more subsequent cyclization steps. A scaffold can be applied as a uniform layer onto a solid surface or by using spotting or edging technology. A surface comprises a chemically activated surface capable of reacting, be it reversible or irreversible, with a scaffold. Cyclization of at least one variant binding site molecule is then achieved by applying the molecule onto the surface provided with a scaffold, be it coated uniformly or applied in spots. Similar to what was mentioned before herein, here it is also possible to construct more complex candidate drug compounds comprising multiple constrained binding site molecules using one or more molecular scaffolds according to the invention.

As said, it is in general very convenient and time-saving to use a dipping or immersion procedure for providing a library of compounds according to a method as provided. For example, dipping is advantageously used for applying an invariant scaffold onto a solid support (e.g., followed by spotting of variant binding site molecules) or for contacting spotted variant binding site molecules with an invariant scaffold molecule. However, as a consequence of imperfect spotting, variant binding site molecules in neighboring spots may become linked to an invariant molecular scaffold to yield a compound composed of a scaffold linked to an unanticipated mixture of binding site molecules. Especially when the density of spotted binding site molecules is high, as is commonly the case when preparing molecular libraries, it can be envisioned that some "spill-over" areas in between spots will contain mixtures of binding site molecules. When determining the binding of a target molecule with the candidate drug compounds, for instance, using an array provided with a library of candidate compounds, one or more unforeseen compounds in these boundary areas may give rise to a "positive" binding signal. However, it is unlikely that the strength of such a signal is sufficient to obscure or interfere with truly positive hits as the density of spotted molecules will be much higher in the center of a spot. Moreover, as a result of the chemical nature of a scaffold and that of a molecule according to the invention, intramolecular cyclization is strongly preferred over intermolecular cyclization. At any rate, if formed at all, the formation of "hybrid" candidate compounds at a solid surface according to the invention is unlikely to significantly disturb the selection of a candidate drug compound according to a method as provided herein. Consequently, provided is for a library of compounds in a highly miniaturized format.

In addition, provided is a method to screen for a binding site capable of interacting with a target molecule, comprising screening a library according to the invention with at least one potential target molecule and detecting binding between a compound of the library and the target molecule. A very efficient procedure (for example, a "Loopscan") is provided herein to test the binding properties of compounds, for example, those comprising constrained binding site molecules, against one or more potential binding partners. A Loopscan approach is particularly useful for selecting a compound comprising a biding site of mainly peptidic nature, such as a peptidomimetic. Detection of binding is in general achieved with directly labeled probes comprising optically detectable (in general, fluorescent) nucleotides or antibodies.

In one embodiment, enzyme-linked (ELISA-type) assays are used, because these are typically very sensitive. Screening of such a compound library with any given molecule is simple, fast and straightforward. Hits can be translated directly into the amino acid sequence or molecular make-up of the looped structure due to the positionally defined array. It is shown herein that a library according to the invention comprising a set of overlapping, cyclized peptides corresponding to the B3 loop of follicle-stimulating hormone (FSH) was successfully used to screen for specific binding to an FSH-beta antibody 2. The antibody bound strongly to a cyclized peptide (12-mer in this case). In contrast, it did not bind to any significant extent on a polymeric surface functionalized with the corresponding linear peptides, not even at a concentration of 10 μmg/mL (see, FIG. 12). Moreover, the selectivity of the antibody is well expressed by the fact that only some of the looped peptide segments bind strongly to the antibodies. These findings clearly illustrate the importance of conformationally constrained peptides in mimicking molecular recognition.

Previously, it was virtually impossible to perform a rapid and convenient screening of the binding properties of compounds. A method hereof now provides a straightforward and simple procedure for the synthesis, immobilization, screening and selection of a candidate drug compound composed of a variant binding site molecule linked to an invariant scaffold molecule.

Also provided is a chip or minicard provided with variant binding site molecules that can be used in a variety of bioanalytical procedures, for example, in one or more methods currently used in drug discovery, diagnostics and cell biology. These methods comprise, among others, assays, be it qualitative or quantitative, to monitor the activity of an enzyme, such as a kinase, a phosphatase or a protease. Protein kinases represent almost 2% of all expressed genes and regulate a variety of essential cellular events, including proliferation, differentiation, and metabolism. Kinases have emerged as one of the most promising targets for new drug discovery since compounds that regulate kinase activity have significant potential to treat many diseases, including cancer, diabetes, and asthma. Moreover, such kinase inhibitors have the potential for significant efficacy with minimal side effects. The invention thus provides a technology which allows researchers to identify high-specificity in vitro substrates of kinases and physiological substrates for kinase target validation. Traditional approaches, evaluating individual peptides against a kinase until a substrate is found, are time consuming and often result in substrates that lack the selectivity needed for drug discovery efforts. Approaches for identifying physiological substrates for new kinases are even more complicated and time consuming.

In one embodiment hereof, a library of compounds composed of variant binding site molecules linked to an invariant scaffold is provided wherein at least one of the compounds comprises a potential substrate of an enzyme. For instance, a peptide chip comprising variant peptides linked to an invariant scaffold is provided, each compound representing a protein kinase consensus site motif, to characterize the specificity of a protein kinase. The determination of consensus phosphorylation site motifs by amino acid sequence alignment of known substrates has proven useful in this pursuit. These motifs can be helpful for predicting phosphorylation sites for specific protein kinases within a potential protein substrate. Thus far, researchers have predominantly used peptide chips with a library of short, linear amino-acid sequences describing the primary structure around the phosphoacceptor residue. Typically, such a linear peptide is highly flexible because it is attached to a solid support via one linkage. However, since the determinants of protein kinase specificity involve complex 3-dimensional interactions, these linear motifs are a significant oversimplification of the issue. They do not take into account possible secondary and tertiary structural elements or determinants from other polypeptide chains or from distant locations within the same chain. Furthermore, not all of the residues described in a particular specificity motif may carry the same weight in determining recognition and phosphorylation by the kinase. Thus, whereas a given linear peptide motif may be identified as an in vitro substrate for a given protein kinase, this does not necessarily reflect the in vivo situation. In contrast, the invention now provides a library of conformationally constrained peptides or peptide-like molecules which is of use for monitoring the activity of enzymes, such as protein kinases. A sample comprising an unknown protein kinase activity is contacted with the library and the phosphorylated compounds are identified. Advantageously, the library of candidate kinase substrates can be re-used following removal of the phosphate groups using a phosphatase, such as alkaline phosphatase.

The invention further provides a method for constraining a variant potential binding site molecule via at least two linkages to an invariant molecular scaffold to provide a candidate drug compound, the method comprising providing a scaffold comprising at least a first and a second reactive group, providing at least one binding site molecule capable of reacting with at least the first and second reactive groups, contacting the invariant scaffold with at least one binding site molecule, to form at least two linkages between the scaffold and at least one molecule in a coupling reaction, wherein the formation of a linkage accelerates the formation of a consecutive linkage.

Many published methods for constraining a molecule to a scaffold either relate to solid-phase or solution phase cyclization. Synthesis on a solid support greatly simplifies the problem of product isolation from reaction mixtures. A solid phase methodology also facilitates the division of products into multiple aliquots for multiple simultaneous reactions. However, a lead compound identified through screening of a library of compounds while being constrained to a solid surface often does not display the same features once tested in solution. Typically, several rounds of lead compound optimization are required to transform a lead compound into a soluble candidate drug compound. Importantly, a method provided herein for constraining a binding site molecule onto a scaffold molecule can be performed both on a solid support as well as in solution. Herewith, provided is a method for providing a candidate drug compound wherein the compound is bound to a solid support and wherein the compound is not bound to a solid support. This versatility has many advantages. For instance, a large variety of compounds, such as peptides, can be synthesized on a solid phase. Immobilization of a compound on a support surface, preferably in a spatially addressable fashion, allows for rapid screening of the compounds.

Figure 13:
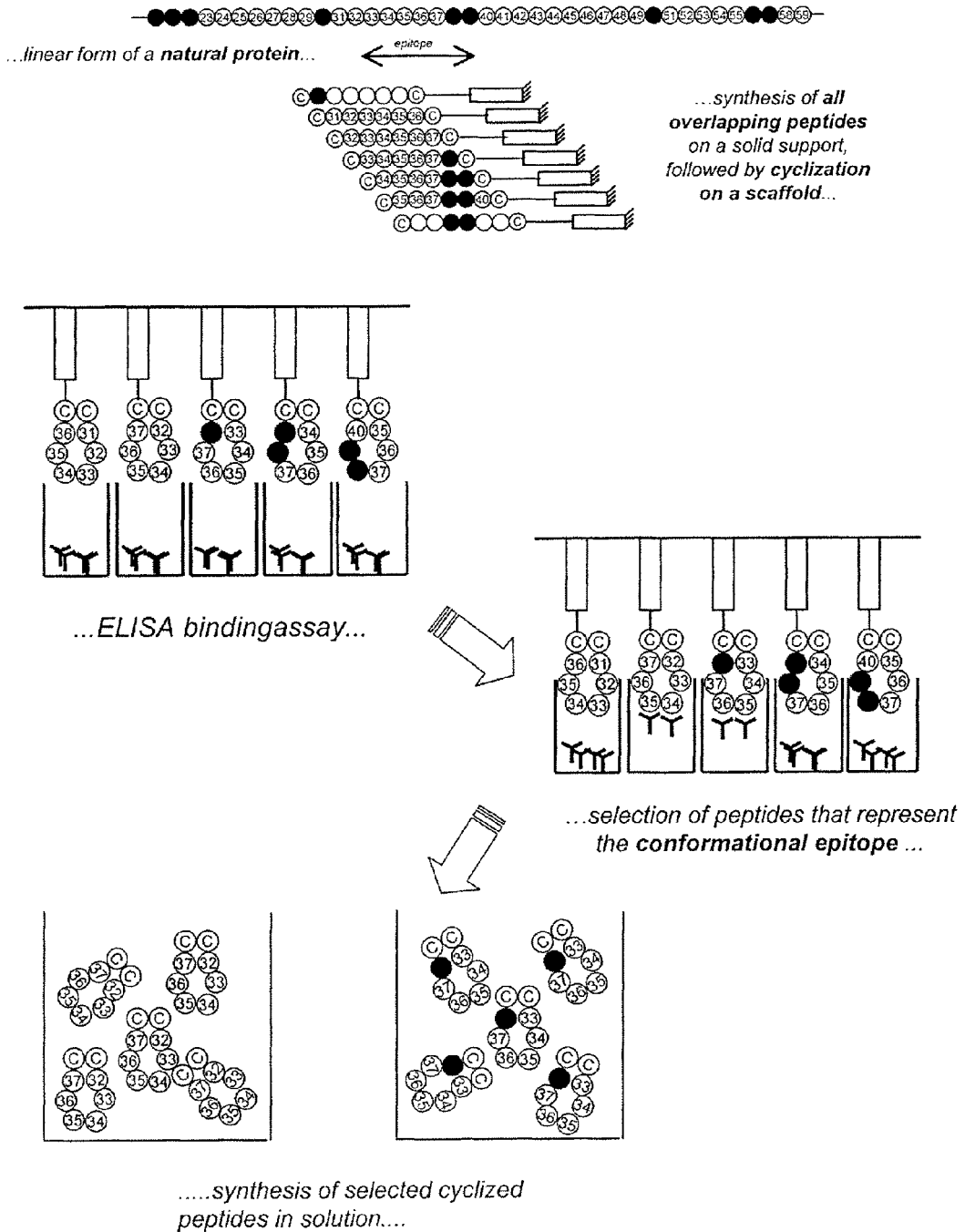
FIG. 13: Schematic representation of selecting a candidate drug compound from among a library of compounds composed of a variant peptide linked to an invariant scaffold wherein binding of an antibody is determined with the compound synthesized and bound to a solid support, followed by the synthesis of the selected candidate drug compound in solution.

After completion of the selection or the screening process, selected candidate drug compounds can subsequently be synthesized in solution, if desired at a larger scale, according to the same procedure. Thus, according to a method provided, it is now possible to synthesize a compound in solution that has essentially the same binding properties as a compound attached, be it directly or via a linker, to a solid support, for example, to an array surface. Herewith, the invention allows synthesis of a large variety of candidate drug compounds in an array fashion, enabling rapid and convenient compound selection and to simply resynthesize the selected compounds in solution. Thus, in marked contrast to conventional approaches, the cumbersome transition from (solid phase) lead compound selection to the design of a soluble drug candidate is no longer required. A method provided is advantageously used to speed up the process of drug discovery and drug development as it elegantly integrates solid phase lead compound synthesis and solution phase candidate drug compound synthesis (see FIG. 13).

A method provided herein is particularly suitable to accelerate the discovery of peptide-based drugs. Existing procedures for the development of a protein mimic or peptidomimetic for use as a pharmaceutical compound typically involve multiple screening rounds of one or more peptide segments with certain binding properties. Short linear peptides are, however, not ideal for use as a drug because of their inherent flexibility and susceptibility to proteolytic degradation. Thus, once an active peptide segment has been identified, for example, using a peptide library, current peptide-based drug discovery strategies still require modification of such a peptide lead into either a peptidomimetic or other type of soluble small-molecule drug candidate that mimics the binding characteristics of the peptide lead. According to a method provided, lead peptide modification is no longer required because the lead peptide is already a peptidomimetic itself. In fact, since provided is the synthesis of a large number of peptidomimetics, the only thing that is required involves selecting those peptidomimetics which have a desired binding characteristic.

In yet a further embodiment hereof, a method is provided for constraining at least one potential binding site molecule to a molecular scaffold, further comprising immobilizing at least one molecule attached to the scaffold via at least one bond onto a surface, comprising contacting the molecule attached to a scaffold with a surface to allow the formation of at least one bond. Such an immobilized compound comprising at least one constrained molecule allows for selecting a candidate drug compound from among a library of compounds wherein binding of a target is determined with the candidate compound bound to a solid support. For instance, an array provided with a plurality of immobilized compounds, each compound being composed of an invariant scaffold molecule to which a variant potential binding site is linked. According to a method provided, a compound comprising a scaffold and a binding molecule can be bound or immobilized to a solid surface in various ways. In one example, a compound is bound to a solid support via at least one bond between the scaffold and the surface. For instance, a scaffold comprising a reactive group reacts with a solid support surface capable of reacting with the reactive group. Preferably, the surface comprises an activated surface like a surface provided with at least one free nucleophile functionality, such as a thiol or an amine group. In another example, a compound composed of a scaffold and at least one binding site molecule is bound to a solid support via a linkage between the binding molecule and the solid support. As a specific example, standard solid phase peptide chemistry is performed to synthesize a set of variant, overlapping peptides (potential binding site molecules) in an array-like fashion on a solid support.

In one embodiment, variant binding site molecules are subsequently contacted with an invariant scaffold molecule, for example, by simply dipping the solid support into a solution of the scaffold to yield an array provided with a library of cyclic peptides bound to a solid support. This array is of use for selecting a candidate drug compound capable of binding a target molecule, wherein binding of the target molecule is determined with the candidate compound bound to a solid support. In existing procedures related to drug development, many promising lead compounds identified while being attached to a solid support lose their attraction as a candidate drug when tested for the interaction with their target molecule in solution. This is mainly because molecules often change or behave quite differently in solutions, having lost the specific constraints when attached to a solid phase. As a consequence, various rounds of modification are necessary before their candidacy as a drug may become further established. In contrast, no rounds of modification or lead compound optimization are required in a method hereof. Once a candidate drug compound has been selected by screening a library of compounds bound to a solid support, a method provided herein allows for synthesizing and testing that same compound in solution. Thus, provided is a method for selecting a candidate drug compound from among a library of compounds wherein binding of a target molecule is determined with the candidate compound bound to a solid support, such as an array, and wherein binding of the target molecule is also determined with the candidate compound in solution.

In one embodiment, provided is a composition that comprises at least one scaffold molecule linked to at least one binding site molecule wherein at least one binding site molecule is linked via at least one linkage to the scaffold molecule. More preferred, at least one binding site molecule is attached to at least one scaffold via at least two linkages in a coupling reaction, wherein the formation of a linkage accelerates the formation of a consecutive linkage. This allows attachment of a potential binding site molecule onto a scaffold in a conformationally constrained fashion, as is, for instance, highly desirable when provided a composition comprising a peptidomimetic.

In one embodiment, constraining is achieved by contacting a scaffold comprising at least a first and a second reactive group with at least one binding site molecule capable of reacting with at least the first and second reactive groups. Preferably, at least the first and second reactive groups are identical.

In one embodiment, a composition comprises at least one binding site molecule linked via at least two linkages to a scaffold molecule wherein at least one linkage is formed via a nucleophilic substitution reaction. For example, at least one reactive group of the scaffold comprises an atom that is more electronegative than carbon, which makes it a good leaving group.

In one embodiment, at least one reactive group comprises an allylic or, more preferred, a benzylic halogen atom or a halomethyl group. A composition as provided comprising at least one binding site molecule linked to at least one scaffold molecule in a nucleophilic reaction is, for example, obtained using a binding site molecule with at least one free nucleophilic functionality. A binding site molecule comprising a sulfhydryl group, for example, a SH-functionalized peptide, is advantageously used to provide a composition composed of at least one binding site molecule linked to at least one scaffold via a thioether linkage.

In a further embodiment hereof, a composition is composed of at least one scaffold linked to at least one binding site molecule, wherein the binding site molecule is linked via at least three linkages to the scaffold. For example, a composition comprising a peptide constrained onto a halomethylarene scaffold via three linkages is provided, by coupling a trifunctionalized peptide to a scaffold comprising at least three reactive groups like, for instance, a tris(bromomethyl)benzene or a derivative thereof. Of course, in a similar fashion, a composition is provided comprising at least one binding site molecule that is attached via four or even more linkages to a scaffold molecule. For example, provided is a composition comprising a complex molecular architecture composed of multiple scaffold molecules and multiple variant binding site molecules. As a specific example, provided is a method for constraining di-SH- and tri-SH-peptides onto tetra- and tribromomethyl scaffolds to provide a composition comprising multiple peptide loops on a synthetic scaffold. The coupling reaction runs without the noticeable formation of any side product because intramolecular cyclization is promoted over intramolecular cyclization. Coupling is advantageously performed in solution under mild conditions, among others, to reduce denaturation of a binding site molecule.

A composition is provided wherein at least one binding site molecule is linked to the scaffold in an essentially unprotected form. According to a method provided, linking or coupling can be performed using essentially unprotected binding site molecules, such as a molecule mainly of peptidic nature wherein the amino acid side-chains are not protected. This circumvents long and tedious procedures encountered when using classical approaches which typically involve multiple protection-deprotection cycles.

In one embodiment, a composition hereof comprises at least one binding site molecule coupled to at least one scaffold molecule, wherein coupling is performed in solution, more preferred in an aqueous solution and/or under mild conditions, such as at around room temperature. This is particularly advantageous when the composition comprises a binding site molecule which is sensitive to denaturation, like a molecule of peptidic nature.

Preferably, a composition provided herein comprises at least one scaffold molecule linked to at least one binding site molecule wherein linking is essentially completed in less than 60 minutes. It is preferred that the coupling reaction has a relatively high yield, for instance at least 30%, better more than 40%, even better more than 50%, best over 75% or even higher than that.

In one embodiment, provided is a composition composed of at least one binding molecule coupled or attached to at least one molecular scaffold, wherein the coupling reaction is performed using reactants in an essentially equimolar ratio.

A composition is composed of at least one binding site molecule linked to a scaffold wherein the scaffold is a purely synthetic scaffold. A major problem when working with purely synthetic scaffolds is their selective functionalization, which typically leads to multistep coupling procedures, often with very low yields (5-20%). In a method provided, a binding site molecule with a certain number of functionalities, for example, free cysteine groups, reacts with a symmetrically functionalized scaffold with at least the number of reactive groups in a one-step procedure, giving exclusively the 1:1 product in high yields (up to >90%). Thus, no selective functionalization of a scaffold molecule is required in a method as provided, for example when providing a library of constrained binding site molecules to select a candidate drug compound hereof.

In one embodiment, a composition is provided wherein the scaffold molecule comprises a (hetero)aromatic compound, for instance, a (hetero)aromatic scaffold wherein at least two reactive groups are in the ortho, meta or para position. Heteroaromatic scaffolds according to the invention for use when preparing a compound comprise pyridine, pyrimidine, pyrrole, furan and thiopene-like molecules. Furthermore, a composition hereof comprises a scaffold molecule that is derivable from a halomethylarene. For example, the halomethylarene comprises a bis(bromomethyl)benzene, a tris(bromomethyl)benzene, a tetra(bromomethyl)benzene or a derivative thereof. Also, compositions are provided herein comprising a binding site molecule linked to an aromatic scaffold that is based on or derivable of a multiple-ring or a fused-ring structure. For example, suitable scaffolds according to the invention include, but are not limited to, those having a biphenylene, terphenylene, naphthalene or anthracene-like backbone structure. According to the invention, the scaffolds are symmetrically functionalized with reactive groups, for example, in the ortho, meta or para position.

Furthermore, provided is a solid support that comprises a library according to the disclosure. One can think of a biochip or array surface provided with a plurality of compounds, be it synthesized at or spotted onto the surface, such as looped peptide and/or looped nucleic acid structures.

In one embodiment hereof, a solid support, such as a chip or minicard, is provided with variant binding site molecules that can be used in a variety of bioanalytical procedures, for example, in one or more methods currently used in drug discovery, diagnostics and cell biology. These methods comprise, among others, assays, be it qualitative or quantitative, to monitor the activity of an enzyme, such as a kinase, a phosphatase or a protease. Protein kinases represent almost 2% of all expressed genes and regulate a variety of essential cellular events, including proliferation, differentiation, and metabolism. Kinases have emerged as one of the most promising targets for new drug discovery since compounds that regulate kinase activity have significant potential to treat many diseases, including cancer, diabetes, and asthma. Moreover, such kinase inhibitors have the potential for significant efficacy with minimal side effects. The invention thus provides a technology which allows researchers to identify high-specificity in vitro substrates of kinases, and physiological substrates for kinase target validation. Traditional approaches, evaluating individual peptides against a kinase until a substrate is found, are time consuming and often result in substrates that lack the selectivity needed for drug discovery efforts. Approaches for identifying physiological substrates for new kinases are even more complicated and time consuming.

In one embodiment, a library of compounds composed of variant binding site molecules linked to an invariant scaffold is provided wherein at least one of the compounds comprises a potential substrate of an enzyme. For instance, a peptide chip comprising variant peptides linked to an invariant scaffold is provided, each compound representing a protein kinase consensus site motif, to characterize the specificity of a protein kinase. The determination of consensus phosphorylation site motifs by amino acid sequence alignment of known substrates has proven useful in this pursuit. These motifs can be helpful for predicting phosphorylation sites for specific protein kinases within a potential protein substrate. Thus far, researchers have predominantly used peptide chips with a library of short, linear amino acid sequences describing the primary structure around the phosphoacceptor residue. Typically, such a linear peptide is highly flexible because it is attached to a solid support via one linkage. However, since the determinants of protein kinase specificity involve complex three-dimensional interactions, these linear motifs, are a significant oversimplification of the issue. They do not take into account possible secondary and tertiary structural elements or determinants from other polypeptide chains or from distant locations within the same chain. Furthermore, not all of the residues described in a particular specificity motif may carry the same weight in determining recognition and phosphorylation by the kinase. Thus, whereas a given linear peptide motif may be identified as an in vitro substrate for a given protein kinase, this does not necessarily reflect the in vivo situation. In contrast, the disclosure now provides a library of conformationally constrained peptides or peptide-like molecules that is of use for monitoring the activity of enzymes, such as protein kinases. A method is provided for selecting a candidate drug compound from among a library of compounds wherein binding of, or recognition by, a target molecule is determined with the candidate compound bound to a solid support and also is determined with the candidate compound not bound to a solid support, wherein the target molecule comprises an enzyme. A sample comprising an unknown enzyme activity, such as a protein kinase activity, is contacted with the library and the enzymatically modified (e.g., phosphorylated, dephosphorylated, or hydrolyzed) compounds are identified. Advantageously, a library of candidate kinase substrates can be re-used following removal of the phosphate groups using a phosphatase, such as alkaline phosphatase.

In one embodiment, a library of compounds is provided for various classes of kinases like, for example, Abl kinase, FGFR kinase, Itk kinase, Lck kinase, Src kinase, Erk kinase, Akt, ATM kinase, Casein kinase, cyclin-dependent kinase, Clk2 kinase, DNA PK, EGFR kinase, GSK3 kinase, Insulin receptor kinase, p38 MAPK, PDGFR kinase, PKA, PKC or Calmodulin-dependent kinase 2. These libraries, for instance, contain a large variety of compound composed of variant peptide sequences linked to an invariant scaffold, with each sequence oriented around a phosphorylatable residue in a fixed position. After exposing the library to a kinase of interest, the compounds that have been modified by phosphorylation are identified. Phosphorylation can be measured either directly, for example, by incubating an immobilized peptide compound and a kinase of interest in the presence of radiolabeled ATP, or indirectly, for example, by using a (fluorescently) labeled phospho-specific antibody or by using another type of labeled probe which specifically recognizes a modified peptide compound. Based on the results of an enzyme screening assay as provided, it is often possible to design a specific inhibitor of a given enzyme activity. Furthermore, a compound selected using a solid-phase format according to the invention is readily re-synthesized as a soluble small molecule in solution. Herewith, a method is provided for selecting a candidate drug compound wherein the compound comprises an enzyme-modulating compound, such as an enzyme inhibitor or an enzyme activator.

Also provided is a library provided with variant phosphorylated compounds to use in a phosphatase assay. Removal of phosphate moiety by a phosphatase activity present in a sample can be detected using a phosphate-specific probe such as a phospho-specific antibody. Further provided is a library for use in a protease assay. For example, a chip or minicard is provided with variant compounds composed of variant molecules linked to an invariant scaffold, wherein each of the compounds comprises internally quenched compounds, for example, peptides provided with a donor-acceptor amino acid pair, for example, o-aminobenzamide and 3-nitrotyrosine or Lucifer Yellow and Dabsyl. Internally quenched compounds are advantageously used to monitor protease activity, based on the protease catalyzed relief of intramolecular self-quenching. Based on the results using a protease substrate library according to the invention, it is relatively straightforward to design a protease inhibitor or a lead inhibitor a given protease activity. For instance, a protease substrate peptide compound is readily converted into a protease-resistant inhibitor analog by including a non-scissile peptide bond, for instance, using a D-amino acid, at the cleavage site.

In one embodiment, a library of variant peptides linked to an invariant scaffold is screened for protein kinase activity of any of the types mentioned before. Once a lead compound is discovered, a systematic replacement analysis (for instance, via substitution of amino acids at every position for all other L- and D-amino acids possible) is performed to further optimize the activity of the lead compound. With the most active compound, a second library can now be made, in which the optimized loop construct is now combined on an invariant tetrabromo scaffold with a whole new library of random peptides that can be linked to the scaffold in a similar manner as described for the first peptide. Any combination of two loops (one random and one optimized in an earlier screening procedure) on the scaffold that shows a higher activity than that of the optimized single loop can now be further optimized by performing a similar replacement analysis on the second loop, while keeping the amino acid composition of the first loop the same. Finally, a complete replacement analysis can be run on all the amino acid positions of the optimized double-loop scaffold construct in order to maximize the kinase activity towards the lead compound. This sequential optimization approach is new and offers great potential for the lead-finding and optimization of bioactive drugs in general.

A solid support comprises a minicard, a biochip or the like allowing the testing of a plurality of compounds in an array-like fashion. Screening of candidate drug compounds bound to a solid support has raised the issue of whether the solid support interferes with the assay.

In one embodiment, at least one candidate compound of the library is attached to the solid support via a linker molecule. A compound connected via a flexible linker to a solid support is in general less restricted to the solid support. The use of a linker generally increased the rotational freedom of a molecule, which allows for the screening of more realistic binding interactions of a candidate drug compound. Advantageously, a solid support comprises an array provided with a compound library according to the invention, such as one of the minicard format, is re-used in several screening rounds. All that is required after each screening session to determine the binding of a target molecule to a candidate compound is a regeneration step to remove bound target molecules and/or other assay reagents used for the detection of a binding interaction. "Regeneration" refers to the procedure in which a target molecule is washed away from its ligand, such as a candidate drug compound comprising a looped or constrained binding site molecule, but leaving the ligand unharmed. Regeneration conditions generally have to be evaluated empirically because the combination of physical forces responsible for the binding are often unknown and the regeneration conditions must not cause irreversible damage to a compound. Regeneration of an array provided with a compound library according to the invention can, for instance, be performed by exposing the array to a small change in ionic strength or in pH. Following regeneration, the array is washed several times, for example, with distilled water, and re-equilibrated in a buffer that is used for selecting a candidate drug compound from among a library of compounds.

A major advantage of a procedure as provided lies in the fact that a compound can be synthesized both at a solid phase, such as, at an array surface, as well as in a (preferably aqueous) solution. A selected candidate drug compound according to the invention can be presented to a potential binding partner in solution. Such a binding partner comprises a soluble binding partner as well as a cell-bound binding partner like, for example, a receptor molecule.

A molecular scaffold according to the invention can also be used to stabilize an alpha-helical structure in a proteinaceous substance, for example, to enhance the helicity and stability of a solid-phase synthesized peptide. Preferably, the alpha-helix is stabilized by reacting it in a coupling reaction of the invention with a T2 or T3 scaffold.

Provided herein is a scaffold, be it in solution or immobilized onto a surface, to which at least one binding site molecule is attached by using a method hereof. Provided is a molecular scaffold that is, for example, selected from the group consisting of bis-, tris-, or tetra(halomethyl)benzene; bis-, tris-, or tetra(halomethyl)pyridine; bis-, tris-, or tetra(halomethyl)pyridazine; bis-, tris-, or tetra(halomethyl)pyrimidine; bis-, tris-, or tetra(halomethyl)pyrazine; bis-, tris-, or tetra(halomethyl)-1,2,3-triazine; bis-, tris-, or tetra-halomethyl)-1,2,4-triazine; bis-, tris-, or tetra(halomethyl)pyrrole, -furan, -thiophene; bis-, tris-, or tetra(halomethyl)imidazole, -oxazole, -thiazol; bis-, tris-, or tetra(halomethyl)-3H-pyrazole, -isooxazole, -isothiazol; bis-, tris-, or tetra(halomethyl)biphenylene; bis-, tris-, or tetra(halomethyl)terphenylene; 1,8-bis(halomethyl)naphthalene; bis-, tris-, or tetra(halomethyl)anthracene; bis-, tris-, or tetra(2-halomethylphenyl)methane; or, if applicable, another regioisomer thereof.

For example, provided is 1,2-bis(halomethyl)benzene; 3,4-bis(halomethyl)pyridine; 3,4-bis(halomethyl)pyridazine; 4,5-bis(halomethyl)pyrimidine; 4,5-bis(halomethyl)pyrazine; 4,5-bis(halomethyl)-1,2,3-triazine; 5,6-bis(halomethyl)-1,2,4-triazine; 3,4-bis(halomethyl)pyrrole, -furan, -thiophene and other regioisomers; 4,5-bis(halomethyl)imidazole, -oxazole, -thiazol; 4,5-bis(halomethyl)-3H-pyrazole, -isooxazole, -isothiazol; 2,2'-bis(halomethyl)biphenylene; 2,2''-bis(halomethyl)terphenylene; 1,8-bis(halomethyl) naphthalene; 1,10-bis(halomethyl)anthracene; bis(2-halomethylphenyl)methane; 1,2,3-tris(halomethyl)benzene; 2,3,4-tris(halomethyl)pyridine; 2,3,4-tris(halomethyl)pyridazine; 3,4,5-tris(halomethyl)pyrimidine; 4,5,6-tris(halomethyl)-1,2,3-triazine; 2,3,4-tris(halomethyl)pyrrole, -furan, -thiophene; 2,4,5-bis(halomethyl)imidazole, -oxazole, -thiazol; 3,4,5-bis(halomethyl)-1H-pyrazole, -isooxazole, -isothiazol; 2,4,2'-tris(halomethyl)biphenylene; 2,3',2''-tris(halomethyl)terphenylene; 1,3,8-tris(halomethyl)naphthalene; 1,3,10-tris(halomethyl)anthracene; bis (2-halomethylphenyl)methane; 1,2,4,5-tetra(halomethyl)benzene; 1,2,4,5-tetra(halomethyl)pyridine; 2,4,5,6-tetra(halomethyl) pyrimidine; 2,3,4,5-tetra(halomethyl)pyrrole, -furan, -thiophene; 2,2',6,6'-tetra(halomethyl)biphenylene; 2,2'',6,6''-tetra(halomethyl)terphenylene; 2,3,5,6-tetra(halomethyl) naphthalene and 2,3,7,8-tetra(halomethyl)anthracene; Bis(2,4-bis(halomethyl)phenyl)methane.

Also provided is a molecular scaffold according to the invention, the scaffold being provided with at least one binding site molecule, for example, with at least one (pseudo) peptide, peptide mimic or peptide segment.

In one embodiment, a scaffold or scaffold is provided wherein at least one molecule is attached to the scaffold via at least one linkage or bond. In one embodiment, the molecule is attached to the scaffold via more than one linkage, like via at least two or more linkages. The attachment of a molecule, for instance, a linear molecule, to a scaffold via at least two linkages is particularly suitable to fix a potential binding site molecule to a scaffold or synthetic platform in a relatively rigid conformation. For example, a scaffold-bound peptidomimetic is provided comprising multiple peptide loops or cyclized peptide segments. This can be used for mimicking discontinuous epitopes or other types of binding sites. Also provided is a compound composed of a scaffold with variant binding site molecules, attached via at least one, two, three or more linkages, for the molecular mimicry of a naturally occurring molecule. In one embodiment, the molecule comprises a pharmaceutically relevant molecule. These comprise essentially all biomolecules that are of relevance for the functioning of an organism during normal health and/or during disease. Use of a scaffold according to the invention is provided for candidate drug development or the diagnosis or the treatment of disease. For example, the biomolecule comprises a protein, a carbohydrate, a steroid, a lipid or fatty acid, or a nucleic acid. Proteins comprise, for instance, a protein hormone, an enzyme, a cytokine, a signaling molecule, an inhibitor, an activator, an antibody or a binding fragment thereof, a receptor molecule and a receptor ligand. A receptor is a molecule or a polymeric structure in or on a cell that specifically recognizes and binds a receptor ligand acting as a molecular messenger (neurotransmitter, hormone, lymphokine, cytokine, lectin, drug, etc.).

In one embodiment, a compound provided herein is used for mimicking binding sites of a pharmaceutically relevant molecule, for instance, a protein hormone, a cytokine, an antibody or a binding fragment. Furthermore, provided is a pharmaceutical or therapeutical composition comprising a molecular scaffold according to the invention. As is exemplified herein, a binding site molecule attached to a scaffold is suitably used for the molecular mimicry of a variety of different protein families, including those of the cysteine knot protein family. Provided is the design and synthesis of peptide-based structural mimics of hormones, for example, a mimic of a glycoprotein hormone family member, such as human chorionic gonadotropin (hCG) or follicle-stimulating hormone (FSH). Provided is the use of a molecular scaffold according to the invention for the manufacture of a pharmaceutical or therapeutical compound to treat a disease or disorder involving a hormonal imbalance, such as infertility and osteoporosis.

In another embodiment, a compound comprises a peptide-based structural mimic of a signaling molecule, such as a cytokine mimic. Such a compound can act as an agonist or as an antagonist of a naturally occurring signaling molecule. As is exemplified herein, tumor necrosis-factor alpha (TNF-alpha) peptidomimetic compounds with antagonistic activity are provided using a molecular scaffold according to the invention. Provided is use of molecular scaffold for the manufacture and selection of a candidate drug compound to correct a disease or disorder involving a cytokine imbalance, for instance, inflammatory processes like, for example, rheumatoid arthritis (RA).

In yet another embodiment hereof, a peptide-based mimic of the Von Willebrand Factor (vWF) is provided which has antagonistic activity. Provided is the use of a scaffold according to the invention for the manufacture of a pharmaceutical composition for the control of platelet aggregation. Platelets are discoid cell fragments derived from megakaryocytes in the bone marrow that circulate freely in the blood. Under normal conditions, they neither adhere to each other nor to other cellular surfaces. However, when blood vessels are damaged at their luminal side, platelets adhere to the exposed subendothelium. This adhesion is mediated by collagen and von Willebrand factor, both of which are exposed at or have been deposited at the subendothelial surface. Provided in the invention is a compound composed of an invariant scaffold provided with at least one binding site molecule which can be used as an anti-adhesive compound. Due to the pivotal role of platelets in thrombus formation, especially in the arterial system, inhibition of platelet function has become a central pharmacological approach. This is done to prevent and treat thromboembolic diseases such as coronary heart disease, peripheral and cerebrovascular disease and is also used during, as well as after, invasive coronary interventions. Antiplatelet therapy is an important means in the prevention and treatment of thromboembolic artery occlusions in cardiovascular diseases.

As is exemplified in the detailed description, a method provided herein allows the rapid and efficient coupling of multiple looped peptides or peptide segments onto a surface. Moreover, a method provided uses unprotected peptides in an aqueous buffer under mild conditions, which is obviously a preferred choice when attaching a peptide to a solid surface such that it retains functionality, for example, when using peptides for a peptide microarray or peptide biochip technology. The peptide arrays can be integrated into flow chambers so that the peptides are always in aqueous solution and won't be denatured. Target compounds, target biomolecules such as proteins introduced into the chambers can interact with the immobilized looped peptide segments and their binding can be detected by various methods including, but not limited to, fluorescence.

Taken together, provided is a novel and original approach for attaching at least one molecule to a scaffold. In contrast to classical approaches, a method provided comprises a one-step procedure in which multiple linkages are formed in a rapid process involving intramolecular catalysis. A method provided does essentially not require any degree of selective functionalization of the scaffold used. A coupling reaction according to the invention for providing a candidate drug compound typically gives high yields, is fast at room temperature and can be performed under mild conditions. The invention now enables the facile synthesis of a biomimetic, like a cyclic peptide or peptidomimetic, for use in, among others, drug development programs and the diagnosis and treatment of disease. These mimics may be used to induce pharmacological or therapeutic effects in humans and other animals.

In one embodiment, a compound of the invention is used to induce a specific antibody response in a subject, for example, in a vaccination program. To this end, a scaffold can be provided with at least one antigenic epitope or determinant, including a discontinuous epitope, according to a method of the invention. The compound thus obtained can be used for the formulation of a vaccine composition. Provided are mimics of viral antigens, tumor antigens, parasitic antigens and bacterial antigens.

Also provided are pharmaceutical compositions which comprise a therapeutically effective amount of a biomimetic compound, such as a peptidomimetic, obtainable by a method hereof.

The invention is further explained with the aid of the following illustrative examples.

EXPERIMENTAL SECTION

Central to the disclosure is our discovery that a variety of linear peptides with two free cysteine thiols react rapidly with a variety of dibromobenzenes. The reactions are generally performed in an aqueous solution, preferably mixtures (typically 50/50 to 5/95) of acetonitrile and 20 mM ammonium bicarbonate (pH 7.8). Based on this discovery, we present a novel strategy for attaching a potential binding site molecule to a scaffold via at least two linkages, wherein the formation of a first linkage accelerates the formation of a second linkage. The procedure is simple and straightforward and is of wide scope. A method provided is particularly attractive for the synthesis of candidate drug compounds, such as conformationally constrained peptide constructs consisting of multiple-looped peptide segments. A method provided is far superior to any existing method, as it can be used on fully unprotected peptides and does not require any degree of selective functionalization for the scaffold used. The experimental part describes the invention in more detail, but can in no way be seen as limiting the invention. The disclosure may suitably comprise, consist or consist essentially of the elements disclosed and may be practiced in the absence or presence of an element not disclosed.

Example 1

High-Yield Cyclization of SH—SH Peptides with Dibromobenzene Derivatives (T2)

Model System

As a model system, we have studied the reaction between the linear peptide Ac-CVYETVRVPGSAGGADSLYTYP-VATQC-NH$_2$ (peptide 1) (SEQ ID NO:1) and dibromo-scaffold 1,3-bis(bromomethyl)benzene (m-T2) in ammonium bicarbonate (20 mM, pH 7.9)/acetonitrile 3:1 (buffer 1). When the reactants are mixed in a 1:1 ratio at typical concentrations of 0.1 to 1.0 mM, the reaction proceeds rapidly (~20 to 30 minutes) at room temperature and exclusively give the monocyclic product in very high yield (>90%). Even when the reaction is performed in the presence of a large excess (up to 10-fold) of m-T2 scaffold, only the monocyclic product is formed, together with small amounts of by-product as a result of hydrolysis and/or aminolysis of the scaffold. The excess of scaffold and by-products can be easily removed by means of double washings with ether.

Scope

The reaction of SH—SH peptides with bis(bromomethyl) benzene derivatives is of wide scope. The reaction runs successfully with a variety of aromatic scaffolds carrying two halomethyl groups in either ortho, meta, or para position (see FIG. 4). The intramolecular catalytic effect as described in section 2.2 is different for each mode of coupling because para and meta-cyclophanes are generally more strained than ortho-cyclophanes. Also provided are all other (hetero)aromatic scaffolds with two halomethyl groups in ortho-, meta-, or para-position for the synthesis of single-loop peptides. The reaction also runs without problems for virtually all possible peptides having two free cysteine sulfhydryl groups. The reaction is fully compatible with unprotected amine (K), amido (QN), arginine (R), carboxylic acid (DE), alcohol (ST), thioether (M), imidazol (H), phenyl (F), phenol (Y), indole (W), and aliphatic (AVILP) functionalities. The only functionality that cannot be present in unprotected form is the cysteine SH, as it is an integral part of the coupling reaction, but this group can be present in a protected (StBu, Acm, Bz, etc.) form without hindering the cyclization reaction. For example, reaction of Ac-CIEKEEC(StBu)RFAIC-NH$_2$ (peptide 3) (SEQ ID NO:4 with the Cys residue at position seven modified with a StBu protection group) with m-T2 runs smoothly as long as the [peptide]≥1.0 mM.

For peptides for which the two neighboring cysteine groups are two amino acids or more apart (—CXC—, —CXXC—, —CXXXC—, . . . ), the reaction runs cleanly and in high yield (typically 80% or more). For peptides in which the two cysteine groups are only one amino acid apart (—CC—), the reaction is more sensitive to side reactions. While the desired cyclic 1:1 compound is still formed as the major product, small amounts of other products are also formed.

Cys-Knot Protein Family

We have used this strategy for the molecular mimicry of a variety of different protein families. The cysteine knot (Cys-knot) structural motif is present in peptides and proteins from a variety of species. It comprises an embedded ring formed by two disulfide bonds and their connecting backbone segments which is threaded by a third disulfide bond. It is invariably associated with a nearby beta-sheet structure and appears to be a highly efficient motif for structural stabilization.

We used the synthetic strategy for structural fixation of linear peptides as outlined above. We tested the capacity of these small peptide-based beta-FSH mimics to bind to a number of different monoclonal antibodies specific for beta-FSH. The results of detailed binding studies are described in Table 1, indicating that the looped peptide on a scaffold binds strongly to anti-FSHf3 antibodies, while the corresponding linear and the SS-looped peptides do not.

TABLE 1

Binding properties of looped peptide-mimics of FSH-β.

| entry | peptide sequence | sequence | mAb 2 $K_d$ [μM] |
|---|---|---|---|
| 1 | c-T2-[Ac-CRVPGAAHHADSLC-NH$_2$]"S-T2-S-loop" (SEQ ID NO: 5 with N-terminal modification) | β-FSH 62-73 | 2.5 |
| 2 | c-[Ac-CRVPGAAHHADSLC-NH$_2$] "SS-loop" (SEQ ID NO: 5 with N-terminal modification) | β-FSH 62-73 | 135 |
| 3 | Ac-CRVPGAAHHADSLC-NH$_2$ "linear peptide" (SEQ ID NO: 5) | β-FSH 62-73 | >1000 |

Example 2

Reaction of SH—SH-peptides with 1,3,5-tris(bromomethyl)mesitylene (T3)

Model Reaction

When peptide 1 (Ac-CVYETVRVPGSAGGADSLYTYP-VATQC-NH$_2$) (SEQ ID NO:1) is reacted with the tribromo-scaffold 1,3,5-tris(bromomethyl)mesitylene (T3), formation of the looped peptide, in which the two free SH-groups have reacted with two of the three bromomethyl groups to form a thioether linkage, is formed in very high yield (>90%). The coupling reaction is extremely fast and essentially runs to completion in less than 10 minutes at 0.1 to 1.0 mM in buffer 1. The remaining bromomethyl reactive group is highly activated in comparison to the bromomethyl functionalities in the unmodified scaffold, as complete aminolysis (or hydrolysis in phosphate-buffered solutions) of the remaining bromomethyl group is complete in a few hours. This illustrates again the activating effect of alkylthiomethyl groups on halomethyl functions at the meta-position.

Scope

The reaction of SH—SH peptides with tris(bromomethyl) benzene derivatives is of wide scope. The reaction runs successfully with a variety of symmetrically functionalized aromatic scaffolds carrying three halomethyl groups in either ortho, meta, or para position (see FIG. 6). Also provided are all other (hetero)aromatic scaffolds with three halomethyl groups in ortho-, meta-, or para-position for the synthesis of single-loop peptides. The reaction was also performed with the peptide Ac-CRGDLQC-NH$_2$ (peptide 2) (SEQ ID NO:3) and 1,4-dithiothreitol, also giving high yields of the compound without noticeable formation of (polymeric) side products. The reaction also runs without problems for virtually all possible peptides having two free cysteine sulfhydryl groups. The reaction is fully compatible with unprotected amido (Q,N), arginine (R), carboxylic acid (D,E), alcohol (ST), thioether (M), imidazol (H), phenyl (F), phenol (Y), indole (W), and aliphatic (AVILP) functionalities, but unprotected amine groups (K) rapidly react with the third bromine group (see also Example 4). The other functionality that cannot be present in unprotected form is the cysteine SH, as it is an integral part of the coupling reaction but this group can be present in a protected (StBu, Acm, Bz, etc.) form without hindering the cyclization reaction. For example, reaction of Ac-CIEKEEC(StBu)RFAIC-NH$_2$ (peptide 3) (SEQ ID NO:4) with the Cys residue at position seven modified with a StBu protection group) with T3 runs smoothly as long as the [peptide]≥1.0 mM.

For peptides for which the two neighboring cysteine groups are two amino acids or more apart (—CXC—, —CXXC—, —CXXXC—, ... ), the coupling reaction runs cleanly and in high yield (typically 80% or more). For peptides in which the two cysteine groups are only one amino acid apart (—CC—), the reaction is more sensitive to side reactions. While the desired cyclic 1:1 product is still formed as the major product, small amounts of other products are also formed.

Matrix-Scan with Cyclic Peptides Immobilized onto SH- or NH$_2$-Functionalized Surfaces The reaction of di-SH-functionalized peptides with tri-bromo scaffolds offers an excellent possibility to immobilize the cyclized peptides onto an activated surface in a structurally well-defined manner. Therefore, the tribromo scaffold T3 was mixed in a 1:1 ratio with a set of di-SH peptides in buffer solution 1 and after 10 minutes, the solution was transferred to a variety of different SH- or NH$_2$-activated surfaces. After cyclization of the peptide onto the scaffold, the remaining bromomethyl function reacts with SH- and/or NH$_2$-functions on the surface, thus connecting the peptide loops to the surface in a covalent manner. The method was used to connect short loops representing complementarity-determining regions (CDRs) from the a-lysozyme antibodies D1.4, D 44.1, HyHEL-5, and HyHEL-10. The peptide loops were spotted on the activated surface, both individually or in various combinations. The results are presented in Table 2 and clearly show the binding of lysozyme via (multiple) peptide loops (CDRs). Herewith, a method is provided for the synthesis of a compound comprising (multiple) peptide loops and surface attachment of the compound on an SH- or NH$_2$-activated surface.

TABLE 2

Matrix loop-scan of single CDRs of a-lysozymeMabs with various SH-SH peptides.

| peptide A | peptide B | mAb | binding of lysozyme at 100 μg/mL |
|---|---|---|---|
| CDR-H2 (AA$_{50}$-AA$_{57}$) | — | D 1.3, H2 | − |
| CDR-H3 (AA$_{97}$-AA$_{105}$) | — | D 1.3, H3 | − |
| CDR-H2 (AA$_{50}$-AA$_{57}$) | CDR-H3 (AA$_{97}$-AA$_{105}$) | D 1.3, H2 + H3 | ++ |
| CDR-H2 (AA$_{49}$-AA$_{59}$) | — | D 44.1, H2 | ++ |
| CDR-H3 (AA$_{97}$-AA$_{105}$) | — | D 44.1, H3 | ++ |
| CDR-H2 (AA$_{49}$-AA$_{59}$) | CDR-H3 (AA$_{97}$-AA$_{105}$) | D 44.1, H2 + H3 | +++ |

TABLE 2-continued

Matrix loop-scan of single CDRs of a-lysozymeMabs with various SH-SH peptides.

| peptide A | peptide B | mAb | binding of lysozyme at 100 μg/mL |
|---|---|---|---|
| CDR-H2 (AA$_{49}$-AA$_{59}$) | — | HyHEL-5, H2 | + |
| CDR-H3 (AA$_{97}$-AA$_{105}$) | — | HyHEL-5, H3 | − |
| CDR-H2 (AA$_{49}$-AA$_{59}$) | CDR-H3 (AA$_{97}$-AA$_{105}$) | HyHEL-5, H2 + H3 | − |
| CDR-H2 (AA$_{49}$-AA$_{59}$) | — | HyHEL-10, H2 | − |
| CDR-H3 (AA$_{97}$-AA$_{102}$) | — | HyHEL-10, H3 | + |
| CDR-H2 (AA$_{49}$-AA$_{59}$) | CDR-H3 (AA$_{97}$-AA$_{102}$) | HyHEL-10, H2 + H3 | − |

Example 3

Reaction of SH—SH-Peptides with 1,2,4,5-Tetra(Bromomethyl)Benzene (Tetrabromodurene, T4)

Model Reactions

Figure 7:
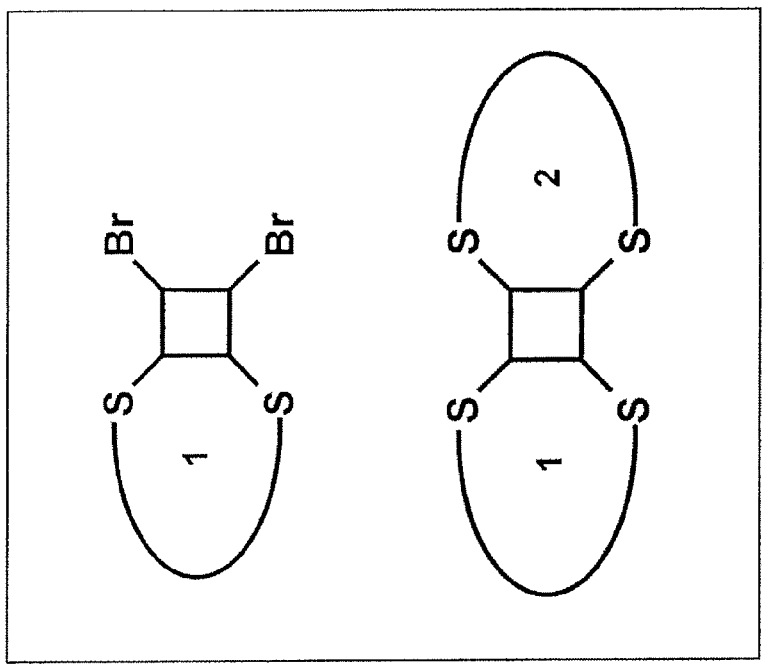
FIG. 7: Formation of single- and double-looped peptide construct via reaction of tetrabromo scaffold with di-SH-functionalized linear peptides.
Figure 7:
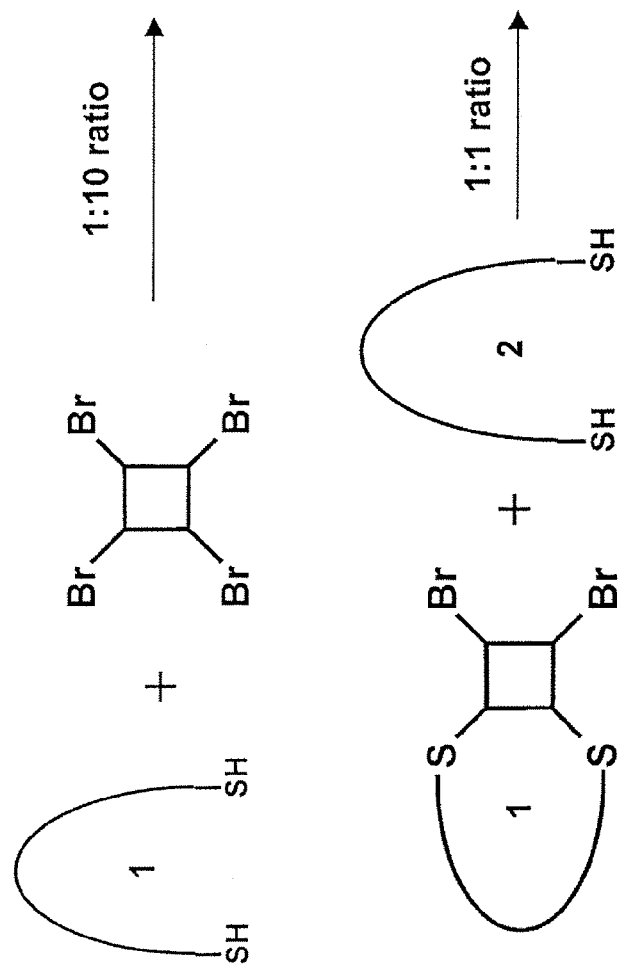

Reaction of peptides 1 and 2 with an excess of tetrabromo-scaffold 1,2,4,5-tetra(bromomethyl)benzene (T4) in a 1:10 ratio leads to the formation of the looped peptide construct peptide 1-T4 and peptide2-T4 (see FIG. 7). The products are foamed in three different isomeric forms (ortho, meta, and para), the ortho- and meta-product being formed in >90% and the para in <10%. Excess T4 was easily removed by double extraction with diethyl ether. Subsequent reaction of the 1:1-products with a second equivalent of the di-SH-peptide1 and/or 2 gives in both cases the corresponding symmetric 2:1-products in fairly good yields (50 to 80% yield).

Figure 8:
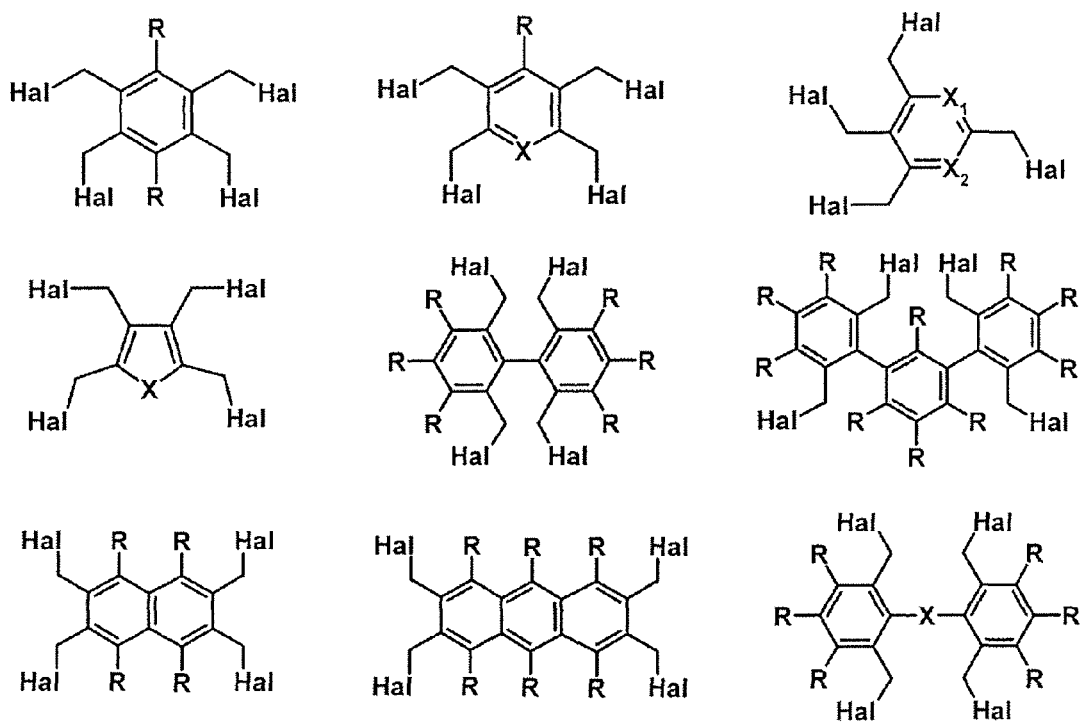
FIG. 8: Aromatic scaffolds with ortho-, meta-, or para-positioning of four bromomethyl groups: 1,2,4,5-tetra(halomethyl)benzene and other regioisomers; 1,2,4,5-tetra (halomethyl)pyridine (X=N) and other regioisomers; 2,4,5,6-tetra(halomethyl)pyrimidine ($X_1$=$X_2$=N) and other regioisomers; 2,3,4,5-tetra(halomethyl)pyrrole (X=NH), -furan (X=O), -thiophene (X=S) and other regioisomers; 2,2',6,6'-tetra(halomethyl)biphenylene; 2,2",6,6"-tetra (halomethyl)terphenylene; 2,3,5,6-tetra(halomethyl)naphthalene; 2,3,7,8-tetra(halomethyl) anthracene; and Bis(2,4-bis (halomethyl)phenyl)methane (X=$CH_2$).
Figure 9:
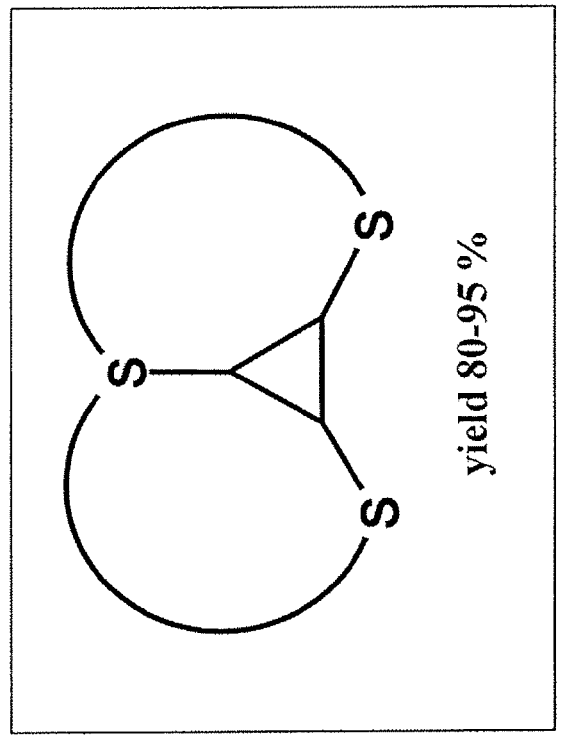
FIG. 9: Formation of double-looped peptide construct via reaction of a tribromo scaffold with tri-SH-functionalized linear peptides.
Figure 9:
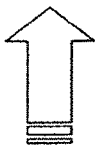
Figure 9:
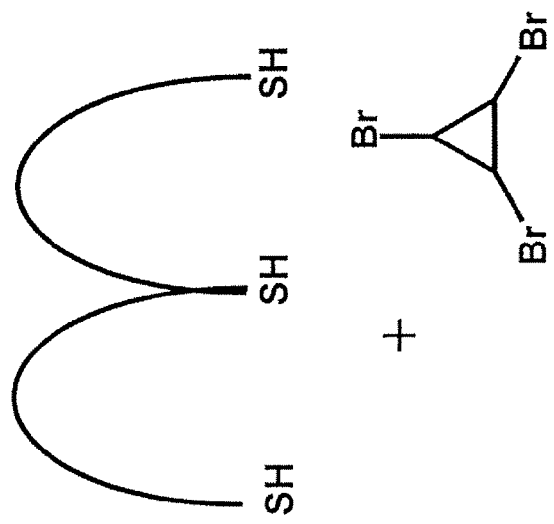
Figure 10:
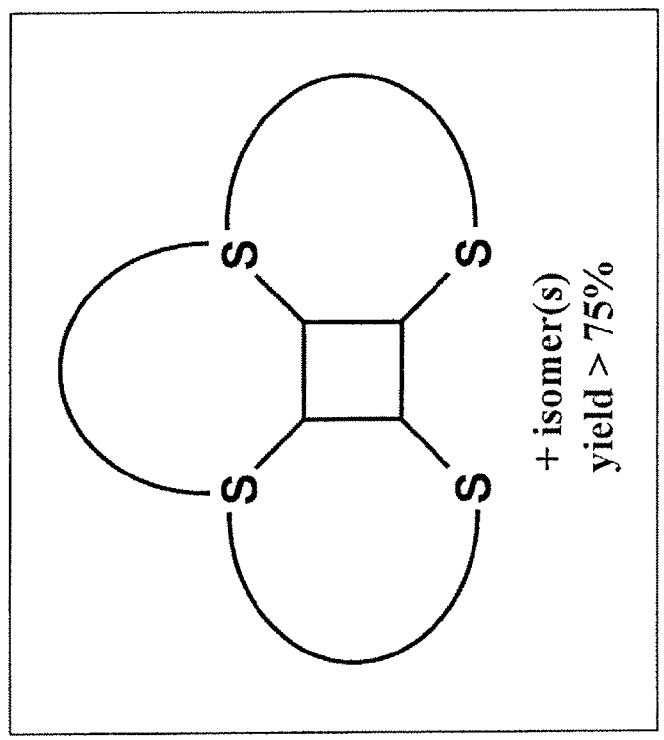
FIG. 10: Formation of double-looped peptide construct via the reaction of tetrabromo scaffolds with tetraSH-functionalized linear peptides.
Figure 10:
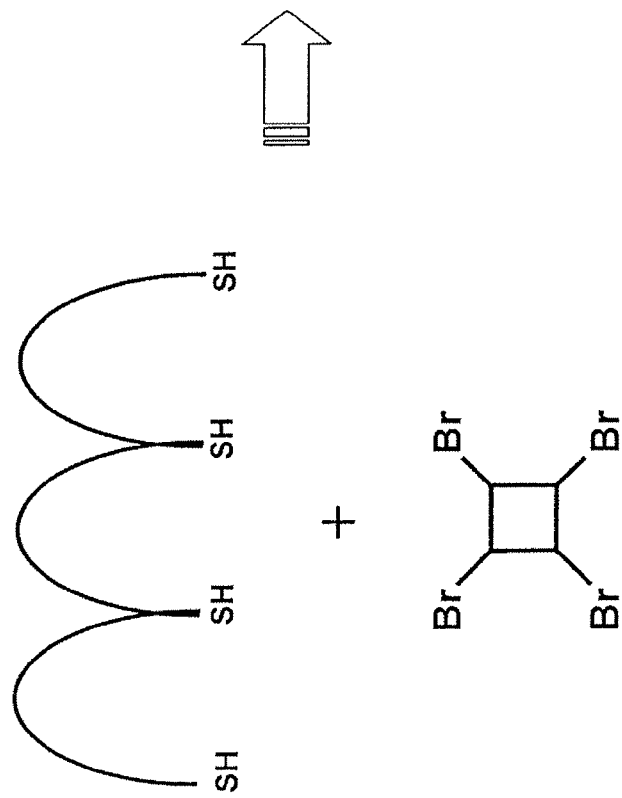

In both cases described above, the 2:1 product is most likely formed as mixture of two or more diastereoisomers. In order to solve this problem, we provide a coupling reaction with bis(3,5-bis(halomethyl)phenyl)methane shown in FIG. 8, for which all products corresponding to different modes of peptide coupling, can be simply interconverted by conformational rotations within the scaffold molecule. Provided is a method for the synthesis of a compound comprising a double-loop peptide construct using a scaffold molecule as shown in FIG. 8.

Cys-Knot Protein Family

We have used this strategy for the molecular mimicry of a variety of different protein families. The cysteine knot (Cys-knot) structural motif is present in peptides and proteins from a variety of species. It comprises an embedded ring formed by two disulfide bonds and their connecting backbone segments that is threaded by a third disulfide bond. It is invariably associated with a nearby beta-sheet structure and appears to be a highly efficient motif for structural stabilization.

1. Human Chorionic Gonadotropin (hCG) and Luteinizing Hormone (LH)

Human chorionic gonadotropin (hCG) is synthesized by the placenta throughout pregnancy and belongs to the glycoprotein hormone family, which also includes pituitary-derived luteinizing hormone (LH), follicle-stimulating hormone (FSH), and thyroid-stimulating hormone (TSH). These compounds consist of two non-identical and noncovalently bound subunits, called alpha and beta. The alpha subunits of all four hormones have a nearly identical amino acid sequence and have thus far been immunologically indistinguishable. The beta subunits carrying the biologically active determinants are considered hormone-specific. However, LH and CG, which recognize the same receptor on the target cells, provide an exception to this rule. Their beta subunits are identical over a large portion of the molecules, beta-CU mainly differing in an additional C-terminal peptide (CTP) of 30 amino acids.

For the inhibition of the specific interaction with hCG and its receptor there is a need for compounds which structurally mimic the hormone. X-ray crystallographic studies show that binding of monoclonal antibody (Mab) 3468 to beta-CG occurs via a discontinuous binding site on beta-CG. It is, therefore, likely that binding of beta-CG to the receptor also involves a discontinuous binding on the hormone. Provided is the design and synthesis of small peptide-based beta-CG mimics that strongly bind to monoclonal antibody 3468. We used the synthetic strategy for structural fixation of linear peptides as outline above.

The results of detailed binding studies are described in Table 3. The beta-CG mimics are advantageously used for the production of antisera that react specifically with hCG.

TABLE 3

Double-loop peptide construct (using T4) that mimic the binding properties of beta-CG.

| entry | peptide A | peptide B | sequence | mAb 3468 K$_d$ [μM] |
|---|---|---|---|---|
| 1 | Ac-FESCRLPGAPRGVNPVCSYA-NH$_2$ (SEQ ID NO: 6) | Ac-CEKEGAPVAC-NH$_2$ (SEQ ID NO: 7) | β-CG 58-77, 19-26 | 15 |
| 2 | Ac-FESCRLPGAPRGVNPVCSYA-NH$_2$ (SEQ ID NO: 6) | — | β-CG 58-77 | 73 |
| 3 | — | Ac-CEKEGAPVAC-NH$_2$ (SEQ ID NO: 7) | β-CG 19-26 | >1000 |

2. Follicle-Stimulating Hormone

For the inhibition of the specific interaction with beta-FSH and its receptor, there is a need for structural mimics of the hormone. Although there is no crystallographic structure describing the interaction of beta-FSH with its receptor, it is very likely that this binding site is discontinuous in nature. We designed and. synthesized a number of double-loop peptide construct on a tetrabromo-(T4)scaffold that could be used as beta-FSH mimics. We used the synthetic strategy for structural fixation of linear peptides as outlined above. We tested the capacity of these small peptide-based beta-FSH mimics to bind to a number of different monoclonal antibodies specific for beta-FSH. The results of detailed binding studies are described in Table 4, indicating that all mimics were strong binding partners of known antibodies. Furthermore, the beta-FSH mimics can be used successfully for the production of antisera that react specifically with beta-FSH.

size from dimers to extremely large multimers. During normal hemostasis, the larger multimers of vWF are responsible for facilitating platelet plug formation by forming a bridge between platelet glycoprotein IB and exposed collagen in the subendothelium. Either a lack of vWF protein or the presence of abnormalities that result in decreased polymerization may cause a loss of biological activity that is characteristic of von Willebrand's disease.

Small peptide-based vWF mimics were envisioned and designed according to a method provided using the structural fixation of linear peptides as outlined above on a tetrabromo scaffold. It is envisioned that these vWF mimics bind strongly to a number of different monoclonal antibodies specific for vWF. Importantly, the new vWF mimics can be used for the screening of antisera to identify novel antibodies that react specifically with vWF.

TABLE 4

Double-loop peptide construct (using T4) that mimics the binding properties of FSH-β

| entry | peptide A | peptide B | sequence | mAb 1 $K_d$ [μM] |
|---|---|---|---|---|
| 1 | Ac-YETCRVPGAAHHADSLCTYP-NH$_2$ (SEQ ID NO: 8) | Ac-CEKEEARFAC-NH$_2$ (SEQ ID NO: 9) | β-FSH 58-77, 19-26 | 0.27 |
| 2 | Ac-YETCRVPGAAHHADSLCTYP-NH$_2$ (SEQ ID NO: 8) | — | β-FSH 58-77 | 21 |
| 3 | — | Ac-CEKEEARFAC-NH$_2$ (SEQ ID NO: 9) | β-FSH 19-26 | >1000 |

3. Cytokine (TNF-α) Mimics

It is widely accepted today that cytokines such as TNF serve very important functions in pathophysiology, being factors that interfere strongly with the growth, differentiation and death of both immune and non-immune cell types. By directing its two transmembrane receptors to deliver signals of cellular proliferation, differentiation or apoptosis, TNF appears not only to orchestrate acute responses to infection and immunological injury, but also to act as a balancing factor required for the re-establishment of physiological homeostasis and immune regulation.

The laboratory observation that TNF-α is at the apex of the pro-inflammatory cascade of rheumatoid arthritis synovial cultures combined with the studies in animal models supporting a role of TNF-α for the development and progression of arthritis established TNF-α as a target for therapeutic intervention. Clinical trials at blocking TNF-α were initiated in 1992 and involved the use of infliximab (REMICADE®), a chimeric mouse Fv-human IgG1 monoclonal antibody of high TNF-α-neutralizing capacity produced by Centocor Inc. The results were very encouraging with rapid alleviation of pain, morning stiffness and tiredness, and reduction of swollen and tender joints within a week or two. Provided is a number of double-loop peptide constructs on a tetrabromo-scaffold which could be used as TNF-alpha antagonists. For the synthesis, the same synthetic strategy for structural fixation of linear peptides as outlined above can be used.

4. Von Willebrandt Factor (vWF)

Von Willebrand factor (vWF) is a multimeric plasma glycoprotein that is required for normal hemostatic platelet plug formation. The mature plasma protein is composed of apparently identical subunits (Mr=260,000) that are held together by disulfide bonds. The circulating vWF molecule ranges in Example 4

Reaction of tri-SH Peptides with 1,3,5-tris(bromomethyl)benzene (tribromomesitylene, T3)

Model Reactions

Reaction of the tri-SH-functionalized linear peptide Ac-CMSCDIFTNSRGKRC—NH$_2$ (peptide 4) (SEQ ID NO:10) with 1.0 equivalent of the tribromo scaffold 1,3,5-tris(bromomethyl)benzene T3 gives the corresponding double-looped peptide-scaffold construct, in which each SH-function has reacted one time with a bromomethyl function. As a result of the activation of remaining bromomethyl function by formation of the first thio-ether linkage, formation of the 1:1 product is almost exclusive, with <10% of other products being formed. Also here, the reaction can be run with excess of scaffold, without formation of di- and tri-alkylated peptide constructs.

Scope

The 1:1 reaction of tri-SH-peptides and tris(bromomethyl) benzene derivatives is of very wide scope. For peptides for which two neighboring cysteine groups are two amino acids or more apart (e.g., Ac-AHHPDTIVTCPEATQCHCGK-NH$_2$, peptide 5 (SEQ ID NO:11)), the reaction runs cleanly and in high yield (typically 80% or more). For peptides in which two of the three cysteine groups are only one amino acid apart (Ac-GAPIYQCMGCCFSRAYPTPA-NH$_2$, peptide 6 (SEQ ID NO:12)) the 1:1-product is still formed as the major product, but in this case, small amounts of other products were also found.

The described coupling strategy is also compatible with amine (K), amido (QN), arginine (R), carboxylic acid (DE), alcohol (ST), thioether (M), imidazol (H), phenyl (F), phenol (Y), indole (W), and aliphatic (AVILP) functionalities. The only functionality that cannot be present in unprotected form is the cysteine SH, as it is an integral part of the coupling reaction.

In another embodiment hereof, a method comprises the reaction of di-SH peptides with a free lysine (K) in the peptidic chain. While the lysine side chain alone is not reactive enough to react with halomethyl-activated scaffolds (i.e., in an intermolecular fashion), the intramolecular reaction between the amino group of a lysine side chain in a di-SH-functionalized peptide and the third bromomethyl group of a tribromo scaffold runs smoothly and gives rise to a product in which two bromomethyl groups have reacted with the two SH-groups, while the third bromomethyl group is attached to the lysine chain. This type of intramolecular reaction can be used to prepare a whole new set of double-looped peptide constructs.

Example 5

Reaction of tetra-SH Peptides with 1,2,4,5-tetra(bromomethyl)benzene (tetrabromodurene, T4)

Model Reactions

Reaction of the tetra-SH-functionalized linear peptide pEPLPDCCRQKTCSCKDRLYELL-OH (peptide 7) (SEQ ID NO:13) with one equivalent of the tetrabromo scaffold 1,2,4,5-tetrakis(bromomethyl)benzene (T4) gives the corresponding tri-looped peptide-scaffold construct in which each SH-function has reacted one time with a bromomethyl function, in good yield. The product is formed as a mixture of at least two different diastereoisomers.

Scope

The 1:1 reaction of tetraSH-peptides and tetrakis(bromomethyl)benzene derivatives is of very wide scope. Reaction with a conformationally flexible scaffold (see FIG. 8), in which different diastereoisomers can interconvert via rotation around the C—C bond connecting the two aromatic rings, give cleanly the desired product as a single isomer.

The problems observed with SH-functionalized peptides, in which two neighboring cysteine residues are only one amino acid apart, are not observed for tetrabromobenzene derivatives in which two out of four bromomethyl groups are in an ortho arrangement. For the other tetrabromo scaffolds, the same observations as for tribromo scaffolds were made. The described coupling strategy is fully compatible with amine (K), amido (QN), arginine (R), carboxylic acid (DE), alcohol (ST), thioether (M), imidazol (H), phenyl (F), phenol (Y), indole (W), and aliphatic (AVILP) functionalities. The only functionality that cannot be present in unprotected form is the cysteine SH, as it is an integral part of the coupling reaction. However, free cysteines can be incorporated by using the removable protecting Cys(StBu) group, which can easily be removed by reductive treatment, for example, with 1,4-DDT or ethane dithiol.

Example 6

Combination of Approaches from Previous Examples Design and Synthesis of Binding Bodies Provided is the solution-phase synthesis of multiple-loop peptides via a combination of the synthetic approaches as described in the previous examples (see FIG. 11), using the Cys(StBu) protecting group to temporarily mask part of the reactive SH-groups. The peptide constructs obtained in this way contain three or four peptide loops assembled on a synthetic platform. The constructs mimic the binding properties of natural antibodies, as evidenced using ELISA-type assays.

The reaction of di-SH- and tri-SH-peptides with tetra- (T4) and tribromo (T3) scaffolds can be easily combined for constructing complex molecular architectures consisting of multiple CDR-loops on a synthetic scaffold (3rd generation binding bodies). For example, reaction of the tri-SH-functionalized linear peptide Ac-C(StBu) CAA$_{50}$-AA$_{58}$CAA$_{89}$-AA$_{97}$CC(StBu)-NH$_2$ (CDR-H2/L3, a-lysozyme Mab D1.3, peptide 10) in acetonitrile/20 mM NH$_4$ HCO$_3$ (pH=7.8) 1:1 (concentration 0.2 mM) with 2.5 equivalents of 1,3,5-tris(bromomethyl)mesitylene at room temp. can give the corresponding double-looped peptide10-T3 construct in 30 to 60 minutes, in which each unprotected SH-functionality has reacted one time with a bromomethyl function (see FIG. 11A). Similarly, the linear peptide Ac-C(StBu)CAA$_{98}$-AA$_{103}$CAA$_{49}$-AA$_{53}$CC(StBu)-NH$_2$ (CDR-L2/H3, a-lysozyme Mab D1.3, peptide 11) reacted with 2.5 equivalents of 1,3,5-tris (bromomethyl)mesitylene at room temp. in acetonitrile/20 mM NH$_4$ HCO$_3$ (pH=7.8) 1:1 (concentration 0.2 mM) can give the corresponding double-looped peptide11-T3 construct (see FIG. 11B). Excess scaffold was removed by extraction with diethyl ether (2×). Both constructs were subsequently reacted with 100 equivalents of 1,4-DTT in acetonitrile/20 mM NH$_4$ HCO$_3$ (pH=7.8) 1:1 (concentration 1.0 mM) for 24 hours in order to remove the StBu-protecting groups of the terminal Cys-residues. After freeze-drying the reaction mixtures, the excess of DTT was removed by dissolving the residues in TFA and precipitating the peptide constructs with diethyl ether, wherein the DTT remains in solution. Finally, reaction of the peptide 10-T3 construct in the deprotected form in acetonitrile/20 mM NH$_4$ HCO$_3$ (pH=7.8) 1:1 (concentration 0.1 mM) with 10 equivalents of 1,2,4,5-tetra(bromomethyl)benzene at room temp. can give the corresponding double-looped peptide10-T3-T4 construct in 30 to 60 minutes, in which two of the four bromomethyl groups have reacted with the terminal Cys-residues of the original peptide-scaffold construct. After again washing the solution with diethyl ether (2×) to remove the excess of scaffold, the second peptide II-T3 construct was added in equimolar (1:1) amount and reaction with the peptide10-T3-T4 construct (which contains two remaining bromomethyl groups) can finally give the peptide10-T3-T4-T3-peptide 11 construct (see FIG. 11C). The construct need may be purified by preparative HPLC and can then be used as a mimic of the anti-lysozyme mAb D1.3.

Example 7

Solid-Phase Synthesis of Looped Peptides and Screening of their Binding Properties in a Loopscan The formation of peptide loops via reaction of a linear peptide containing two free sulfhydryl groups with 1,3-bis (bromomethyl)benzene scaffold was also carried out on a polypropylene surface grafted with polyacrylic acid (6% solution containing CuSO$_4$, irradiation using γ-radiation at a dose of 12 kGy) and functionalized with amino groups via coupling with t-butyloxycarbonyl-hexamethylene diamine (Boc-HMDA) using dicyclohexylcarbodiimide (DCC) with N-hydroxybenzotriazole (HOBt) and subsequent deprotection of the Boc-groups using trifluoroacetic acid (TFA). Standard Fmoc peptide chemistry was used to synthesize a set of overlapping linear peptides of 14 amino acid long peptides corresponding to the β3-loop of FSH in separate microwells of 3 µL each using our previously developed minicard format. Each peptide was synthesized with a Cys-residue in position 1, followed by the overlapping sequences of the FSH β3-loop (2-13, 3-14, 4-15, etc.) followed by another Cys-residue in the final position. Subsequently, the side-chain protecting groups were all removed by treatment using TFA with scavengers. Then, the minicards were treated for 30 to 60 minutes with a 0.5 mM solution of 1,3-dibromoxylene in 20 mM $NH_4HCO_3$ (pH 7.8) containing 50% acetonitrile, resulting in the fact that the peptides become (at least partially) cyclized via reaction with the dibromo scaffold. After this, the minicards were sonicated for 30 minutes at 70° C. in PBS-13 (pH 7.2) containing 1% SDS/0.1% BME, followed by 45 minutes in water.

Figure 12:
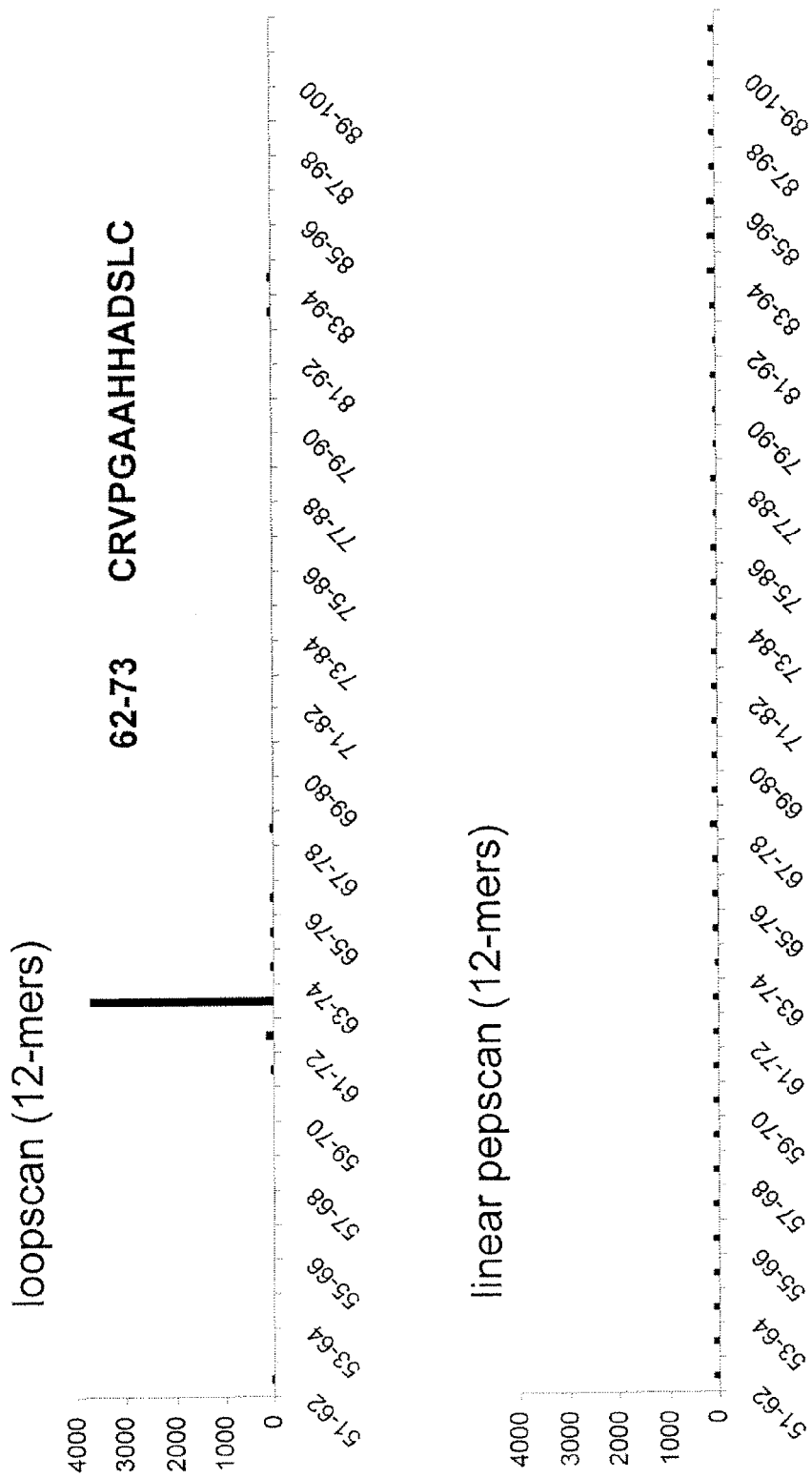
FIG. 12: ELISA results of the binding of anti-FSH monoclonal antibody 2 (10 µg/mL) in 3 µL miniwells containing overlapping a) cyclized (with m-dibromoxylene) and b) linear 12-mer peptides of the β3-loop of FSH-beta; Sequence of binding peptide: ($AA_{68}$-$AA_{79}$) Ac-CRVPGAAHHADSLC-resin (SEQ ID NO:5).

The binding properties of the cyclized peptides were tested in a sandwich ELISA-assay with anti-FSH-β mAb 2. This antibody was previously shown not to bind to any significant extent on a polymeric surface functionalized with linear 12-mer peptides, not even at a concentration of 10 µg/mL. However, as the results in FIG. 12 show, the cyclized 12-mer peptides bind strongly to mAb 2, even at concentrations as low as 1 µg/mL (OD=2500-1500). Moreover, the selectivity of antibody binding is well expressed in the fact that the antibody only binds strongly to one peptide (68-79).

Example 8

Screening of a Library of Looped Peptides and Identification of the Looped Peptide with Optimal Binding Properties in a So-Called "Loop-Optimization Scan"

Figure 14B:
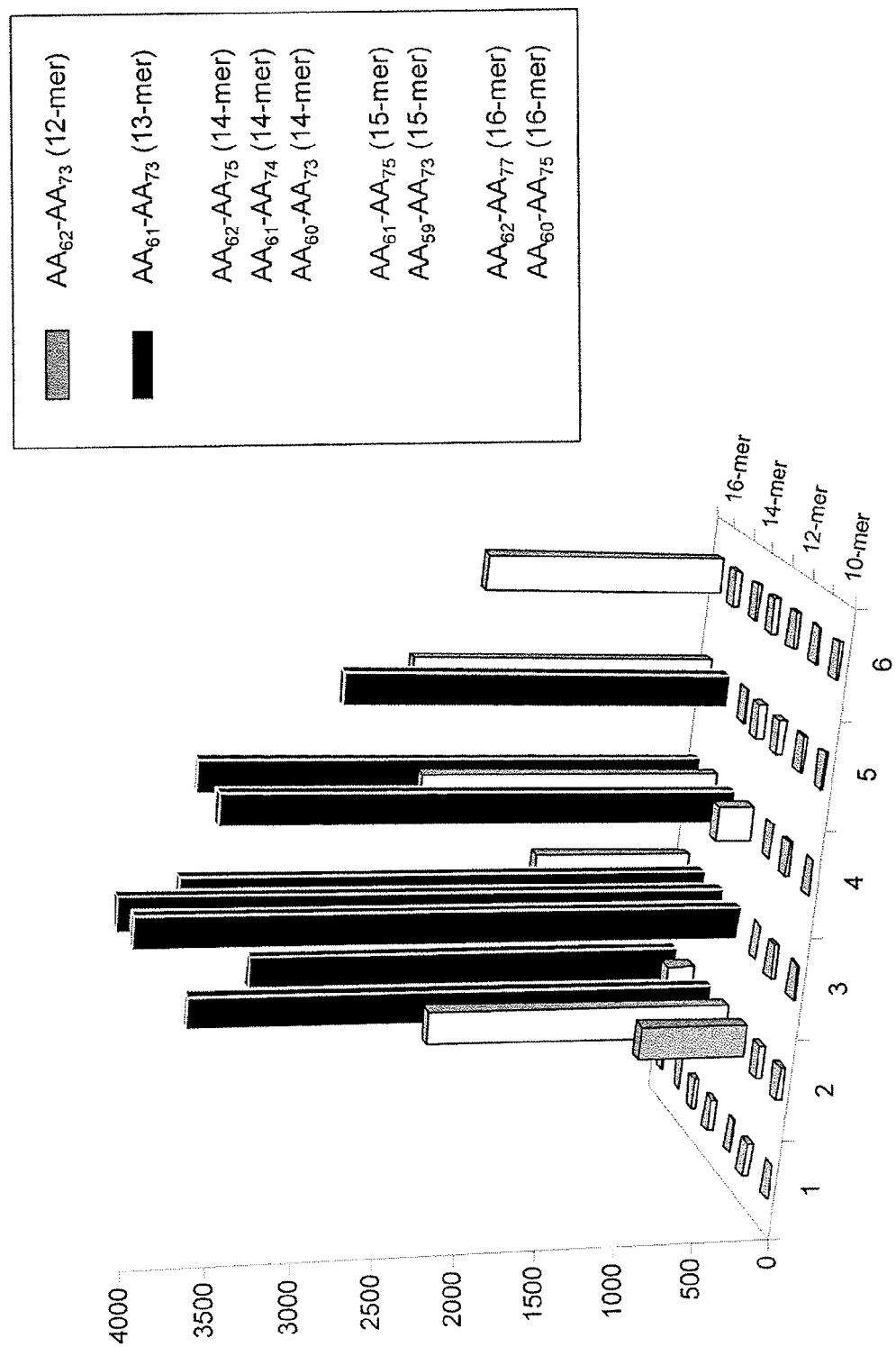
FIG. 14: ELISA results of a loop-optimization scan for the binding of anti-FSH monoclonal antibody 2 (10 µg/mL) in 3 µL miniwells containing a subset of looped peptides (FSH-133 mimics) with varying loop sizes (SEQ ID NOS:14-49) (FIG. 14A). The results (FIG. 14B) show that some of the 13-mer to 16-mer looped peptides show improved binding in comparison to the 12-mer looped peptide as identified in the 12-mer Loopscan (see Example 7, FIG. 12).

Synthesis of the looped peptides in the loop-optimization scan was carried out according to the procedure described in Example 7. After having identified, in an initial stage, the epitope or binding region of a protein, this particular region can be resynthesized in several different loop formats, i.e., using different loop sizes (e.g., CXXXXC, CXXXXXC, CXXXXXXC, etc.) and loop formats (CXXXXXC, XCXXXXC, XCXXXCX, XXCXXC, XXCXCX, XXC-CXX, etc.) (see FIG. 14A). Subsequently, the entire library of looped peptides synthesized in this way can be screened for binding with a monoclonal antibody, in this case anti-FSH mAb 2, the results of which are shown in FIG. 14B. Obviously, the looped peptides used here represent just a subset of the entire set of possible looped structures. The binding data clearly show that the binder identified in the 12-mer Loopscan (see Example 7) is far from optimized and that by increasing the loop size and varying the positions of the bridging cysteines, the binding strength can be significantly improved.

Example 9

Solid-Phase Synthesis of Double-Looped Peptides and Screening of their Binding Properties in a "Double-Loop Scan"

Figure 15A:
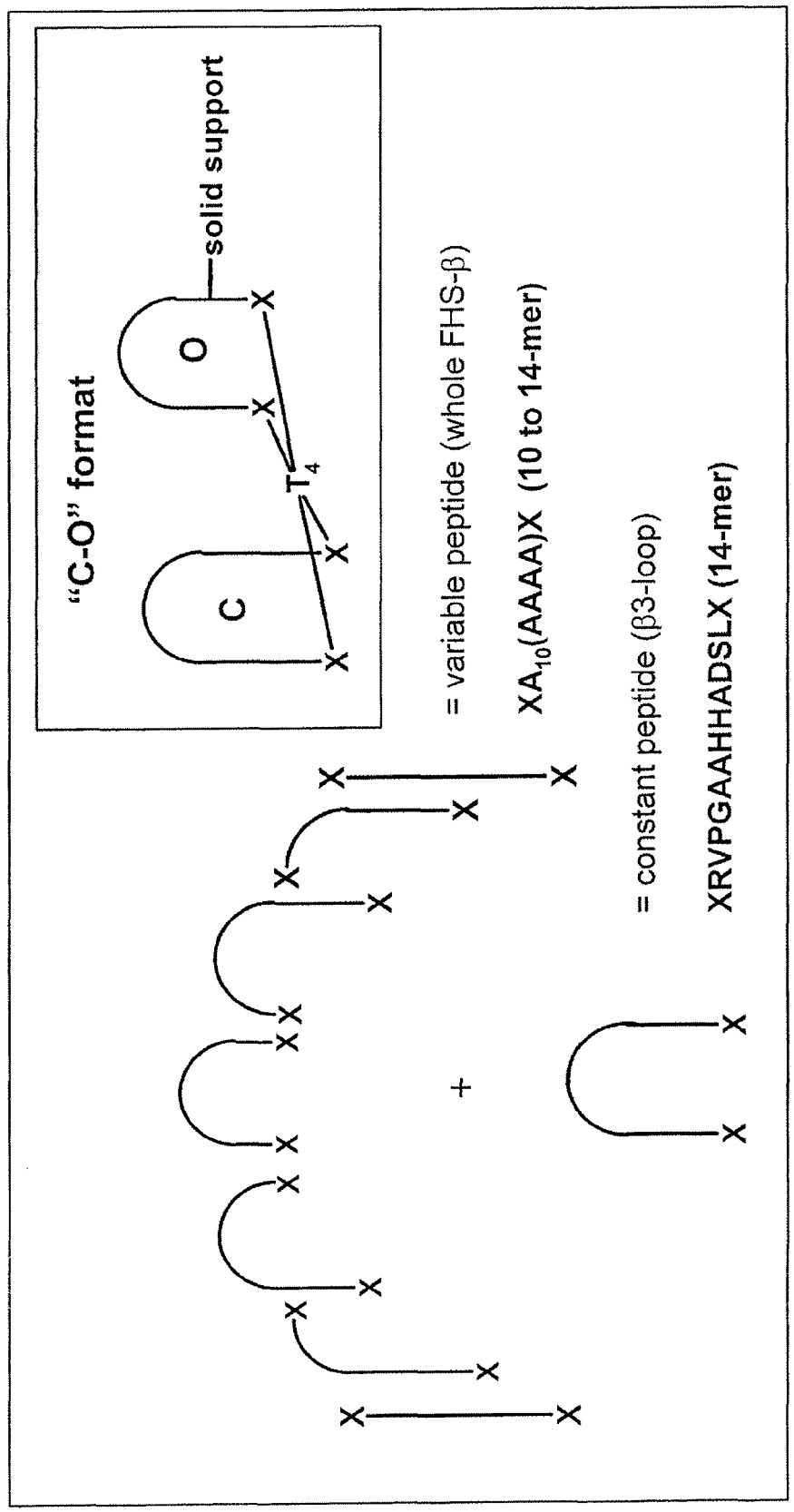
FIG. 15: ELISA results of a double-loop scan for the binding of anti-FSH monoclonal antibody 2 (0.1 µg/mL) in 3 µL miniwells containing a subset of double-loop peptide constructs (FIG. 15A) (FSH-β3-β1 mimics, constant loop: $AA_{62}$-$AA_{73}$ (SEQ ID NO:50), variable loop: $AA_2$-$AA_{32}$). The results (FIG. 15B) show that double-loop peptide constructs for which the variable loop peptide represents the top of the β1-loop of FSH-β show improved binding with mAb 2 in comparison to either

In another variation of the Loopscan (described in Example 7), a library of double-loop peptide constructs is synthesized on a solid support. This library can then be screened, for example, for binding with an antibody. Synthesis of the double-loop peptide constructs typically starts with the synthesis of linear peptides containing two cysteine units as described in Example 7. At this stage, the peptides are fully deprotected (e.g., using TFA/scavengers) and reacted with a peptide-scaffold4-construct synthesized according to the method described in Example 3. The two free sulfhydryl groups of the peptide on the solid phase thus reacts with the two unreacted bromomethyl groups in the peptide-scaffold4-construct, thus immobilizing the second peptide loop on the solid support. In this way, a library of double-looped peptide constructs can be obtained, which all possess a variable loop directly attached to the solid support, in combination with a constant peptide loop that is attached to the first loop via the scaffold 4 (see FIG. 15A).

Figure 15B:
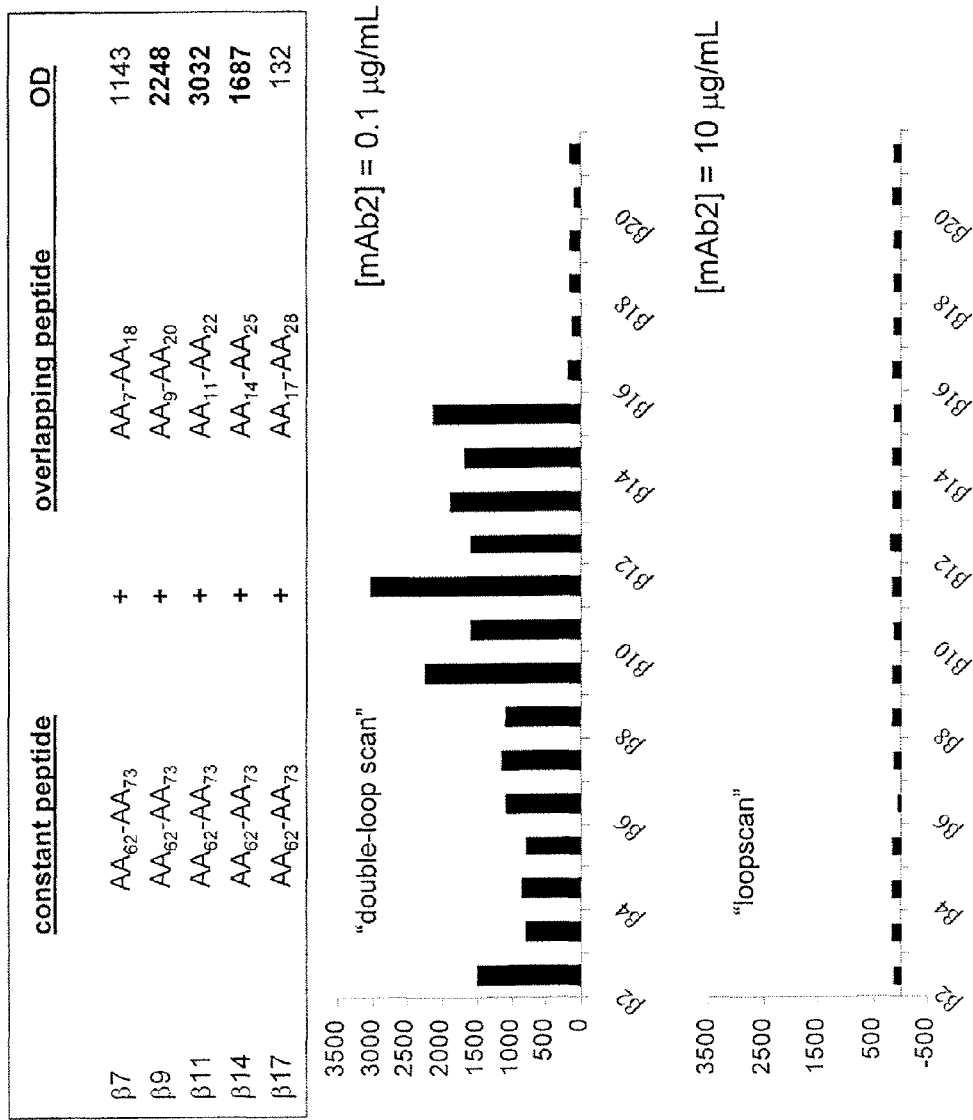

The double-loop scan was used to identify additional parts of the discontinuous epitope of FSH-β that participate in binding of mAb 2. For this particular antibody, the double-loop constructs consisting of the constant β3-loop peptide *CRVPGAAHHADSLC# (SEQ ID NO:14) and variable loops covering the β1-loop of FSH-β ($AA_{11}$-$AA_{22}$) bind significantly stronger to the antibody than either of the two peptide loops alone, which strongly suggests that the β1-loop of FSH-β is part of the binding site of mAb 2 (FIG. 15B).

Example 10

Solid-Phase Synthesis of Linear-Loop Peptide Constructs and Screening of their Binding Properties in a "Loop-Linear Scan"

Figure 16A:
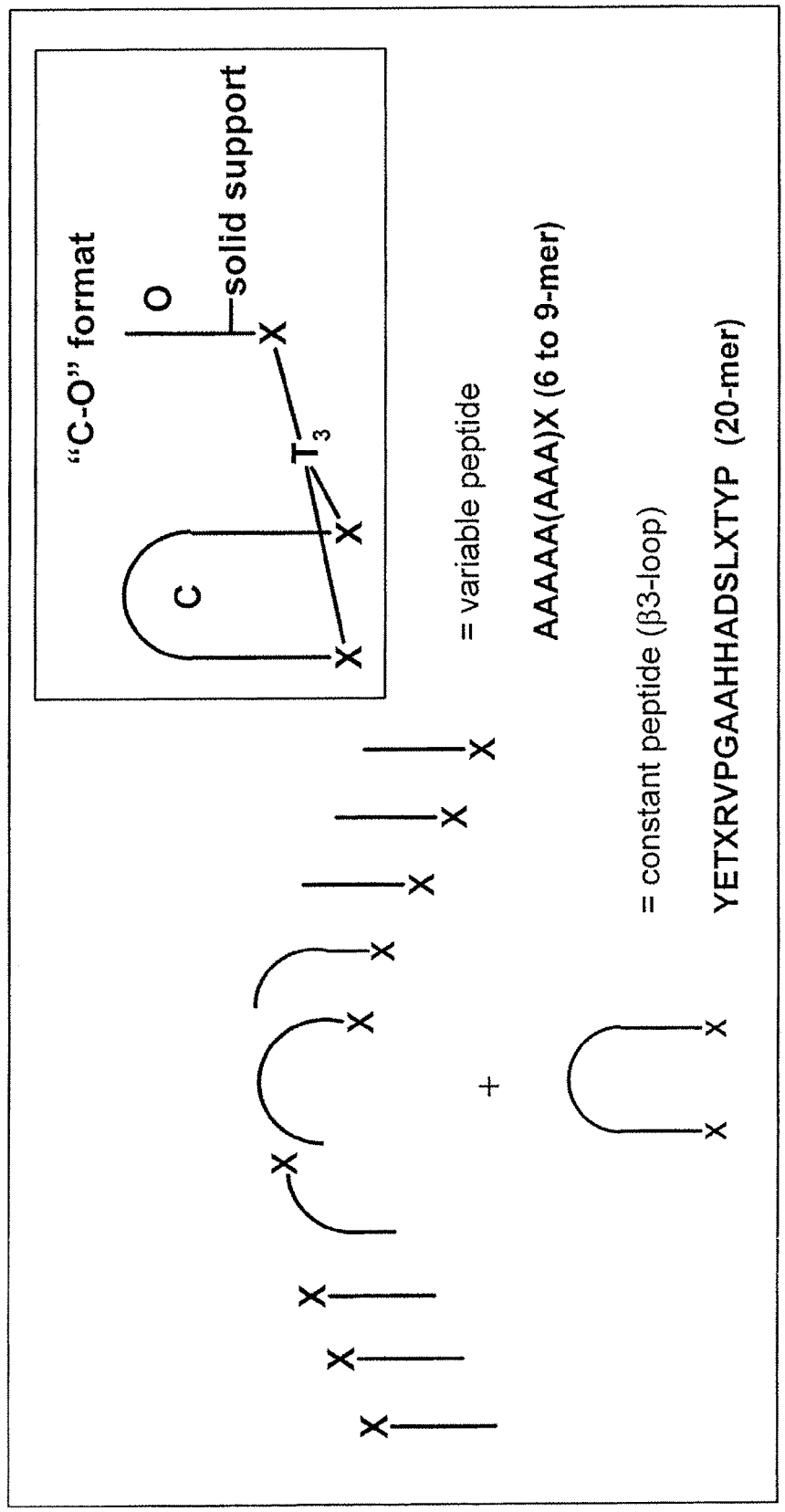
Figure 16B:
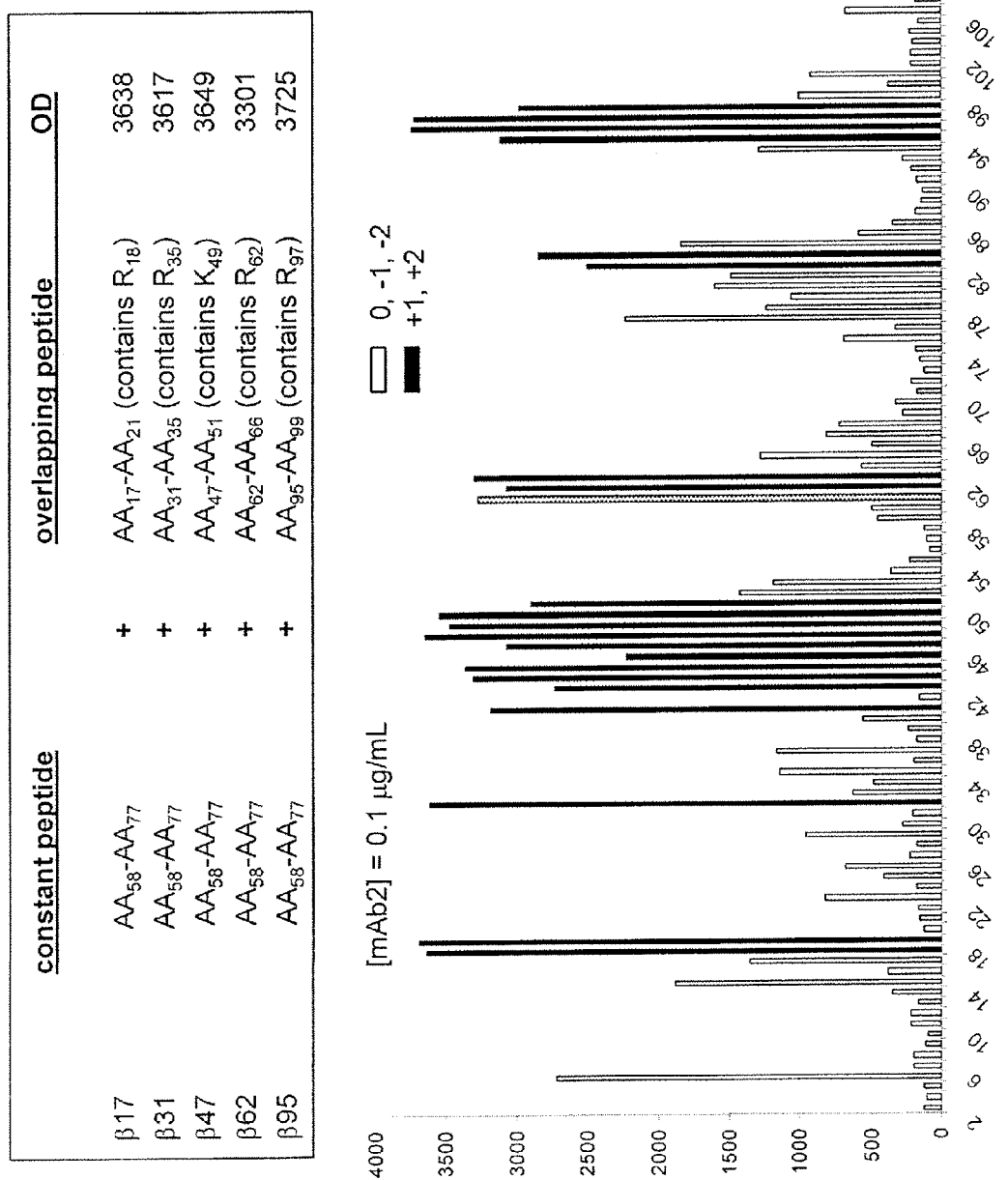

In a variation of the Loopscan (Example 7), a library of looped peptides in combination with linear peptides is synthesized on a solid support and screened for binding with an antibody. Synthesis of the loop-linear peptide constructs generally starts with the synthesis of linear peptides containing one cysteine unit as described in Example 7. At this stage, the peptides are fully deprotected (using TFA/scavengers) and reacted with a peptide-scaffold3-construct synthesized according to the method described in Example 2. The free sulfhydryl groups of the peptide on the solid phase thus reacts with the one unreacted bromomethyl group in the peptide-scaffold3-construct, thus immobilizing the constant peptide loop on the solid support. In this way, a library of loop-linear peptide constructs are obtained, which all possess a variable linear peptide directly attached to the solid support, in combination with a constant peptide loop that is attached to the linear peptide via the scaffold 3 (see FIG. 16).

The loop-linear scan was also used to identify additional parts of the discontinuous epitope of FSH-13 that participate in binding of mAb 2. For this antibody, it was shown that loop-linear constructs consisting of the constant β3-loop peptide *YETCRVPGAAHHADSLCTYP# (SEQ ID NO:8) in combination with a linear peptide carrying a net positive charge (+1 or higher), binds significantly stronger to the antibody than either the peptide loop or the linear peptide alone, which strongly suggests that a protein segment with a net-positive represents an additional part of the binding site of mAb 2.

What is claimed is:

1. A compound comprising at least two looped peptide structures attached via at least three thioether linkages to an aromatic or heteroaromatic molecule, wherein each of the at least three thioether linkages comprises a sulfur at a benzylic position on said aromatic or heteroaromatic molecule.

2. The compound of claim 1, wherein the aromatic or heteroaromatic molecule comprises a 5- or 6-membered aromatic or heteroaromatic ring.

3. The compound of claim 1, wherein the at least two looped peptide structures are attached to an aromatic molecule, and wherein each of the at least three thioether linkages is formed by reacting a halomethyl group on an aromatic ring with an SH functionality comprised within the peptide structure, thereby forming at least three thioether linkages, each comprising a sulfur at a benzylic position on said aromatic molecule.

4. The compound of claim 3, wherein the aromatic molecule is an arene.

5. The compound of claim 1, wherein the at least two looped peptide structures are attached to an aromatic molecule, and wherein each of the at least three thioether linkages is formed by reacting one of the halomethyl groups on a tris-, or tetrakis(halomethyl)-substituted aromatic ring with an SH functionality comprised within the peptide structure, thereby forming at least three thioether linkages, each comprising a sulfur at a benzylic position on said aromatic molecule.

6. The compound of claim 5, wherein the aromatic molecule is an arene.

7. The compound of claim 1, wherein the compound functions as a peptidomimetic of a biologically active protein.

8. The compound of claim 1, wherein the looped peptide structure is constrained in the compound, so as to allow the presentation of the looped peptide structure as a stable binding domain.

9. The compound of claim 1, wherein the looped peptide structure is between three and twenty-seven amino acid residues in length.

10. The compound of claim 1, wherein the at least two looped peptide structures are attached to a heteroaromatic molecule, and wherein each of the at least three thioether linkages is formed by reacting a halomethyl group on a heteroaromatic ring with an SH functionality comprised within the peptide structure, thereby forming at least three thioether linkages, each comprising a sulfur at a benzylic position on said heteroaromatic molecule.

11. The compound of claim 1, wherein the at least two looped peptide structures are attached to a heteroaromatic molecule, and wherein each of the at least three thioether linkages is formed by reacting one of the halomethyl groups on a tris-, or tetrakis(halomethyl)-substituted heteroaromatic ring with an SH functionality comprised within the peptide structure, thereby forming at least three thioether linkages, each comprising a sulfur at a benzylic position on said heteroaromatic molecule.

* * * * *

SEQUENCE LISTING

<160> NUMBER OF SEQ ID NOS: 51

<210> SEQ ID NO 1
<211> LENGTH: 27
<212> TYPE: PRT
<213> ORGANISM: Artificial
<220> FEATURE:
<223> OTHER INFORMATION: Synthetic peptide comprising cysteine

<400> SEQUENCE: 1

Cys Val Tyr Glu Thr Val Arg Val Pro Gly Ser Ala Gly Gly Ala Asp
1               5                   10                  15

Ser Leu Tyr Thr Tyr Pro Val Ala Thr Gln Cys
            20                  25

<210> SEQ ID NO 2
<211> LENGTH: 20
<212> TYPE: PRT
<213> ORGANISM: Artificial
<220> FEATURE:
<223> OTHER INFORMATION: Synthetic peptide comprising cysteine

<400> SEQUENCE: 2

Ala His His Pro Asp Thr Ile Val Thr Cys Pro Glu Ala Thr Gln Cys
1               5                   10                  15

His Cys Gly Lys
            20

<210> SEQ ID NO 3
<211> LENGTH: 7
<212> TYPE: PRT
<213> ORGANISM: Artificial
<220> FEATURE:
<223> OTHER INFORMATION: Synthetic peptide comprising cysteine

<400> SEQUENCE: 3

Cys Arg Gly Asp Leu Gln Cys
1               5

<210> SEQ ID NO 4
<211> LENGTH: 12
<212> TYPE: PRT
<213> ORGANISM: Artificial
<220> FEATURE:
<223> OTHER INFORMATION: Synthetic peptide comprising cysteine

<400> SEQUENCE: 4

Cys Ile Glu Lys Glu Glu Cys Arg Phe Ala Ile Cys
1               5                   10

<210> SEQ ID NO 5
<211> LENGTH: 14
<212> TYPE: PRT
<213> ORGANISM: Artificial
<220> FEATURE:
<223> OTHER INFORMATION: Peptide mimic of FSH-beta

<400> SEQUENCE: 5

Cys Arg Val Pro Gly Ala Ala His His Ala Asp Ser Leu Cys
1               5                   10

<210> SEQ ID NO 6
<211> LENGTH: 20
<212> TYPE: PRT
<213> ORGANISM: Artificial

```
<220> FEATURE:
<223> OTHER INFORMATION: Peptide mimicking the binding properties of
      beta-cG

<400> SEQUENCE: 6

Phe Glu Ser Cys Arg Leu Pro Gly Ala Pro Arg Gly Val Asn Pro Val
1               5                   10                  15

Cys Ser Tyr Ala
            20

<210> SEQ ID NO 7
<211> LENGTH: 10
<212> TYPE: PRT
<213> ORGANISM: Artificial
<220> FEATURE:
<223> OTHER INFORMATION: Peptide mimicking the binding properties of
      beta-cG

<400> SEQUENCE: 7

Cys Glu Lys Glu Gly Ala Pro Val Ala Cys
1               5                   10

<210> SEQ ID NO 8
<211> LENGTH: 20
<212> TYPE: PRT
<213> ORGANISM: Artificial
<220> FEATURE:
<223> OTHER INFORMATION: Peptide mimicking the binding properties of
      FSH-beta

<400> SEQUENCE: 8

Tyr Glu Thr Cys Arg Val Pro Gly Ala Ala His His Ala Asp Ser Leu
1               5                   10                  15

Cys Thr Tyr Pro
            20

<210> SEQ ID NO 9
<211> LENGTH: 10
<212> TYPE: PRT
<213> ORGANISM: Artificial
<220> FEATURE:
<223> OTHER INFORMATION: Peptide mimicking the binding properties of
      FSH-beta

<400> SEQUENCE: 9

Cys Glu Lys Glu Glu Ala Arg Phe Ala Cys
1               5                   10

<210> SEQ ID NO 10
<211> LENGTH: 15
<212> TYPE: PRT
<213> ORGANISM: Artificial
<220> FEATURE:
<223> OTHER INFORMATION: Tri-SH-functionalized linear peptide

<400> SEQUENCE: 10

Cys Met Ser Cys Asp Ile Phe Thr Asn Ser Arg Gly Lys Arg Cys
1               5                   10                  15

<210> SEQ ID NO 11
<211> LENGTH: 20
<212> TYPE: PRT
<213> ORGANISM: Artificial
<220> FEATURE:
<223> OTHER INFORMATION: Tri-SH-functionalized linear peptide

<400> SEQUENCE: 11
```

```
Ala His His Pro Asp Thr Ile Val Thr Cys Pro Glu Ala Thr Gln Cys
1               5                   10                  15

His Cys Gly Lys
            20
```

<210> SEQ ID NO 12
<211> LENGTH: 20
<212> TYPE: PRT
<213> ORGANISM: Artificial
<220> FEATURE:
<223> OTHER INFORMATION: Tri-SH-functionalized linear peptide

<400> SEQUENCE: 12

```
Gly Ala Pro Ile Tyr Gln Cys Met Gly Cys Cys Phe Ser Arg Ala Tyr
1               5                   10                  15

Pro Thr Pro Ala
            20
```

<210> SEQ ID NO 13
<211> LENGTH: 22
<212> TYPE: PRT
<213> ORGANISM: Artificial
<220> FEATURE:
<223> OTHER INFORMATION: Tetra-SH-functionalized peptide

<400> SEQUENCE: 13

```
Glu Pro Leu Pro Asp Cys Cys Arg Gln Lys Thr Cys Ser Cys Lys Asp
1               5                   10                  15

Arg Leu Tyr Glu Leu Leu
            20
```

<210> SEQ ID NO 14
<211> LENGTH: 13
<212> TYPE: PRT
<213> ORGANISM: Artificial
<220> FEATURE:
<223> OTHER INFORMATION: FSH-derived peptide

<400> SEQUENCE: 14

```
Cys Val Pro Gly Ala Ala His His Ala Asp Ser Leu Cys
1               5                   10
```

<210> SEQ ID NO 15
<211> LENGTH: 13
<212> TYPE: PRT
<213> ORGANISM: Artificial
<220> FEATURE:
<223> OTHER INFORMATION: FSH-derived peptide

<400> SEQUENCE: 15

```
Cys Arg Val Pro Gly Ala Ala His His Ala Asp Ser Cys
1               5                   10
```

<210> SEQ ID NO 16
<211> LENGTH: 13
<212> TYPE: PRT
<213> ORGANISM: Artificial
<220> FEATURE:
<223> OTHER INFORMATION: FSH-derived peptide

<400> SEQUENCE: 16

```
Cys Val Arg Val Pro Gly Ala Ala His His Ala Asp Cys
1               5                   10
```

<210> SEQ ID NO 17
<211> LENGTH: 13

```
<212> TYPE: PRT
<213> ORGANISM: Artificial
<220> FEATURE:
<223> OTHER INFORMATION: FSH-derived peptide

<400> SEQUENCE: 17

Cys Thr Val Arg Val Pro Gly Ala Ala His His Ala Cys
1               5                   10

<210> SEQ ID NO 18
<211> LENGTH: 13
<212> TYPE: PRT
<213> ORGANISM: Artificial
<220> FEATURE:
<223> OTHER INFORMATION: FSH-derived peptide

<400> SEQUENCE: 18

Cys Glu Thr Val Arg Val Pro Gly Ala Ala His His Cys
1               5                   10

<210> SEQ ID NO 19
<211> LENGTH: 13
<212> TYPE: PRT
<213> ORGANISM: Artificial
<220> FEATURE:
<223> OTHER INFORMATION: FSH-derived peptide

<400> SEQUENCE: 19

Cys Tyr Glu Thr Val Arg Val Pro Gly Ala Ala His Cys
1               5                   10

<210> SEQ ID NO 20
<211> LENGTH: 14
<212> TYPE: PRT
<213> ORGANISM: Artificial
<220> FEATURE:
<223> OTHER INFORMATION: FSH-derived peptide

<400> SEQUENCE: 20

Cys Val Pro Gly Ala Ala His His Ala Asp Ser Leu Tyr Cys
1               5                   10

<210> SEQ ID NO 21
<211> LENGTH: 14
<212> TYPE: PRT
<213> ORGANISM: Artificial
<220> FEATURE:
<223> OTHER INFORMATION: FSH-derived peptide

<400> SEQUENCE: 21

Cys Arg Val Pro Gly Ala Ala His His Ala Asp Ser Leu Cys
1               5                   10

<210> SEQ ID NO 22
<211> LENGTH: 14
<212> TYPE: PRT
<213> ORGANISM: Artificial
<220> FEATURE:
<223> OTHER INFORMATION: FSH-derived peptide

<400> SEQUENCE: 22

Cys Val Arg Val Pro Gly Ala Ala His His Ala Asp Ser Cys
1               5                   10

<210> SEQ ID NO 23
<211> LENGTH: 14
<212> TYPE: PRT
<213> ORGANISM: Artificial
```

<220> FEATURE:
<223> OTHER INFORMATION: FSH-derived peptide

<400> SEQUENCE: 23

Cys Thr Val Arg Val Pro Gly Ala Ala His His Ala Asp Cys
1               5                   10

<210> SEQ ID NO 24
<211> LENGTH: 14
<212> TYPE: PRT
<213> ORGANISM: Artificial
<220> FEATURE:
<223> OTHER INFORMATION: FSH-derived peptide

<400> SEQUENCE: 24

Cys Glu Thr Val Arg Val Pro Gly Ala Ala His His Ala Cys
1               5                   10

<210> SEQ ID NO 25
<211> LENGTH: 14
<212> TYPE: PRT
<213> ORGANISM: Artificial
<220> FEATURE:
<223> OTHER INFORMATION: FSH-derived peptide

<400> SEQUENCE: 25

Cys Tyr Glu Thr Val Arg Val Pro Gly Ala Ala His His Cys
1               5                   10

<210> SEQ ID NO 26
<211> LENGTH: 15
<212> TYPE: PRT
<213> ORGANISM: Artificial
<220> FEATURE:
<223> OTHER INFORMATION: FSH-derived peptide

<400> SEQUENCE: 26

Cys Val Pro Gly Ala Ala His His Ala Asp Ser Leu Tyr Thr Cys
1               5                   10                  15

<210> SEQ ID NO 27
<211> LENGTH: 15
<212> TYPE: PRT
<213> ORGANISM: Artificial
<220> FEATURE:
<223> OTHER INFORMATION: FSH-derived peptide

<400> SEQUENCE: 27

Cys Arg Val Pro Gly Ala Ala His His Ala Asp Ser Leu Tyr Cys
1               5                   10                  15

<210> SEQ ID NO 28
<211> LENGTH: 15
<212> TYPE: PRT
<213> ORGANISM: Artificial
<220> FEATURE:
<223> OTHER INFORMATION: FSH-derived peptide

<400> SEQUENCE: 28

Cys Val Arg Val Pro Gly Ala Ala His His Ala Asp Ser Leu Cys
1               5                   10                  15

<210> SEQ ID NO 29
<211> LENGTH: 15
<212> TYPE: PRT
<213> ORGANISM: Artificial
<220> FEATURE:
<223> OTHER INFORMATION: FSH-derived peptide

```
<400> SEQUENCE: 29

Cys Thr Val Arg Val Pro Gly Ala Ala His His Ala Asp Ser Cys
1               5                   10                  15

<210> SEQ ID NO 30
<211> LENGTH: 15
<212> TYPE: PRT
<213> ORGANISM: Artificial
<220> FEATURE:
<223> OTHER INFORMATION: FSH-derived peptide

<400> SEQUENCE: 30

Cys Glu Thr Val Arg Val Pro Gly Ala Ala His His Ala Asp Cys
1               5                   10                  15

<210> SEQ ID NO 31
<211> LENGTH: 15
<212> TYPE: PRT
<213> ORGANISM: Artificial
<220> FEATURE:
<223> OTHER INFORMATION: FSH-derived peptide

<400> SEQUENCE: 31

Cys Tyr Glu Thr Val Arg Val Pro Gly Ala Ala His His Ala Cys
1               5                   10                  15

<210> SEQ ID NO 32
<211> LENGTH: 16
<212> TYPE: PRT
<213> ORGANISM: Artificial
<220> FEATURE:
<223> OTHER INFORMATION: FSH-derived peptide

<400> SEQUENCE: 32

Cys Val Pro Gly Ala Ala His His Ala Asp Ser Leu Tyr Thr Tyr Cys
1               5                   10                  15

<210> SEQ ID NO 33
<211> LENGTH: 16
<212> TYPE: PRT
<213> ORGANISM: Artificial
<220> FEATURE:
<223> OTHER INFORMATION: FSH-derived peptide

<400> SEQUENCE: 33

Cys Arg Val Pro Gly Ala Ala His His Ala Asp Ser Leu Tyr Thr Cys
1               5                   10                  15

<210> SEQ ID NO 34
<211> LENGTH: 16
<212> TYPE: PRT
<213> ORGANISM: Artificial
<220> FEATURE:
<223> OTHER INFORMATION: FSH-derived peptide

<400> SEQUENCE: 34

Cys Val Arg Val Pro Gly Ala Ala His His Ala Asp Ser Leu Tyr Cys
1               5                   10                  15

<210> SEQ ID NO 35
<211> LENGTH: 16
<212> TYPE: PRT
<213> ORGANISM: Artificial
<220> FEATURE:
<223> OTHER INFORMATION: FSH-derived peptide

<400> SEQUENCE: 35
```

Cys Thr Val Arg Val Pro Gly Ala Ala His His Ala Asp Ser Leu Cys
1               5                   10                  15

<210> SEQ ID NO 36
<211> LENGTH: 16
<212> TYPE: PRT
<213> ORGANISM: Artificial
<220> FEATURE:
<223> OTHER INFORMATION: FSH-derived peptide

<400> SEQUENCE: 36

Cys Glu Thr Val Arg Val Pro Gly Ala Ala His His Ala Asp Ser Cys
1               5                   10                  15

<210> SEQ ID NO 37
<211> LENGTH: 16
<212> TYPE: PRT
<213> ORGANISM: Artificial
<220> FEATURE:
<223> OTHER INFORMATION: FSH-derived peptide

<400> SEQUENCE: 37

Cys Tyr Glu Thr Val Arg Val Pro Gly Ala Ala His His Ala Asp Cys
1               5                   10                  15

<210> SEQ ID NO 38
<211> LENGTH: 17
<212> TYPE: PRT
<213> ORGANISM: Artificial
<220> FEATURE:
<223> OTHER INFORMATION: FSH-derived peptide

<400> SEQUENCE: 38

Cys Val Pro Gly Ala Ala His His Ala Asp Ser Leu Tyr Thr Tyr Pro
1               5                   10                  15

Cys

<210> SEQ ID NO 39
<211> LENGTH: 17
<212> TYPE: PRT
<213> ORGANISM: Artificial
<220> FEATURE:
<223> OTHER INFORMATION: FSH-derived peptide

<400> SEQUENCE: 39

Cys Arg Val Pro Gly Ala Ala His His Ala Asp Ser Leu Tyr Thr Tyr
1               5                   10                  15

Cys

<210> SEQ ID NO 40
<211> LENGTH: 17
<212> TYPE: PRT
<213> ORGANISM: Artificial
<220> FEATURE:
<223> OTHER INFORMATION: FSH-derived peptide

<400> SEQUENCE: 40

Cys Val Arg Val Pro Gly Ala Ala His His Ala Asp Ser Leu Tyr Thr
1               5                   10                  15

Cys

<210> SEQ ID NO 41
<211> LENGTH: 17
<212> TYPE: PRT
<213> ORGANISM: Artificial

```
<220> FEATURE:
<223> OTHER INFORMATION: FSH-derived peptide

<400> SEQUENCE: 41

Cys Thr Val Arg Val Pro Gly Ala Ala His His Ala Asp Ser Leu Tyr
1               5                   10                  15

Cys

<210> SEQ ID NO 42
<211> LENGTH: 17
<212> TYPE: PRT
<213> ORGANISM: Artificial
<220> FEATURE:
<223> OTHER INFORMATION: FSH-derived peptide

<400> SEQUENCE: 42

Cys Glu Thr Val Arg Val Pro Gly Ala Ala His His Ala Asp Ser Leu
1               5                   10                  15

Cys

<210> SEQ ID NO 43
<211> LENGTH: 17
<212> TYPE: PRT
<213> ORGANISM: Artificial
<220> FEATURE:
<223> OTHER INFORMATION: FSH-derived peptide

<400> SEQUENCE: 43

Cys Tyr Glu Thr Val Arg Val Pro Gly Ala Ala His His Ala Asp Ser
1               5                   10                  15

Cys

<210> SEQ ID NO 44
<211> LENGTH: 18
<212> TYPE: PRT
<213> ORGANISM: Artificial
<220> FEATURE:
<223> OTHER INFORMATION: FSH-derived peptide

<400> SEQUENCE: 44

Cys Val Pro Gly Ala Ala His His Ala Asp Ser Leu Tyr Thr Tyr Pro
1               5                   10                  15

Val Cys

<210> SEQ ID NO 45
<211> LENGTH: 18
<212> TYPE: PRT
<213> ORGANISM: Artificial
<220> FEATURE:
<223> OTHER INFORMATION: FSH-derived peptide

<400> SEQUENCE: 45

Cys Arg Val Pro Gly Ala Ala His His Ala Asp Ser Leu Tyr Thr Tyr
1               5                   10                  15

Pro Cys

<210> SEQ ID NO 46
<211> LENGTH: 18
<212> TYPE: PRT
<213> ORGANISM: Artificial
<220> FEATURE:
<223> OTHER INFORMATION: FSH-derived peptide

<400> SEQUENCE: 46
```

```
Cys Val Arg Val Pro Gly Ala Ala His His Ala Asp Ser Leu Tyr Thr
1               5                   10                  15

Tyr Cys

<210> SEQ ID NO 47
<211> LENGTH: 18
<212> TYPE: PRT
<213> ORGANISM: Artificial
<220> FEATURE:
<223> OTHER INFORMATION: FSH-derived peptide

<400> SEQUENCE: 47

Cys Thr Val Arg Val Pro Gly Ala Ala His His Ala Asp Ser Leu Tyr
1               5                   10                  15

Thr Cys

<210> SEQ ID NO 48
<211> LENGTH: 18
<212> TYPE: PRT
<213> ORGANISM: Artificial
<220> FEATURE:
<223> OTHER INFORMATION: FSH-derived peptide

<400> SEQUENCE: 48

Cys Glu Thr Val Arg Val Pro Gly Ala Ala His His Ala Asp Ser Leu
1               5                   10                  15

Tyr Cys

<210> SEQ ID NO 49
<211> LENGTH: 18
<212> TYPE: PRT
<213> ORGANISM: Artificial
<220> FEATURE:
<223> OTHER INFORMATION: FSH-derived peptide

<400> SEQUENCE: 49

Cys Tyr Glu Thr Val Arg Val Pro Gly Ala Ala His His Ala Asp Ser
1               5                   10                  15

Leu Cys

<210> SEQ ID NO 50
<211> LENGTH: 14
<212> TYPE: PRT
<213> ORGANISM: Artificial
<220> FEATURE:
<223> OTHER INFORMATION: FSH-derived peptide
<220> FEATURE:
<221> NAME/KEY: MISC_FEATURE
<222> LOCATION: (1)..(14)
<223> OTHER INFORMATION: "Xaa" on pos. 1 and 14 stands for unknown amino
      acid

<400> SEQUENCE: 50

Xaa Arg Val Pro Gly Ala Ala His His Ala Asp Ser Leu Xaa
1               5                   10

<210> SEQ ID NO 51
<211> LENGTH: 20
<212> TYPE: PRT
<213> ORGANISM: Artificial
<220> FEATURE:
<223> OTHER INFORMATION: FSH-derived peptide
<220> FEATURE:
<221> NAME/KEY: MISC_FEATURE
<222> LOCATION: (4)..(17)
<223> OTHER INFORMATION: "Xaa" on pos. 4  and 17 stands for unknown amino
      acid
```

```
<400> SEQUENCE: 51

Tyr Glu Thr Xaa Arg Val Pro Gly Ala Ala His His Ala Asp Ser Leu
1               5                   10                  15

Xaa Thr Tyr Pro
            20
```